(12) United States Patent
Chackalamannil et al.

(10) Patent No.: US 6,326,380 B1
(45) Date of Patent: Dec. 4, 2001

(54) THROMBIN RECEPTOR ANTAGONISTS

(75) Inventors: Samuel Chackalamannil, East Brunswick; Theodros Asberom, West Orange; Yan Xia, Edison, all of NJ (US); Dario Doller, North Wales, PA (US); Martin C. Clasby, Scotch Plains; Michael F. Czarniecki, Watchung, both of NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/545,720

(22) Filed: Apr. 7, 2000

Related U.S. Application Data

(62) Division of application No. 09/197,442, filed on Nov. 23, 1998, now Pat. No. 6,063,847.
(60) Provisional application No. 60/066,518, filed on Nov. 25, 1997.

(51) Int. Cl.[7] ............... A61K 31/47; A61K 31/41; C07D 215/16; C07D 211/70
(52) U.S. Cl. ............... 514/311; 514/357; 546/178; 546/337
(58) Field of Search ............... 514/311, 357; 546/178, 337

(56) References Cited

FOREIGN PATENT DOCUMENTS

WO 94/03479   2/1994   (WO).

OTHER PUBLICATIONS

Bernatowicz et al. *J. Med. Chem., 39* (1996), p. 4879–4887.

Chackalamannil et al., *J. Amer. Chem. Soc., 118* (1996), p. 9812–9813.

*J. Organometallic Chem., 521* (1996), p. 203–210.

*J. Org. Chem. 47* (1982), p. 2825–2832.

Natarajan et al, *Int. J. Peptide Protein Res., 45* (1995), p. 145–151.

Lowry et al, *J. Biol. Chem., 193* (1951), p. 265–275.

Ahn et al, *Mol. Pharmacol., 51* (1997), p. 350–356.

Bednar et al, *Thromb. Res., 77* (1995), p. 453–463.

Even–Ram et al, *Nature Medicine, 4, 8* (1988), p. 909–914.

Primary Examiner—D. Margaret Seaman
(74) Attorney, Agent, or Firm—Anita W. Magatti

(57) ABSTRACT

Heterocyclic-substituted tricyclics of the formula

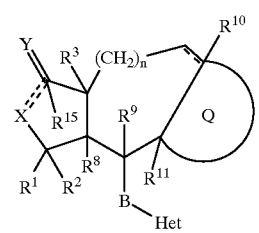

I or a pharmaceutically acceptable salt thereof, wherein:
the single dotted line represents an optional double bond;
the double dotted line represents an optional single bond;
n is 0–2;
Q is optionally substituted cycloalkyl, heterocycloalkyl, aryl or heteroaryl;
Het is an optionally substituted mono-, bi- or tricyclic heteroaromatic group;
B is $-(CH_2)_{n_3}-$, wherein $n_3$ is 0–5, $-CH_2-O-$, $-CH_2S-$, $-CH_2-NR^6-$, $-C(O)NR^6-$, $-NR^6C(O)-$,

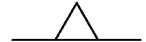

optionally substituted alkenyl or optionally substituted alkynyl;
X is $-O-$ or $-NR^6-$ when the double dotted line represents a single bond, or X is $-OH$ or $-NHR^{20}$ when the bond is absent;
Y is $=O$, $=S$, (H, H), (H, OH) or (H, $C_1-C_6$ alkoxy) when the double dotted line represents a single bond, or when the bond is absent, Y is $=O$, (H, H), (H, OH), (H, SH) or (H, $C_1-C_6$ alkoxy);
$R^{15}$ is absent when the double dotted line represents a single bond and is H, $-NR^{18}R^{19}$, or $-OR^{17}$ when the bond is absent; or Y is

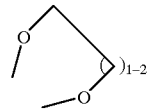

or

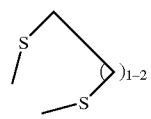

and $R^{15}$ is H or $C_1-C_6$ alkyl;
are disclosed, as well as pharmaceutical compositions containing them and a method of treating diseases associated with thrombosis, atherosclerosis, restenosis, hypertension, angina pectoris, arrhythmia, heart failure, and cancer by administering said compounds.

10 Claims, No Drawings

THROMBIN RECEPTOR ANTAGONISTS

CROSS REFERENCE TO RELATED APPLICATIONS

This application is a divisional of U.S. Ser. No. 09/197,442, filed Nov. 23, 1998, now U.S. Pat. No. 6,063,847, which claims the benefit of U.S. Provisional Application 60/066,518, filed Nov. 25, 1997.

BACKGROUND OF THE INVENTION

The present invention relates to substituted tricyclic thrombin receptor antagonists, pharmaceutical compositions containing them and their use in the treatment of diseases associated with thrombosis, atherosclerosis, restenosis, hypertension, angina pectoris, arrhythmia, heart failure, cerebral ischemia and cancer.

Thrombin is known to have a variety of activities in different cell types and thrombin receptors are known to be present in such cell types as human platelets, vascular smooth muscle cells, endothelial cells and fibroblasts. It is therefore expected that thrombin receptor antagonists will be useful in the treatment of thrombotic, inflammatory, atherosclerotic and fibroproliferative disorders, as well as other disorders in which thrombin and its receptor play a pathological role.

Thrombin receptor antagonists peptides have been identified based on structure-activity studies involving substututions of amino acids on thrombin receptors. In Bernatowicz et al, *J. Med. Chem.*, 39 (1996), p. 4879–4887, tetra- and pentapeptides are disclosed as being potent thrombin receptor antagonists, for example N-trans-cinnamoyl-p-fluoroPhe-p-guanidinoPhe-Leu-Arg-NH$_2$ and N-trans-cinnamoyl-p-fluoroPhe-p-guanidinoPhe-Leu-Arg-Arg-NH$_2$. Peptide thrombin receptor anatgonists are also disclosed in WO 94/03479, published Feb. 17, 1994.

Himbacine, a piperidine alkaloid of the formula

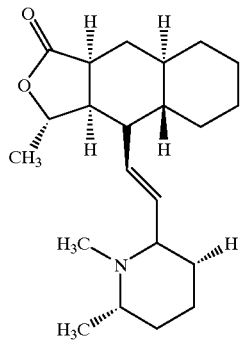

has been identified as a muscarinic receptor antagonist. The total synthesis of (+)-himbacine is disclosed in Chackalamannil et al, *J. Am.Chem Soc.*, 118 (1996), p. 9812–9813.

SUMMARY OF THE INVENTION

The present invention relates to thrombin receptor antagonists represented by the formula I

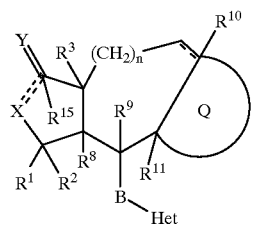

or a pharmaceutically acceptable salt thereof, wherein:
  the single dotted line represents an optional double bond;
  the double dotted line represents an optional single bond;
  n is 0–2;
  Q is

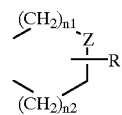

wherein
  $n_1$ and $n_2$ are independently 0–2; or when the double bond is not present, Q is also fused R-substituted aryl or R-substituted heteroaryl;
  R is 1 to 3 substituents independently selected from the group consisting of H, $C_1$–$C_6$ alkyl, halogen, hydroxy, amino, ($C_1$–$C_6$)alkylamino, ($C_1$–$C_6$) dialkylamino, ($C_1$–$C_6$)alkoxy, —COR$^{16}$, —COOR$^{17}$, —SOR$^{16}$, —SO$_2$R$^{16}$, —NR$^{16}$COR$^{16a}$, —NR$^{16}$COOR$^{16a}$, —NR$^{16}$CONR$^4$R$^5$, fluoro-($C_1$–$C_6$)alkyl, difluoro($C_1$–$C_6$)alkyl, trifluoro ($C_1$–$C_6$)alkyl, $C_3$–$C_6$ cycloalkyl, $C_2$–$C_6$ alkenyl, aryl ($C_1$–$C_6$)alkyl, aryl($C_2$–$C_6$)alkenyl, heteroaryl ($C_1$–$C_6$)alkyl, heteroaryl($C_2$–$C_6$)alkenyl, hydroxy ($C_1$–$C_6$)alkyl, amino($C_1$–$C_6$)alkyl, aryl and thio ($C_1$–$C_6$)alkyl;
  R$^1$ and R$^2$ are independently selected from the group consisting of H, $C_1$–$C_6$ alkyl, fluoro($C_1$–$C_6$)alkyl, difluoro($C_1$–$C_6$)alkyl, trifluoro-($C_1$–$C_6$)alkyl, $C_3$–$C_6$ cycloalkyl, $C_2$–$C_6$ alkenyl, aryl($C_1$–$C_6$)alkyl, aryl ($C_2$–$C_6$)alkenyl, heteroaryl($C_1$–$C_6$)alkyl, heteroaryl ($C_2$–$C_6$)alkenyl, hydroxy($C_1$–$C_6$)alkyl, amino($C_1$–$C_6$) alkyl, aryl and thio($C_1$–$C_6$)alkyl; or R$^1$ and R$^2$ together form a =O group;
  R$^3$ is H, hydroxy, $C_1$–$C_6$ alkoxy, —SOR$^{16}$, —SO$_2$R$^{17}$, —C(O)OR$^{17}$, —C(O)NR$^{18}$R$^{19}$, $C_1$–$C_6$ alkyl, halogen, fluoro($C_1$–$C_6$)alkyl, difluoro($C_1$–$C_6$)alkyl, trifluoro ($C_1$–$C_6$)alkyl, $C_3$–$C_6$ cycloalkyl, $C_2$–$C_6$ alkenyl, aryl ($C_1$–$C_6$)alkyl, aryl($C_2$–$C_6$)alkenyl, heteroaryl($C_1$–$C_6$) alkyl, heteroaryl($C_2$–$C_6$)alkenyl, hydroxy($C_1$–$C_6$) alkyl, amino($C_1$–$C_6$)alkyl, aryl or thio($C_1$–$C_6$)alkyl;
  Het is a mono-, bi- or tricyclic heteroaromatic group of 5 to 14 atoms comprised of 1 to 13 carbon atoms and 1 to 4 heteroatoms independently selected from the group consisting of N, O and S, wherein a ring nitrogen can form an N-oxide or a quaternary group with a $C_1$–$C_4$ alkyl group, wherein Het is attached to B by a carbon atom ring member, and wherein the Het group is substituted by 1 to 4 substituents, W, independently selected from the group consisting of H; $C_1$–$C_6$ alkyl; fluoro($C_1$–$C_6$)alkyl; difluoro($C_1$–$C_6$)alkyl; trifluoro-($C_1$–$C_6$)-alkyl; $C_3$–$C_6$ cycloalkyl; heterocycloalkyl;

heterocycloalkyl substituted by $C_1$–$C_6$ alkyl or $C_2$–$C_6$ alkenyl; $C_2$–$C_6$ alkenyl; $R^{21}$-aryl($C_1$–$C_6$)alkyl; $R^{21}$-aryl-($C_2$–$C_6$)-alkenyl; heteroaryl($C_1$–$C_6$)alkyl; heteroaryl($C_2$–$C_6$)-alkenyl; hydroxy($C_1$–$C_6$)alkyl; dihydroxy($C_1$–$C_6$)alkyl; amino($C_1$–$C_6$)alkyl; ($C_1$–$C_6$) alkylamino-($C_1$–$C_6$)alkyl; di-(($C_1$–$C_6$)alkyl)-amino ($C_1$–$C_6$)alkyl; thio($C_1$–$C_6$)alkyl; $C_1$–$C_6$ alkoxy; $C_2$–$C_6$ alkenyloxy; halogen; —$NR^4R^5$; —CN; —OH; —$COOR^{17}$; —$COR^{16}$; —$OSO_2CF_3$; —$CH_2OCH_2CF_3$; ($C_1$–$C_6$)alkylthio; —$C(O)NR^4R^5$; —$OCHR^6$-phenyl; phenoxy-($C_1$–$C_6$)alkyl; —$NHCOR^{16}$; —$NHSO_2R^{16}$; biphenyl; —$OC(R^6)_2COOR^7$; —$OC(R^6)_2C(O)NR^4R^5$; ($C_1$–$C_6$)alkoxy; $C_1$–$C_6$ alkoxy substituted by ($C_1$–$C_6$) alkyl, amino, —OH, $COOR^{17}$, —$NHCOOR^{17}$, —$CONR^4R^5$, aryl, aryl substituted by 1 to 3 substutuents independently selected from the group consisting of halogen, —$CF_3$, $C_1$–$C_6$ alkyl, $C_1$–$C_6$ alkoxy and —$COOR^{17}$, aryl wherein adjacent carbons form a ring with a methylenedioxy group, —$C(O)NR^4R^5$ and heteroaryl;

$R^{21}$-aryl; aryl wherein adjacent carbons form a ring with a methylenedioxy group;

heteroaryl; heteroaryl substituted by 1 to 4 substituents selected from the group consisting of halogen, $C_1$–$C_6$ alkoxy, $C_1$–$C_6$ alkyl, ($C_1$–$C_6$)alkylamino, di-(($C_1$–$C_6$) alkyl)amino, —$OCF_3$, —$NO_2$, hydroxy($C_1$–$C_6$)alkyl, —CHO and phenyl; and heteroaryl wherein adjacent carbon atoms form a ring with a $C_3$–$C_5$ alkylene group or a methylenedioxy group;

$R^4$ and $R^5$ are independently selected from the group consisting of H, $C_1$–$C_6$ alkyl, phenyl, benzyl and $C_3$–$C_6$ cycloalkyl, or $R^4$ and $R^5$ together are —$(CH_2)_4$—, —$(CH_2)_5$— or —$(CH_2)_2NR^7$—$(CH_2)_2$— and form a ring with the nitrogen to which they are attached;

$R^6$ is independently selected from the group consisting of H, $C_1$–$C_6$ alkyl or phenyl;

$R^7$ is H or ($C_1$–$C_6$)alkyl;

$R^8$, $R^{10}$ and $R^{11}$ are independently selected from the group consisting of $R^1$ and —$OR^1$, provided that when the optional double bond is present, $R^{10}$ is absent, and when ring Q is aromatic, $R^{10}$ and $R^{11}$ are absent;

$R^9$ is H, OH, $C_1$–$C_6$ alkoxy, halogen or halo($C_1$–$C_6$)alkyl;

B is —$(CH_2)_{n3}$—, —$CH_2$—O—, —$CH_2S$—, —$CH_2$—$NR^6$—, —$C(O)NR^6$—, —$NR^6C(O)$—,

cis or trans —$(CH_2)_{n4}CR^{12}$=$CR^{12a}(CH_2))_{n5}$ or —$(CH_2))_{n4}C$≡$C(CH_2)_{n5}$—, wherein $n_3$ is 0–5, $n_4$ and $n_5$ are independently 0–2, and $R^{12}$ and $R^{12a}$ are independently selected from the group consisting of H, $C_1$–$C_6$ alkyl and halogen;

X is —O— or —$NR^6$— when the double dotted line represents a single bond, or X is —OH or —$NHR^{20}$ when the bond is absent;

Y is=O, =S, (H, H), (H, OH) or (H, $C_1$–$C_6$ alkoxy) when the double dotted line represents a single bond, or when the bond is absent, Y is =O, (H, H), (H, OH), (H, SH) or (H, $C_1$–$C_6$ alkoxy);

$R^{15}$ is absent when the double dotted line represents a single bond and is H, $C_1$–$C_6$ alkyl, —$NR^{18}R^{19}$, or —$OR^{17}$ when the bond is absent; or Y is

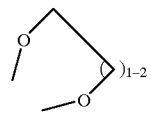

or

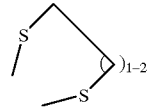

and $R^{15}$ is H or $C_1$–$C_6$ alkyl;

$R^{16}$ and $R^{16a}$ are independently selected from the group consisting of $C_1$–$C_6$ lower alkyl, phenyl or benzyl;

$R^{17}$, $R^{18}$ and $R^{19}$ are independently selected from the group consisting of H, $C_1$–$C_6$ alkyl, phenyl, benzyl;

$R^{20}$ is H, $C_1$–$C_6$ alkyl, phenyl, benzyl, —$C(O)R^6$ or —$SO_2R^6$;

$R^{21}$ is 1 to 3 substutuents independently selected from the group consisting of —$CF_3$, —$OCF_3$, halogen, —$NO_2$, $C_1$–$C_6$ alkyl, $C_1$–$C_6$alkoxy, ($C_1$–$C_6$)alkylamino, di-(($C_1$–$C_6$)alkyl)amino, amino($C_1$–$C_6$)alkyl, ($C_1$–$C_6$)-alkylamino($C_1$–$C_6$)alkyl, di-(($C_1$–$C_6$)alkyl)-amino ($C_1$–$C_6$)alkyl, hydroxy($C_1$–$C_6$)alkyl, —$COOR^{17}$, —$COR^{17}$, —$NHCOR^{16}$, —$NHSO_2R^{16}$ and —$NHSO_2CH_2CF_3$;

Z is —$CH_2$—, —O—, —$S(O)_{0-2}$—, —$NR^{22}$—, —$C(O)$—, —$C(=NOR^{17})$— or —$C(R^{13}R^{14})$—, wherein $R^{13}$ and $R^{14}$, together with the carbon to which they are attached, form a spirocycloalkyl group of 3 to 6 carbons, or a spiroheterocycloalkyl group of 3 to 6 members, comprised of 2 to 5 carbon atoms and 1 or 2 heteroatoms selected from the group consisting of O, S and N; and $R^{22}$ is H, $C_1$–$C_6$ alkyl, phenyl, benzyl, —$COR^{16}$ or —$CONR^{18}R^{19}$.

One group of preferred compounds is that of the formula IA

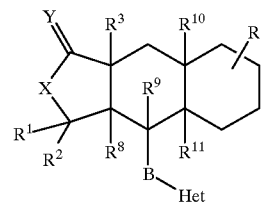

wherein X, Y, R, $R^1$, $R^2$, $R^3$, $R^8$, $R^9$, $R^{10}$, $R^{11}$, B and Het are as defined above.

A second group of preferred compounds is that of the formula IB

IB

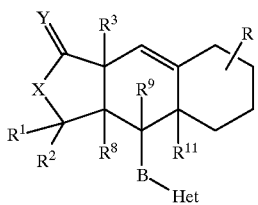

wherein X, Y, R, $R^1$, $R^2$, $R^3$, $R^8$, $R^9$, $R^{11}$, B and Het are as defined above.

A third group of preferred compounds is that of the formula IC

IC

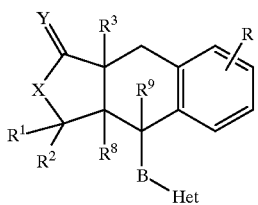

wherein X, Y, R, $R^1$, $R^2$, $R^3$, $R^8$, $R^9$, B and Het are as defined above.

$R^2$, $R^8$, $R^{10}$ and $R^{11}$ are each preferably hydrogen. $R^3$ preferably is hydrogen or lower alkyl. The variable n is preferably zero. $R^9$ is preferably H, OH or alkoxy. $R^1$ is preferably $C_1$–$C_6$ alkyl, more preferably methyl. The double dotted line preferably represents a single bond; X is preferably —O— and Y is preferably =O or (H, —OH). Z is preferably —$CH_2$—, —C(O)— or —C(=$NOR^{17}$)—. The ring Q is preferably R-substituted cyclohexyl or R-substituted phenyl. R is preferably hydrogen, fluorine, hydroxy, alkoxy or alkyl. B is preferably trans —CH=CH—. Het is preferably pyridyl, substituted pyridyl, quinolyl or substituted quinolyl. Preferred substituents (W) on Het are aryl, substituted aryl, heteroaryl or alkyl. More preferred are compounds wherein Het is 2-pyridyl substituted in the 5-position by aryl, substituted aryl, heteroaryl or alkyl, or 2-pyridyl substituted in the 6-position by alkyl.

Thrombin receptor antagonist compounds of the present invention have anti-thrombotic, anti-platelet aggregation, antiatherosclerotic, antirestenotic and anti-coagulant activity. Thrombosis-related diseases treated by the compounds of this invention are thrombosis, atherosclerosis, restenosis, hypertension, angina pectoris, arrhythmia, heart failure, myocardial infarction, glomerulonephritis, thrombotic and thromboembolytic stroke, peripheral vascular diseases, other cardiovascular diseases, cerebral ischemia, inflammatory disorders and cancer, as well as other disorders in which thrombin and its receptor play a pathological role.

Therefore, this invention also relates to the use of a compound of formula I as an antithrombotic, anti-platelet aggregation, anticoagulant or anticancer agent in a mammal in need of such treatment.

In another aspect, the invention relates to a pharmaceutical composition comprising a compound of formula I in a pharmaceutically acceptable carrier.

DETAILED DESCRIPTION

Unless otherwise defined, the term "alkyl" or "lower alkyl" means straight or branched alkyl chains of 1 to 6 carbon atoms and "alkoxy" similarly refers to alkoxy groups having 1 to 6 carbon atoms.

Fluoroalkyl, difluoroalkyl and trifluoroalkyl mean alkyl chains wherein the terminal carbon is substituted by 1, 2 or 3 fluoroatoms, e.g., —$CF_3$, —$CH_2CF_3$, —$CH_2CHF_2$ or —$CH_2CH_2F$. Haloalkyl means an alkyl chain substituted by 1 to 3 halo atoms.

"Alkenyl" means straight or branched carbon chains of 1 to 6 carbon atoms having one or more double bonds in the chain, conjugated or unconjugated. Similarly, "alkynyl" means straight or branched carbon chains of 1 to 6 carbon atoms having one or more triple bonds in the chain. Where an alkyl, alkenyl or alkynyl chain joins two other variables and is therefore bivalent, the terms alkylene, alkenylene and alkynylene are used.

"Cycloalkyl" means a saturated carbon ring of 3 to 6 carbon atoms, while "cycloalkylene" refers to a corresponding bivalent ring, wherein the points of attachment to other groups include all positional and stereoisomers.

"Heterocycloalkyl" as a substituent on Het means saturated rings of 4 to 7 atoms comprised of 3 to 4 carbon atoms and 1 to 3 heteroatoms selected from the group consisting of —O—, —S— and —$NR^7$— joined to the rest of the molecule through a carbon atom. Examples of heterocycloalkyl groups are 2-azetidinyl, 2-pyrrolidinyl, tetrahydrothiophen-2-yl, tetrahydro-2-furanyl, 4-piperidinyl, 2-piperazinyl, tetrahydro-4-pyranyl, 2-morpholinyl and 2-thiomorpholinyl.

"Halogen" refers to fluorine, chlorine, bromine or iodine radicals.

When $R^4$ and $R^5$ join to form a ring with the nitrogen to which they are attached, the rings formed are 1-pyrrolidinyl, 1-piperidinyl and 1-piperazinyl, wherein the piperazinyl ring may also be substituted at the 4-position nitrogen by a group $R^7$.

"Dihydroxy($C_1$–$C_6$)alkyl" refers to an alkyl chain substituted by two hydroxy groups on two different carbon atoms.

"Aryl" means phenyl, naphthyl, indenyl, tetrahydronaphthyl or indanyl.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included, as well as compounds wherein a ring nitrogen is substituted by a $C_1$–$C_4$ alkyl group to form a quaternary amine. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1, 5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 1-pyridyl, 2-pyridyl, 3-pyridyl and 4-pyridyl. W-substituted heteroaryl refers to such groups wherein substitutable ring carbon atoms have a substituent as defined above, or where adjacent carbon atoms form a ring with an alkylene group or a methylenedioxy group.

The term "Het" is exemplified by the single ring, bicyclic and benzofused heteroaryl groups as defined immediately above, as well as tricyclic groups such as benzoquinolinyl (e.g., 1,4 or 7,8) or phenanthrolinyl (e.g., 1,7; 1,10; or 4,7). Het groups are joined to group B by a carbon ring member, e.g., Het is 2-pyridyl, 3-pyridyl or 2-quinolyl.

Examples of heteroaryl groups wherein adjacent carbon atoms form a ring with an alkylene group are 2,3-cyclopentenopyridine, 2,3-cyclohexenopyridine and 2,3-cycloheptenopyridine.

The term "optional double bond" refers to the bond shown by the single dotted line in the middle ring of the structure shown for formula I. The term "optional single bond" refers to the bond shown by the double dotted line between X and the carbon to which Y and $R^{15}$ are attached in the structure of formula I. Compounds wherein the bond is absent are shown, for example, in Example 6.

The above statements, wherein, for example, $R^4$ and $R^5$ are said to be independently selected from a group of substituents, means that $R^4$ and $R^5$ are independently selected, but also that where an $R^4$ or $R^5$ variable occurs more than once in a molecule, those occurrences are independently selected. Those skilled in the art will recognize that the size and nature of the substituent(s) will affect the number of substituents which can be present.

Compounds of the invention have at least one asymmetrical carbon atom and therefore all isomers, including diastereomers and rotational isomers are contemplated as being part of this invention. The invention includes (+)- and (−)-isomers in both pure form and in admixture, including racemic mixtures. Isomers can be prepared using conventional techniques, either by reacting optically pure or optically enriched starting materials or by separating isomers of a compound of formula I.

Typical preferred compounds of the present invention wherein Q is a saturated ring have the following stereochemistry:

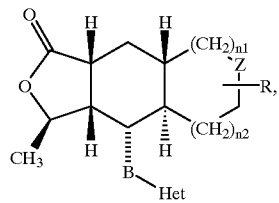

with compounds having that absolute stereochemistry being more preferred. Typical preferred compounds of the present invention wherein Q is an aromatic ring have the following stereochemistry, wherein Q is exemplified as a phenyl ring:

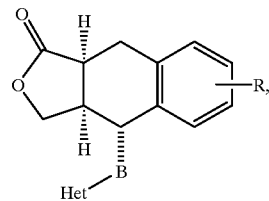

with compounds having that absolute stereochemistry being more preferred.

Those skilled in the art will appreciate that for some compounds of formula I, one isomer will show greater pharmacological activity than other isomers.

Compounds of the invention with a basic group can form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salt is prepared by contacting the free base form with a sufficient amount of the desired acid to produce a salt. The free base form may be regenerated by treating the salt with a suitable dilute aqueous base solution such as dilute aqueous sodium bicarbonate. The free base form differs from its respective salt form somewhat in certain physical properties, such as solubility in polar solvents, but the salt is otherwise equivalent to its respective free base forms for purposes of the invention.

Certain compounds of the invention are acidic (e.g., those compounds which possess a carboxyl group). These compounds form pharmaceutically acceptable salts with inorganic and organic bases. Examples of such salts are the sodium, potassium, calcium, aluminum, lithium, gold and silver salts. Also included are salts formed with pharmaceutically acceptable amines such as ammonia, alkyl amines, hydroxyalkylamines, N-methylglucamine and the like.

Compounds of the present invention are generally prepared by processes known in the art, for example by the processes described below.

In Scheme 1, a process is shown for preparing compounds of formula I wherein n is 0, the optional double bond is not present, Q forms a cyclohexyl ring, the single bond is present between X and the carbon to which Y is attached, X is —O—, Y is =O, B is —CH=CH—, Het is W-substituted pyridyl, $R^2$ is methyl, and $R^1$, $R^3$, $R^8$, $R^9$, $R^{10}$ and $R^{11}$ are each hydrogen. However, a similar process may be used to prepare compounds comprising other optionally substituted Het groups. Those skilled in the art will also recognize that the process is equally applicable to preparing optically active or racemic compounds.

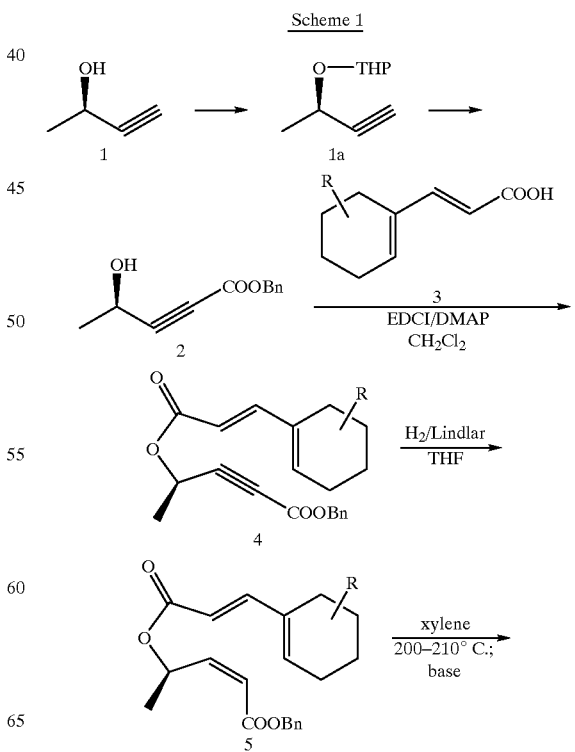

Scheme 1

-continued

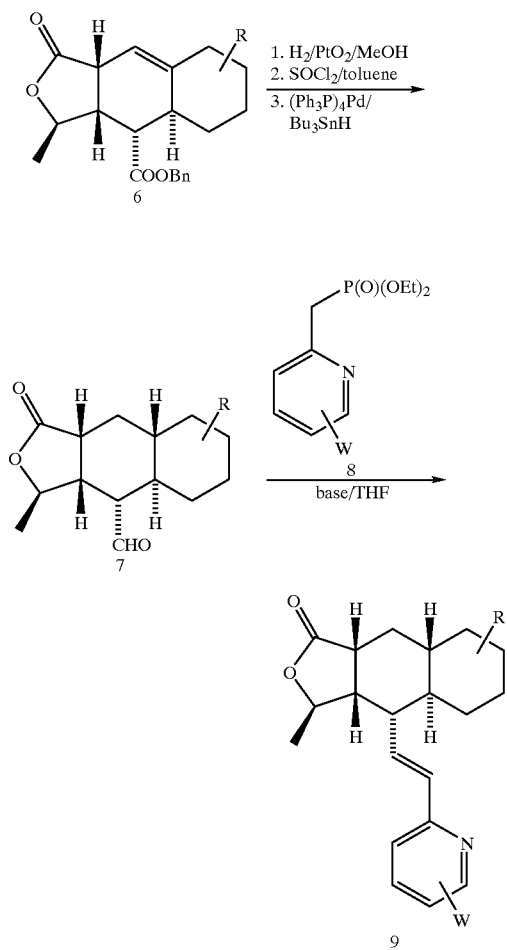

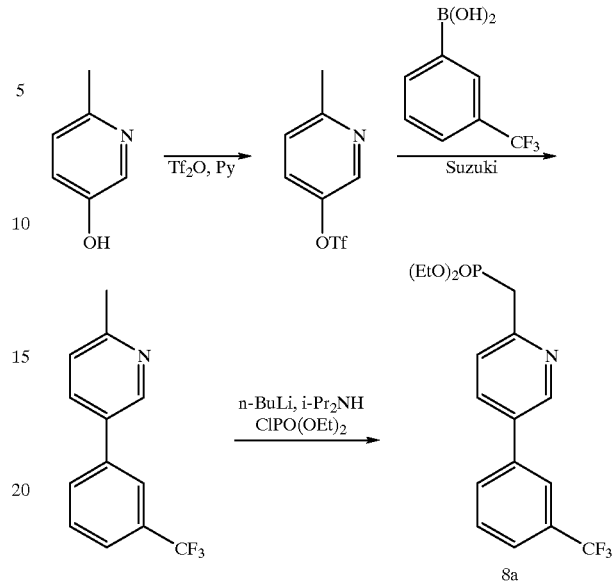

Commercially available (R)-3-butyn-2-ol is O-protected as the tetrahydropyranyl ether by treatment with dihydropyran in the presence of catalytic amounts of para-toluenesulfonic acid to give intermediate 1a. Treatment of a solution of 1a in THF with n-BuLi at −78° C. followed by quenching with benzylchloroformate and subsequent deprotection gives intermediate 2 which is esterified with dienoic acid 3 using standard conditions to yield the ester 4. Selective reduction of the triple bond of 4 using Lindlar catalyst under hydrogen gives the intermediate 5, which upon thermal cyclization between 200–210° C. followed by base treatment gives the tricyclic intermediate 6. The ester 6 is subjected to hydrogenation in the presence of platinum oxide to generate the intermediate saturated carboxylic acid, treatment of which with $SOCl_2$ gives the corresponding acid chloride which is converted to the tricyclic aldehyde 7 by reduction using tributyltin hydride in the presence of Pd(0). Condensation of the anion generated from phosphonate 8 with aldehyde 7 in THF gives the alkene 9 (final product).

Intermediates of formula 8 wherein W is aryl or $R^{21}$-aryl can be prepared by a process similar to that described immediately below for preparing the trifluoromethy-phenyl-substituted compound, 8a.

Commercially available hydroxypyridine derivative is converted to the corresponding triflate using triflic anhydride, which is then coupled with commercially available boronic acid in the presence of Pd(0) under Suzuki conditions. The resulting product is converted to the phosphonate by treatment with tert-butyllithium followed by quenching with diethylchlorophosphonate.

Alternatively, compounds of formula 9 wherein W is optionally substituted aryl can be prepared from compounds of formula 9 wherein W is —OH using a triflate intermediate. For example, 3-hydroxy-6-methylpyridine is treated with triisopropylsilyl chloride, and the resultant hydroxy-protected compound is converted to the phosphonate as described above for preparing intermediate 8. The triisopropylsilyl-protected intermediate is then reacted with tricyclic intermediate 7 and the protecting group is removed under standard conditions. The resultant compound of formula 9 wherein W is OH is then treated with triflic anhydride at room temperature in a solvent such as $CH_2Cl_2$; the triflate is then reacted with an optionally substituted arylboronic acid, e.g., optionally substituted phenylboronic acid, in a solvent such as toluene, in the presence of $Pd(PPh_3)_4$ and a base such a $K_2CO_3$ at elevated temperatures and under an inert atmosphere.

Compounds of formula 9 wherein W is a substituted hydroxy group (e.g., benzyloxy) can be prepared from compounds of formula 9 wherein W is hydroxy by refluxing in a suitable solvent such as acetone with a halogen-substituted compound such as optionally substituted benzyl bromide in the presence of a base such as $K_2CO_3$.

Compounds of formula I wherein Het is substituted by W through a carbon atom (e.g., wherein W is alkyl, alkenyl or arylalkyl) or a nitrogen atom (i.e., —$NR^4R^5$) can be prepared using a compound of formula I wherein W is chloroalkyl as an intermediate. Compounds of formula I wherein W is a polar group such as hydroxy alkyl, dihydroxyalkyl, —COOH, dimethylamino and —COH can be prepared as shown in Scheme 1B, wherein the starting material is a compound of formula I wherein W is alkenyl. The following Schemes 1A and 1B show well-known reaction conditions for preparing various W-substituted compounds wherein Q is cyclohexyl, X is —O—, Y is =O, $R^{15}$ is absent, $R^1$ is methyl, $R^2$, $R^3$, $R^9$, $R^{10}$ and $R^{11}$ are each H, B is —CH=CH—, and Het is 2-pyridyl.
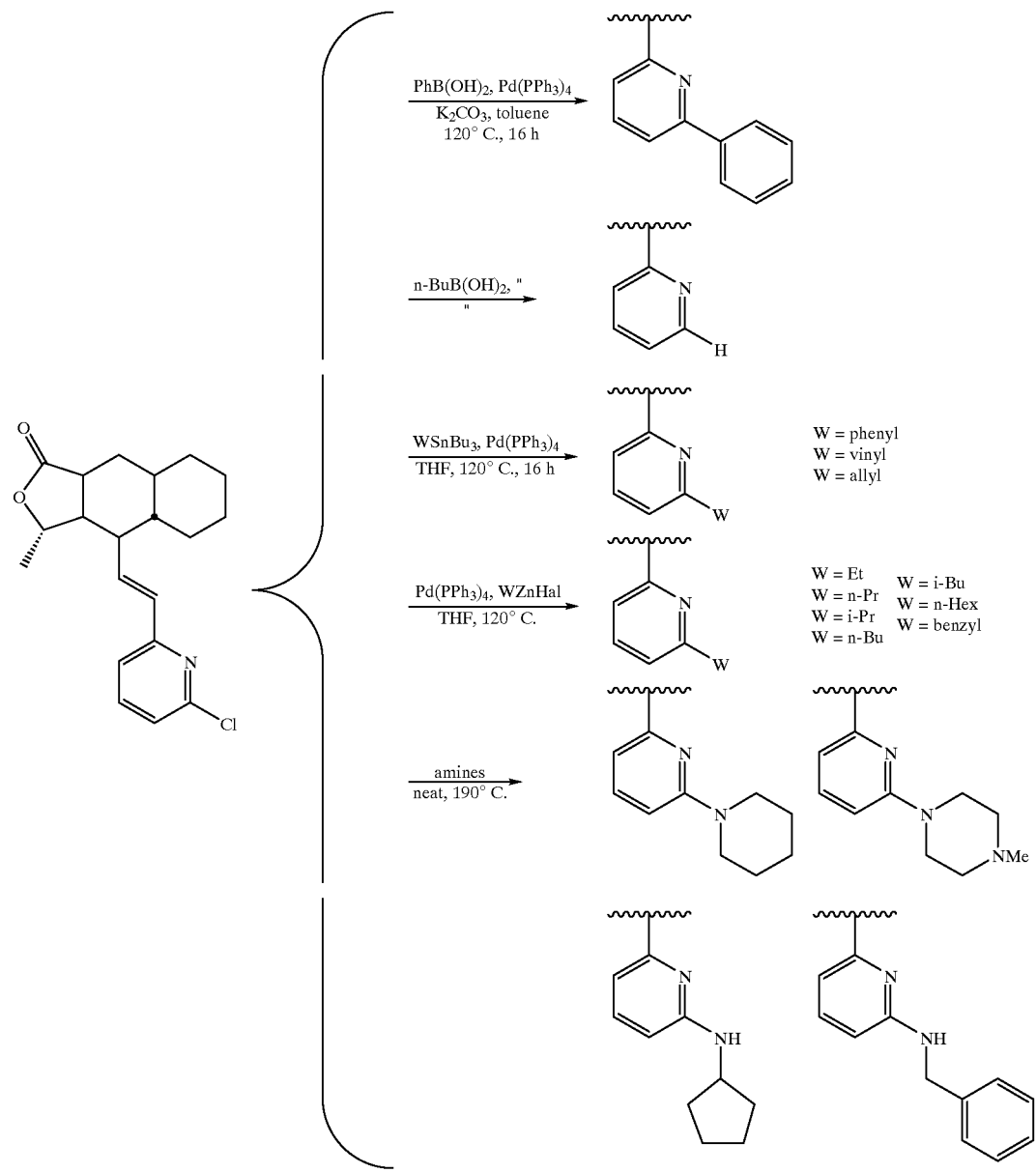
Scheme 1A

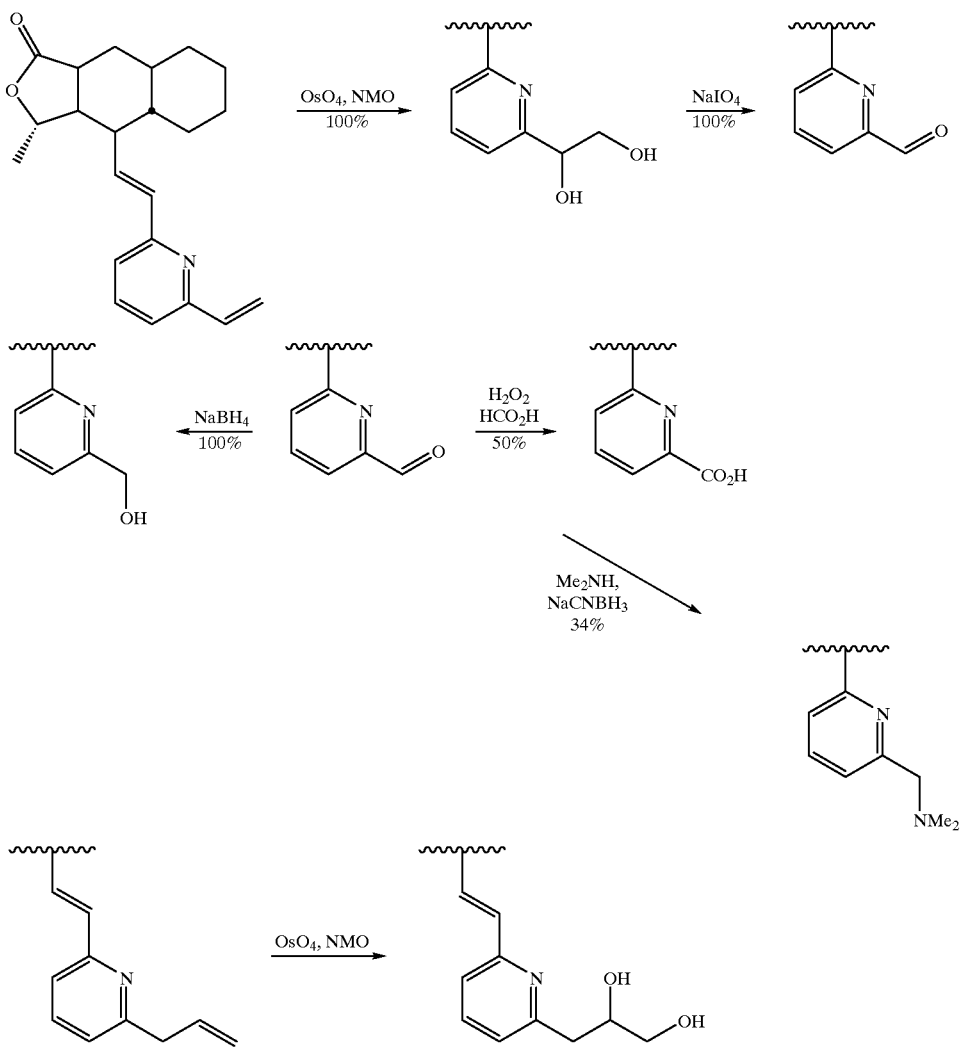

Those skilled in the art will appreciate that similar reactions to those described in the above tables may be carried out on other compounds of formula I as long as substituents present would not be susceptible to the reaction conditions described.

Compounds of formula I wherein Q is non-aromatic, the optional single bond (represented by the double dotted line) is absent, X is OH, Y is OH, $R^{15}$ is H and the remaining variables are as defined above can be prepared by treating corresponding compounds wherein the optional single bond is present, X is —O—, Y is =O and $R^{15}$ is absent, with a reducing agent such as LAH.

Compounds of formula I wherein the optional single bond is present, X is —O—, Y is (H, OH), $R^{15}$ is absent and the remaining variables are as defined above can be prepared by treating corresponding compounds wherein the optional single bond is present, X is —O—, Y is =O and $R^{15}$ is absent, with a reagent such as DIBAL. The resultant compounds wherein Y is (H, OH) can be converted to the corresponding compounds wherein Y is (H, alkoxy) by reacting the hydroxy compound with an appropriate alkanol in the presence of a reagent such as $BF_3 \cdot OEt_2$. A compound wherein Y is (H, OH) can also be converted to the corresonding compound wherein Y is (H, H) by treating the hydroxy compound with $BF_3 \cdot OEt_2$ and $Et_3SiH$ in an inert solvent such as $CH_2Cl_2$ at low temperatures.

Compounds of formula I wherein $R^9$ is hydrogen can be converted to the corresponding compound wherein $R^9$ is hydroxy by heating with an oxidizing agent such as $SeO_2$.

In Scheme 2, a process is shown for preparing compounds of formula I wherein n is 0, the optional double bond is present, Q forms a cyclohexyl ring, X is —O—, Y is =O, $R^2$, $R^3$, $R^8$, $R^9$ and $R^{11}$ are each hydrogen, $R^1$ is methyl, $R^{10}$ is absent, B is —CH=CH—, and Het is W-substitued pyridyl. However, a similar process may be used to prepare compounds comprising other optionally substituted Het groups.

Scheme 2

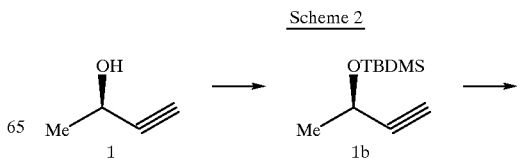

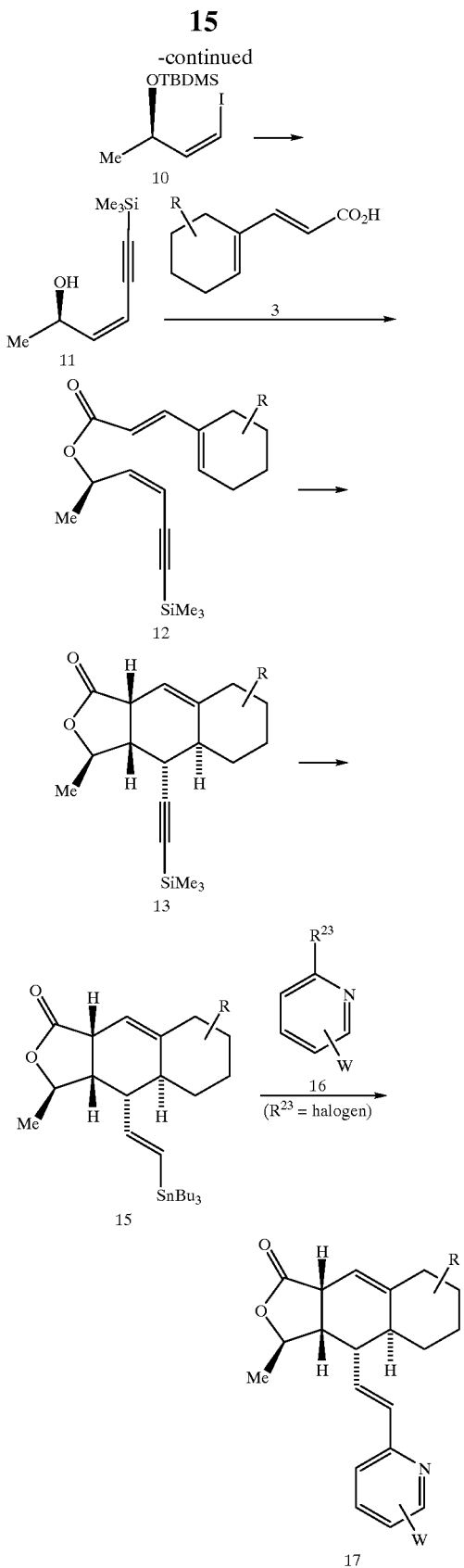

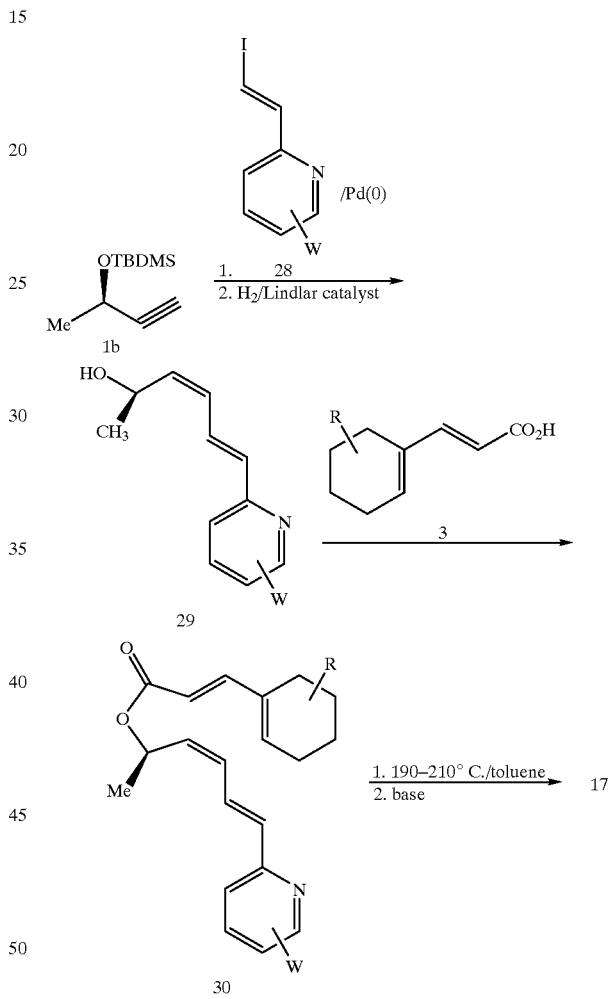

The alcohol 1 is O-protected as the TBDMS ether by treatment with TBDMS chloride. The anion generated from 1b is quenched with a solution of iodine to give the corresponding acetylenic iodide, which upon reduction using di(cyclohexyl)borane gives the cis-vinyl iodide 10. Coupling of vinyl iodide 10 with trimethylsilylacetylene in the presence of Cu(I) and Pd(0) gives the intermediate 11 after removal of the protecting group using trifluoroacetic acid in CH₃OH. Esterification of 11 with acid 3 gives the intermediate ester 12, which upon thermal cyclization at 185–195° C. gives the tricyclic precursor 13 after a brief treatment with DBU. Desilylation of acetylenic derivative 13 followed by hydrostannylation using tributyltinhydride in the presence of AIBN gives the vinyistannane derivative 15, which is coupled with halopyridine derivative 16 to give the final product 17.

Scheme 2A offers an alternative procedure:

Palladuium-mediated coupling of acetylene 1b with transiodovinylpyridine 28 followed by selective reduction of the triple bond gives the intermediate dienoic alcohol 29 which is esterified with the dienoic acid 3 to give 30. Thermal cyclization of 30 at 190–210° C. followed by base treatment gives 17. Intermediate 28 is prepared from (2-chloro-6-methyl)pyridine by coupling with (trimethylsilyl)acetylene in the presence of palladium, followed by deprotection of the silyl group using fluoride anion and treatment of the isolated product with tributyltin hydride foillowed by iodine.

In Scheme 3, a process is shown for preparing compounds of formula I wherein n is 0, the optional double bond is not present, Q forms a phenyl ring, X is —O—, Y is =O, $R^1$, $R^2$, $R^3$, $R^8$ and $R^9$ are each hydrogen, $R^{10}$ and $R^{11}$ are absent, B is —CH=CH—, and Het is methoxy-substitued quinolyl. However, a similar process may be used to prepare compounds comprising other optionally substituted Het groups.

Scheme 3

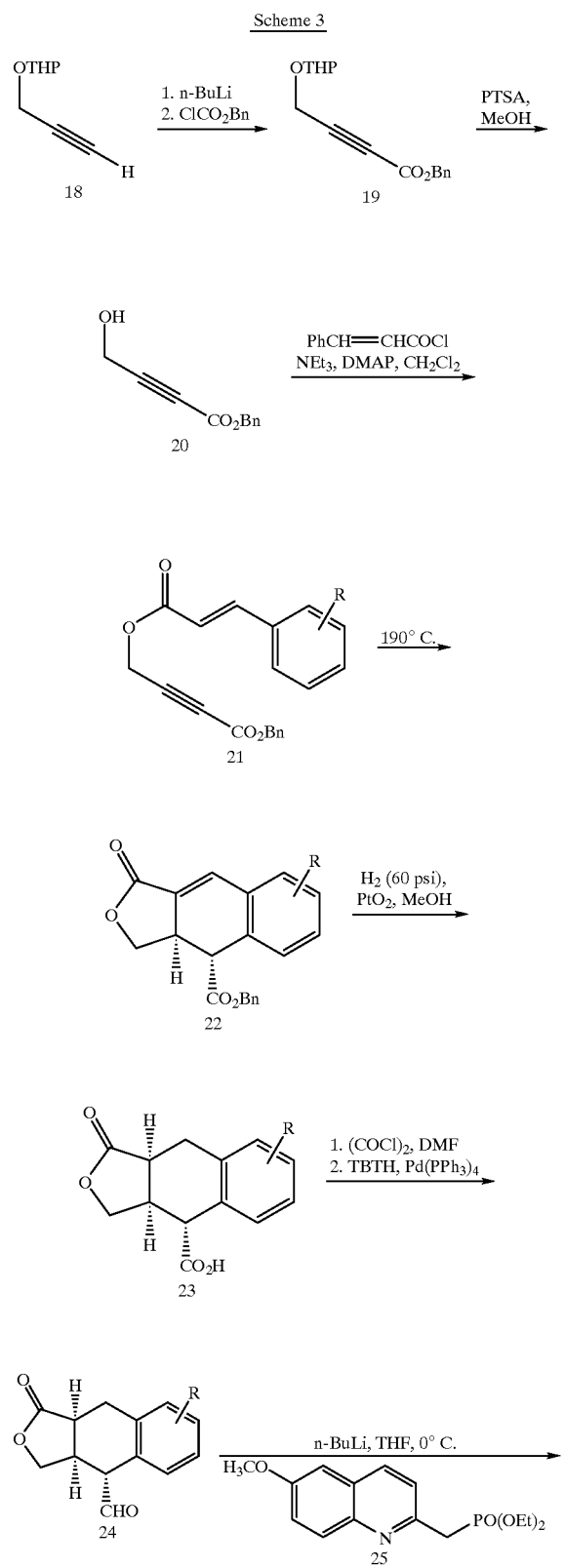

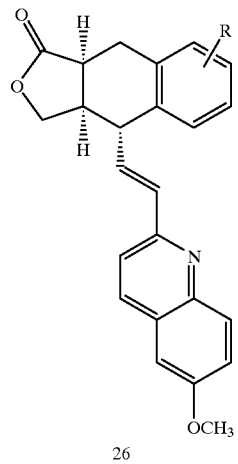

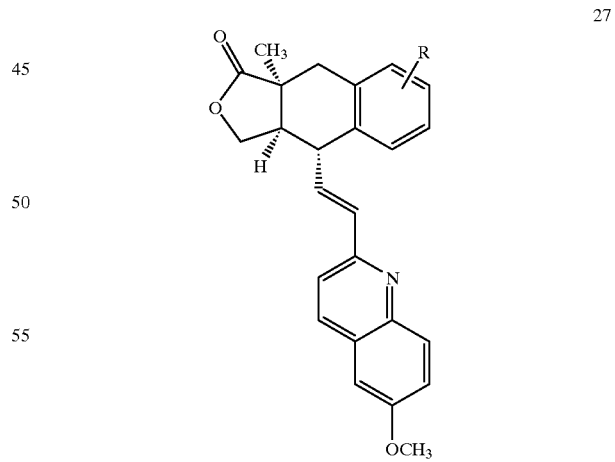

Commercially available acetylenic derivative 18 is converted to the corresponding ester 19 by treatment with n-BuLi in THF followed by quenching with benzylchloroformate. Removal of the THP group followed by esterification using trans-cinnamyl chloride under standard conditions gives the ester 21 which, upon thermal cyclization at 190° C., gives the tricyclic ester 22. Hydrogenation of 22 over platinum oxide gives the carboxylic acid 23 which is converted to the corresponding acid chloride under standard conditions. Reduction of the acid chloride generated from 23 using Pd(0) and tributyltin hydride gives the aldehyde 24 which is condensed with the anion generated from the phosphonate 25 to give the final product, 26.

Compounds wherein $R^3$ is alkyl can be prepared from the corresponding compounds wherein $R^3$ is hydrogen. For example, treatment of compound 26 with LDA followed by $CH_3I$ results in the preparation of the corresponding compound 27 wherein $R^3$ is methyl:

Amide, lactam and imide derivatives of compounds of formula I wherein Q is an aromatic ring can be prepared from compounds wherein X is —O— and Y is =O using the following procedures showing partial structural formulas:

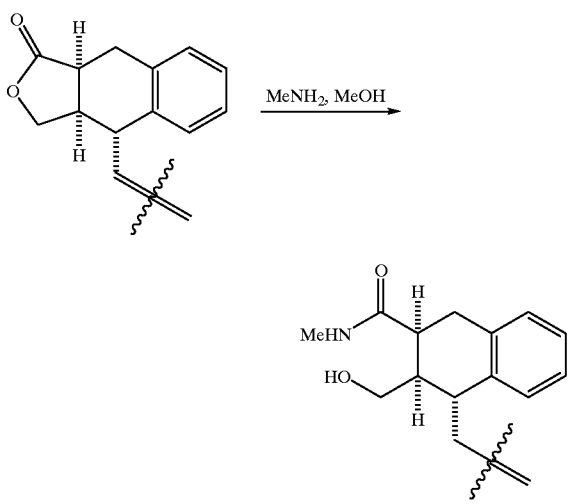

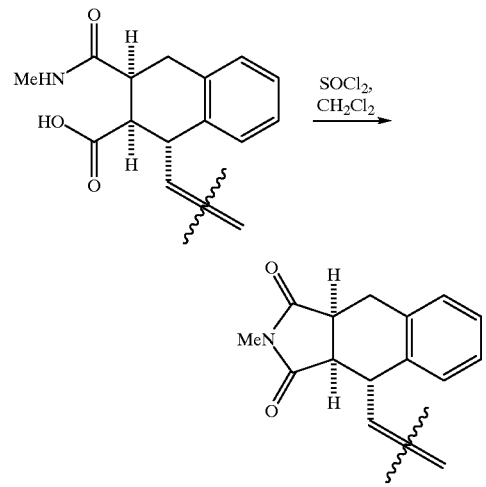

The lactone is treated with an amine to form the ring-opened amide.

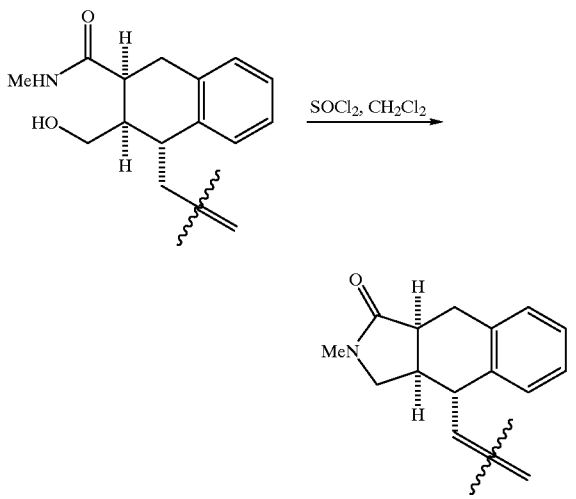

The amide is treated with a reagent such as SOCl₂ to cyclize the amide to the lactam.

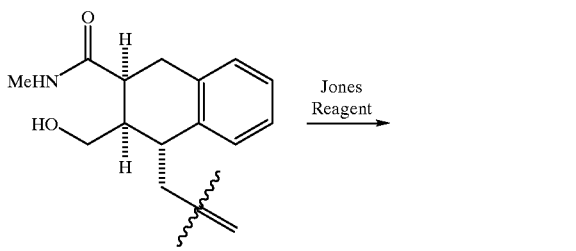

The hydroxy-substituted portion of the amide can be converted to a carboxylic acid by treatment with a reagent such as Jones Reagent, and the resultant product is cyclized to form the imide in the same manner as for the lactam.

In Scheme 4, a process is shown for preparing compounds of formula I wherein n is 0, the optional double bond is not present, Q is a cyclohexyl ring substituted in the 6-position by ethylenedioxy (i.e., Z is —C(R$^{13}$R$^{14}$)), X is —O—, Y is =O, R$^1$, R$^3$, R$^8$, R$^9$, R$^{10}$ and R$^{11}$ are each hydrogen, R$^2$ is methyl, R$^{15}$ is absent, B is —CH=CH—, Het is pyridyl and W is CF₃-phenyl. However, a similar process may be used to prepare compounds comprising other optionally substituted Het groups.

Scheme 4

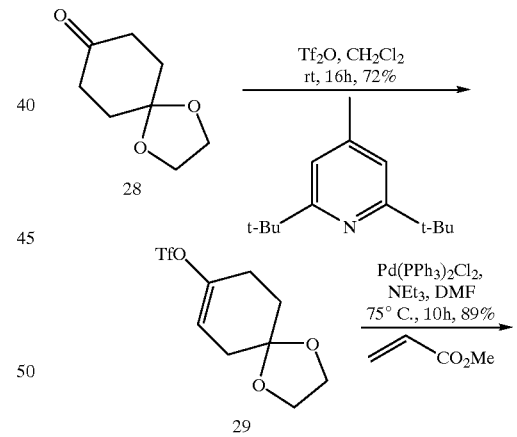

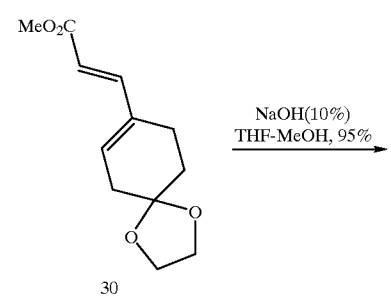

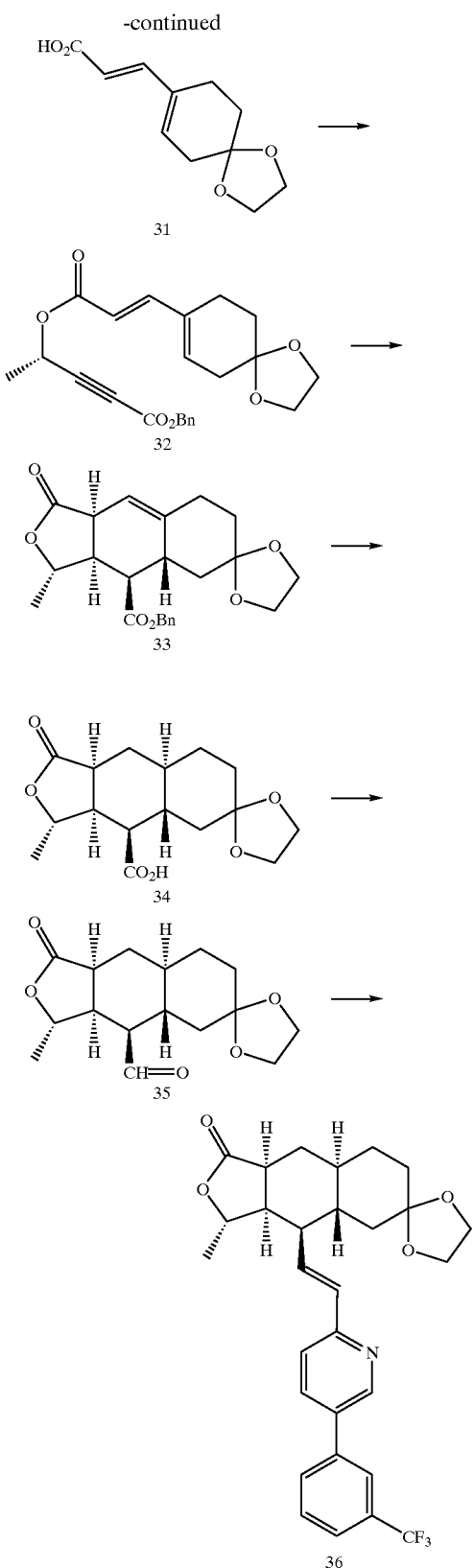

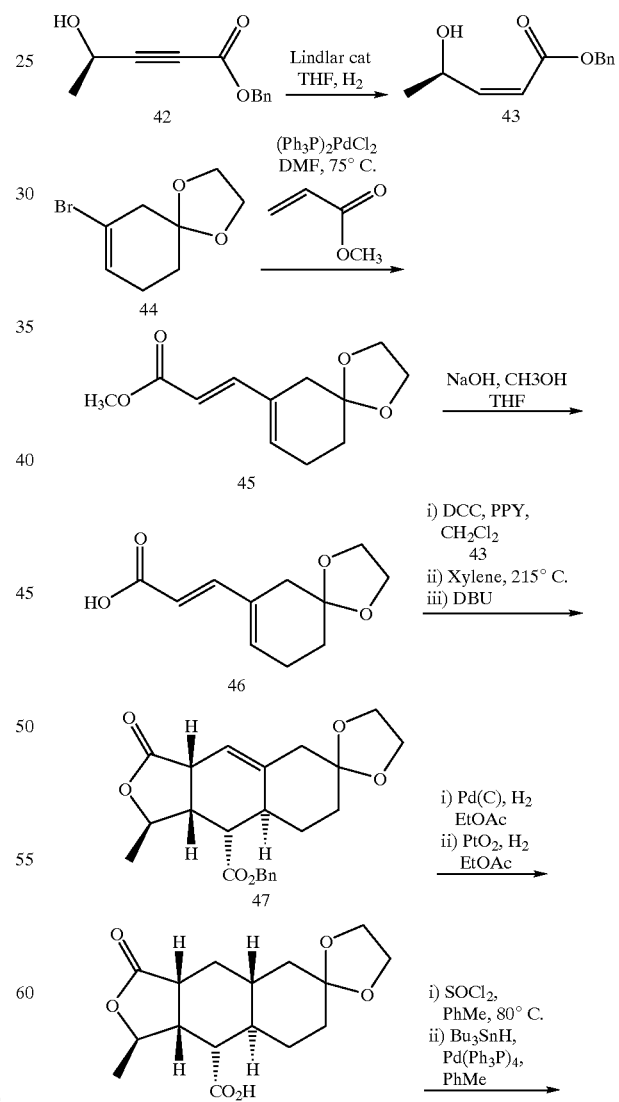

converted to compound 30 by treatment with methyl acrylate in a solvent such as DMF, in the presence of a base such as Et₃N and a catalyst such as Pd(PPh₃)₂Cl₂, and 30 is converted to the corresponding acid, 31, by standard methods, e.g. by treatment with a base such as NaOH. Acid 31 is then reacted with racemic 2 and cyclized as described in Scheme 1 to obtain the product 36 as a racemic mixture.

A ketal such as compound 36 can be converted to the corresponding ketone by treatment with an acid such as HCl. The ketone, in turn, can be reduced to the corresponding hydroxy compound be treatment with a reagent such as NaBH₄ or K-Selectride®.

In Scheme 4A, a process is shown for preparing compounds similar to those in Scheme 4, but wherein Z is ethylenedioxy and is in the 7-position of the cyclohexyl ring.

A solution of 1,4-cyclohexanedione mono-ethylene ketal, 28, and 2,6-di-t-butyl-4-methylpyridine is treated with triflic anhydride to obtain the enol triflate, 29. Compound 29 is -continued

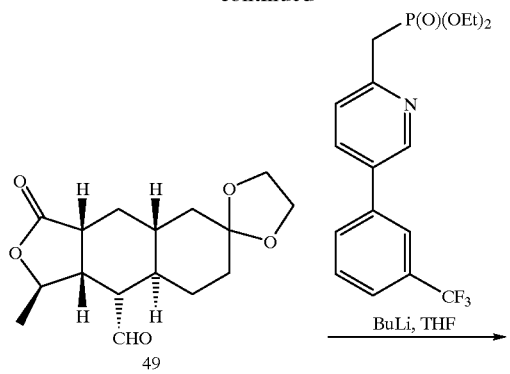

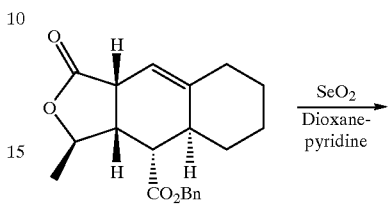

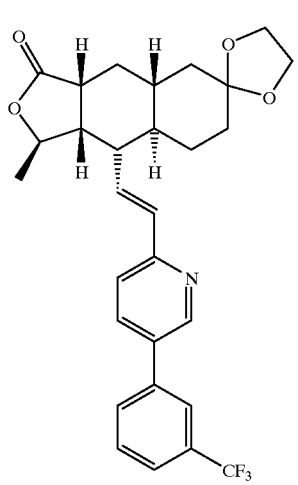

A solution of the ketal, 44, is treated with methyl acrylate in a solvent such as DMF, in the presence of a base such as Et$_3$N and a catalyst such as Pd(PPh$_3$)$_2$Cl$_2$, and the resultant ester, 45, is converted to the corresponding acid, 46, by standard methods, e.g. by treatment with a base such as NaOH. Acid 46 is then reacted with compound 43 and cyclized to obtain 47, which is then converted to the corresponding acid by standard methods. The intermediate of 49 is coupled to the —B—Het group using a procedure as described in Scheme 1 to obtain compound 50.

A ketal such as compound 50 can be converted to the corresponding ketone by treatment with an acid such as HCl. The ketone, in turn, can be reduced to the corresponding hydroxy compound be treatment with a reagent such as NaBH$_4$ or K-Selectride®. The ketone can be converted to the corresponding 7-hydroxy-7 methyl compound by treatment with a reagent such as CH$_3$MgBr.

In Scheme 5, a process is shown for preparing compounds of formula I wherein n is 0, the optional double bond is absent, Q forms a cyclohexyl ring, X is —O—, Y is =O, R$^1$, R$^3$, R$^8$, R$^9$, R$^{10}$ and R$^{11}$ are each H, R$^2$ is —CH$_3$, R$^{15}$ is absent, B is —CH=CH—, Het is pyridyl, W is CF$_3$-phenyl, and R is hydroxy. However, a similar process may be used to prepare compounds comprising other optionally substituted Het groups.

Scheme 5

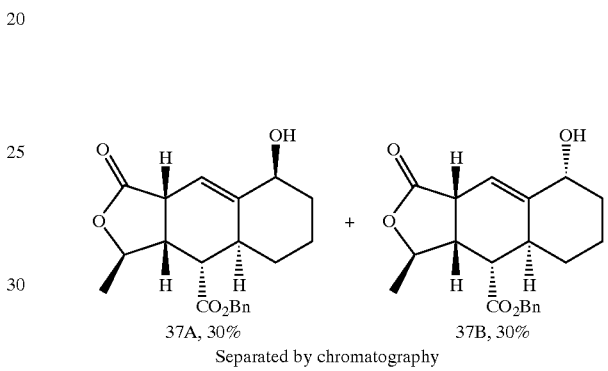

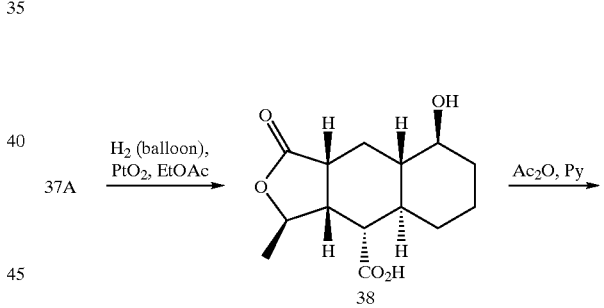

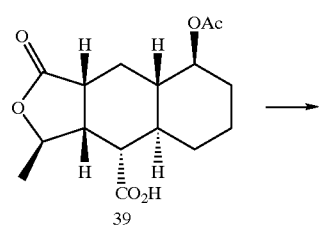

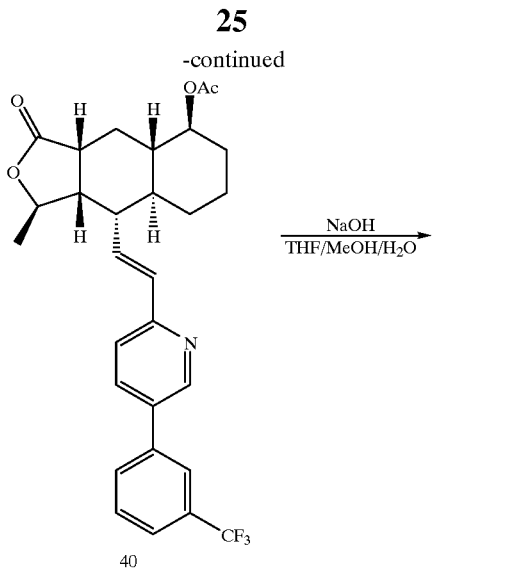

40

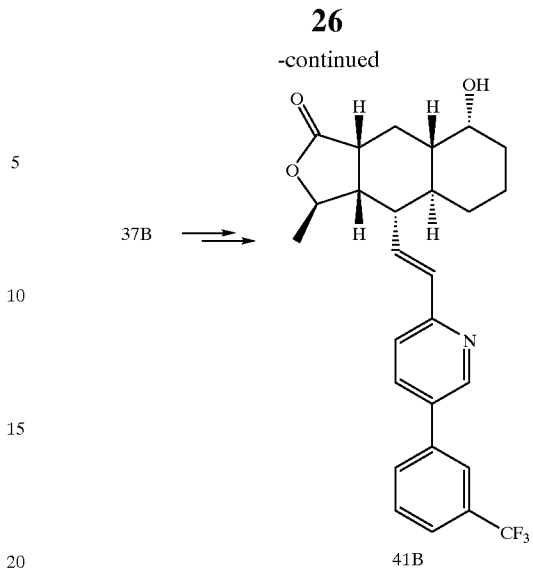

41B

Intermediate 6 from Scheme 1 is oxidized to give intermediate alcohols 37A and 37B. Alcohol 37A is hydrogenated to give 38 which is subsequently converted to acetate 39. Acetate 39 is converted to intermediate 40 in the same fashion as in Scheme 1. Intermediate 40 is hydrolyzed to give 41A. Using a similar procedure, but substituting 37B in the second step, a compound of formula 41 B is obtained.

Compounds of formula I wherein B is —C(O)NH— can be prepared from the acid chloride described above (see Scheme 3) by condensation with the appropriate amine.

Starting materials for the above processes are either commercially available, known in the art, or prepared by procedures well known in the art.

Reactive groups not involved in the above processes can be protected during the reactions with conventional protecting groups which can be removed by standard procedures after the reaction. The following Table A shows some typical protecting groups:

41A

TABLE A

| Group to be Protected | Group to be Protected and Protecting Group |
|---|---|
| —COOH | —COOalkyl, —COObenzyl, —COOphenyl |
| >NH | >NCOalkyl, >NCObenzyl, >NCOphenyl |
| | >NCH₂OCH₂CH₂Si(CH₃)₃, >NC(O)OC(CH₃)₃, |
| | >N-benzyl, >NSi(CH₃)₃, >NSi(CH₃)₂—C(CH₃)₃ |

TABLE A-continued

| Group to be Protected | Group to be Protected and Protecting Group |
|---|---|
| —NH₂ | 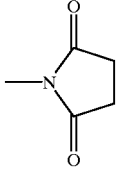 |
| —OH | —OCH₃, —OCH₂OCH₃, —OSi(CH₃)₃, 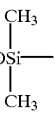 |
| | or —OCH₂phenyl |

The present invention also relates to a pharmaceutical composition comprising a compound of formula I of this invention and a pharmaceutically acceptable carrier. The compounds of formula I can be administered in any conventional oral dosage form such as capsules, tablets, powders, cachets, suspensions or solutions. The formulations and pharmaceutical compositions can be prepared using conventional pharmaceutically acceptable excipients and additives and conventional techniques. Such pharmaceutically acceptable excipients and additives include non-toxic compatible fillers, binders, disintegrants, buffers, preservatives, anti-oxidants, lubricants, flavorings, thickeners, coloring agents, emulsifiers and the like.

The daily dose of a compound of formula I for treatment of a disease or condition cited above is about 0.001 to about 100 mg/kg of body weight per day, preferably about 0.001 to about 10 mg/kg. For an average body weight of 70 kg, the dosage level is therefore from about 0.1 to about 700 mg of drug per day, given in a single dose or 2–4 divided doses. The exact dose, however, is determined by the attending clinician and is dependent on the potency of the compound administered, the age, weight, condition and response of the patient.

Following are examples of preparing compounds of formula I.

EXAMPLE 1

[[2-[(E)-2-(3R, 3aS, 4S, 8aS, 9aR-Dodecahydro-3-methyl-1-oxo-naphtho[2,3-c]furan-4-yl)ethenyl]-6-quinolinyl]oxy]acetic acid

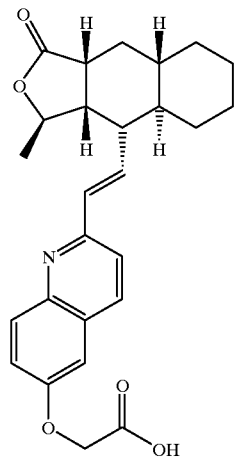

Step 1:

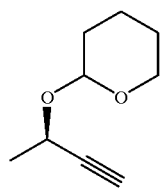

(R)-3-Butyn-2-ol (15 ml, 0.204 mol) and 3,4-dihydro-2H-pyran (26.1 ml, 1 eq) were stirred at 0° C. p-Toluenesulfonic acid(hydrate) (0.38 g, 5 mol %) was added and the mixture stirred for a further 2 h. Ethyl Acetate (EtOAc) (319 ml) and NaHCO₃ (1.6 g) were added and after 1 h the mixture was filtered and concentrated. Chromatography (SiO₂, 19:1 hexane/EtOAc gave 31.49 g (100%) of the desired product as a mixture of diastereomers. ¹H NMR major diastereomer (CDCl₃) δ 1.54 (d, J=7.5 Hz, 3H), 1.55–2.0 (m, 6H), 2.42 (s, 1H), 3.56 (m, 1H), 3.88 (m, 1H), 4.60 (br q, J=7.5 Hz, 1H), 5.00 (t, J=5.0 Hz, 1H).

Step 2:

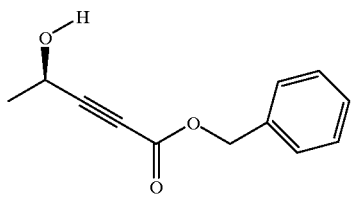

The product of Step 1 (31.49 g, 0.204 mol) was dissolved in THF (1 L) and cooled to −78° C. with stirring. n-Butyllithium (97.8 ml of a 2.5 M solution, 1.2 eq) was added dropwise. After stirring for 20 min, benzyl chloroformate (35.1 ml, 1.2 eq) was added and the reaction stirred at −78° C. for 2 h. The mixture was allowed to warm to room temperature (RT), NH₄Cl solution (saturated) was added and the mixture was extracted with EtOAc. The organic extracts were dried (MgSO₄), concentrated and then dissolved in CH₃OH (2 L), DOWEX 50WX8-100 ion-exchange resin (60 g, prewashed with CH₃OH) was added and the mixture stirred at RT overnight. The mixture was filtered, concentrated and chromatographed (SiO₂, 9:1–4:1 hexane/EtOAc) to give 29.9 g (71%) of the desired product. ¹H NMR (CDCl₃) δ 1.55 (d, J=7.5 Hz, 3H), 4.70 (q, J=7.5 Hz, 1H), 5.27 (s, 2H), 7.44 (br s, 5H).

Step 3:

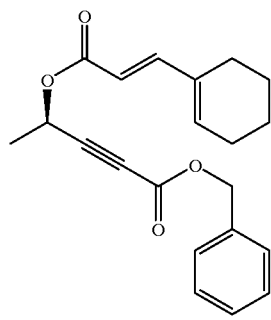

trans-3-(1-Cyclohexenyl)acrylic acid (4.13 g, 0.0273 mol) and 4-pyrrolidinopyridine (0.4 g, 10 mol %) in CH₂Cl₂ (100 ml) were stirred at 0° C. 1,3 Dicyclohexylcarbodiimide (5.63 g, 1 eq) was added and the mixture stirred for 10 min. A solution of the product of Step 2 (5.58 g, 0.0273 mol) in CH₂Cl₂ (40 ml) was added dropwise. The resulting mixture was stirred for 2 hs, filtered, concentrated and chromatographed (SiO₂, 97:3 hexane/EtOAc) to give 5.82 g (63%) of the desired product.

¹H NMR (CDCl₃) δ 1.61 (d, J=7.0 Hz, 3H), 1.66 (m, 2H), 1.74 (m, 2H), 2.18 (m, 2H), 2.27 (m, 2H), 5.25 (s, 2H), 5.67 (m, 1H), 5.80 (d, J=15.0 Hz, 1H), 6.26 (br s,1H), 7.37 (d, J=15.0 Hz, 1H), 7.42 (s, 5H).

Step 4:

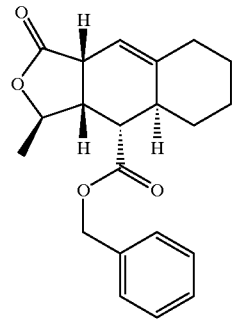

The product of Step 3 (5.82 g, 0.017 mol) and triethylamine (Et₃N) (0.112 mL) were dissolved in THF (32 mL). Lindlar catalyst (0.58 g) was added and the mixture stirred under 1 atm. of hydrogen for 16h. The mixture was filtered, concentrated, dissolved in o-xylene, and degassed under a stream of N₂. The degassed mixture was sealed in a pressure tube and heated at 210° C. for 6 h. After cooling to RT, the xylene was removed under reduced pressure and the resulting mixture chromatographed (SiO₂, 19:1–9:1 hexane/EtOAc) to give 3.81 g (66%) of the desired product. ¹H NMR (CDCl₃) δ 0.94 (m, 1H), 1.20 (d, J=7.0 Hz, 3H), 1.31 (m, 1H), 1.50 (m, 1H), 1.82 (m, 2H), 2.00 (m, 1H), 2.20 (m, 1H), 2.39 (br d, J=15.0 Hz, 1H), 2.51 (m, 1H), 2.62 (m, 1H), 2.73 (m, 1H), 3.35 (m, 1H), 4.53 (m ,1H), 5.22 (AB quartet, J=12.5 Hz, 2H), 5.34 (br s, 1H), 7.42 (br s, 5H).

Step 5:

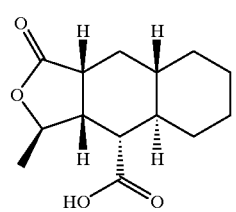

The product of Step 4 (3.81 g, 0.011 mol) was dissolved in CH₃OH (100 ml). Platinum (IV) oxide (0.38 g) was added and the mixture shaken for 16 h under an atmosphere of hydrogen (60 psi). The mixture was filtered, concentrated and recrystallized (CH₂Cl₂/hexanes) to give 2.12 g (75%) of the desired product. ¹H NMR (CDCl₃) δ 0.90–1.0 (m,1H), 1.05–1.20 (m, 2H), 2.21–1.55 (m, 7H), 1.75–1.92 (m, 4H), 1.92–2.00 (m, 1H), 2.52–2.64 (m, 2H), 2.74 (m, 1H), 4.76 (m, 1H).

Step 6:

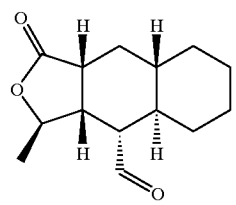

The product of Step 5 (2.3 g, 9.66 mmol) was suspended in toluene (20 ml), SOCl₂ (4 ml) was added and the mixture heated at 80° C. for 16 h. After cooling to RT, the volatiles were removed under reduced pressure and the resulting gum dissolved in fresh toluene (23 ml). Tetrakistriphenylphosphinepalladium(0) (800 mg, 8 mol %) was added and the mixture was cooled to 0° C. Tributyltin hydride (Bu$_3$SnH) (3.24 ml, 1.2 eq) was added dropwise and the mixture stirred for 30 min, after which time TLC showed approximately 66% conversion. Bu$_3$SnH (1.35 mL, 0.5 eq) was added and the mixture stirred for a further hour. The mixture was then chromatographed (SiO$_2$, 4:1 hexanes/EtOAc) to give 1.9 g (88%) of the desired product. $^1$H NMR (CDCl$_3$) δ 0.88–1.05 (m, 1H), 1.10–1.20 (m, 2H), 1.22–1.50 (m, 5H), 1.55–1.70 (m, 2H), 1.75–1.90 (m, 4H), 1.98 (dd, J=12.5, 7.0 Hz, 1H) 2.53 (m, 1H), 2.63 (m, 1H), 2.73 (m, 1H), 4.73 (m, 1H), 9.80 (d, J=5.0 Hz, 1H).

Step 7:

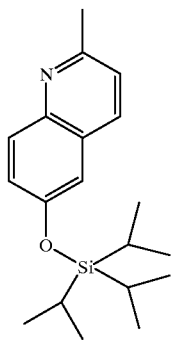

6-Hydroxyquinaldine (1.97 g, 0.0123 mol) and imidazole (0.85 g, 0.0124 mol) were dissolved in DMF (20 ml) and cooled to 0° C. with stirring. Triisopropylsilyl chloride (2.7 ml, 1.05 eq) was added and the mixture stirred for 30 min. NH$_4$Cl solution (saturated) was added and the mixture extracted with EtOAc. The organic extracts were dried (MgSO$_4$), concentrated and chromatographed (SiO$_2$, 4:1–1:1 hexane/EtOAc) to give 3.39 g (88%) of the desired compound. $^1$H NMR (CDCl$_3$) δ 1.12(d, J=8.5 Hz, 18H), 1.30(heptet. J=8.5 Hz, 3H), 2.05 (s, 3H), 7.13 (br s, 1H), 7.22 (d, J=9.0 Hz, 1H), 7.31 (d, J=11.0 Hz), 7.89 (m, 2H).

Step 8:

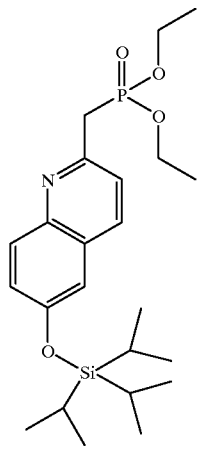

The product of Step 6 (3.39 g, 0.0108 mol) and diisopropylamine (1.66 ml, 1 eq) were dissolved in THF (54 mL) and cooled to −78° C. with stirring. n-Butyllithium (9 ml of a 2.5 M solution in hexanes, 2.1 eq) was added dropwise and after 20 min diethylchlorophosphate (1.7 ml, 1.1 eq) was added. After a further 20 min, the mixture was allowed to warm to RT. NH$_4$Cl solution (saturated) was added and the mixture extracted with EtOAc. The organic extracts were dried (MgSO$_4$), concentrated and chromatographed (SiO$_2$, 1:1 hexane/EtOAc-100% EtOAc) to give 4 g (82%) of the desired compound. $^1$H NMR (CDCl$_3$) δ 1.12 (d, J=8.0 Hz, 18H), 1.25 (t, J=7.5 Hz, 6H), 1.3 (heptet, J=8.0 Hz, 3H), 3.55 (d, J=22 Hz, 2H), 4.08 (q, J=7.5 Hz, 4H), 7.14 (s, 1H), 7.32 (d, J=9.5 Hz, 1H), 7.44 (d, J=7.4 Hz, 1H), 7.90 (d, J=7.4 Hz, 1H), 7.95 (d, J=9.5 Hz, 1H).

Step 9:

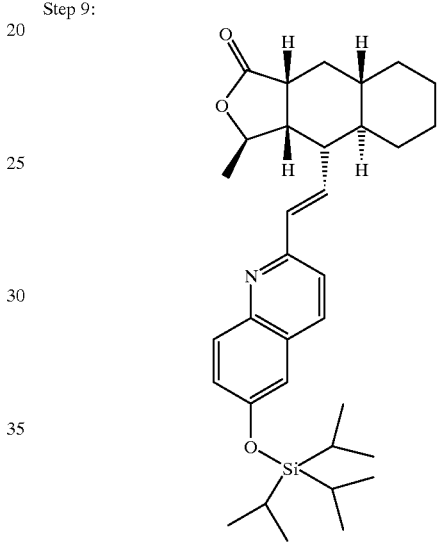

A solution of the product of Step 8 (4 g, 8.86 mmol) in THF (20 ml) was cooled to 0° C. with stirring. n-Butyllithium (3.5 ml of a 2.5M solution in hexanes, 1 eq) was added dropwise. The resulting solution was stirred for a further 10 min and added to a solution of the product of Step 6 (1.9 g, 8.05 mmol) in THF (20 ml) at 0° C. After 1 hr, NH$_4$Cl solution (saturated) was added and the mixture extracted with EtOAc. The organic extracts were dried (MgSO$_4$), concentrated and chromatographed (SiO$_2$, 1:5–1:3 hexane/EtOAc) to give 2.8 g (65%) of the title compound. $^1$H NMR (CDCl$_3$) δ 1.12 (d, J=8.0 Hz, 18H), 1.0–1.5 (m, 11H), 1.43 (d, J=6.0 Hz, 3H), 1.73 (br d, J=9.5 Hz, 2H), 1.84 (m, 1H), 1.92 (dd, J=9.2, 7.0 Hz, 1H), 2.40 (m, 2H), 2.71 (q, J=6.0 Hz, 1H), 4.77 (m, 1H), 6.46 (dd, J=15.8, 9.6 Hz, 1H), 6.69 (d, J=15.8 Hz, 1H), 7.13 (s, 1H), 7.31 (d, J=6.5 Hz, 1H), 7.43 (d, J=8.5 Hz, 1H), 7.90 (d, J=9.0 Hz, 1H), 7.94 (d, J=8.5 Hz, 1H).

Step 10:

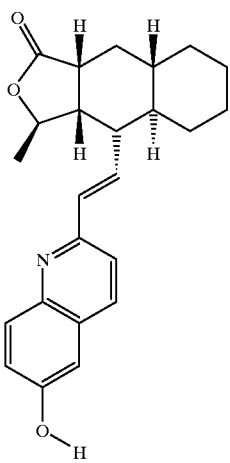

A solution of the product of Step 9 (2.8 g, 5.25 mmol) was stirred in THF (72 ml) at 0° C. Tetrabutylammonium flouride (5.3 ml of a 1M solution in THF, 1 eq) was added dropwise, TLC (5 min) showed complete conversion. NH$_4$Cl solution (saturated) was added and the mixture extracted with EtOAc. The organic extracts were dried (MgSO$_4$), concentrated and chromatographed (SiO$_2$, 1:2–1:1 hexane/EtOAc) to give 1.96 g (99%) of the title compound. $^1$H NMR (CDCl$_3$) δ 1.0–1.4 (m, 8H), 1.45 (d, J=6 Hz, 3H), 1.7–1.9 (m, 3H), 1.97 (m, 1H), 2.43 (m, 2H), 2.72 (q, J=6.5 Hz, 1H), 4.78 (m, 1H), 6.50 (dd, J=15.9, 9.5 Hz, 1H), 6.78 (d, J=15.9 Hz, 1H), 7.17 (s, 1H), 7.34 (d, J=9.0 Hz, 1H), 7.53 (d, J=8.5 Hz, 1H), 8.01 (m, 2H); MS m/z 378 (M$^+$), 332, 264, 236: HRMS calcd for C$_{24}$H$_{28}$NO$_3$ (MH$^+$) 378.2069, found 378.2060. Anal. Calcd for C$_{24}$H$_{27}$NO$_3$.HCl.0.5H$_2$O: C, 68.16: H, 6.91: N, 3.31. Found: C, 68.21: H, 7.64: N, 3.36.

Step 11:

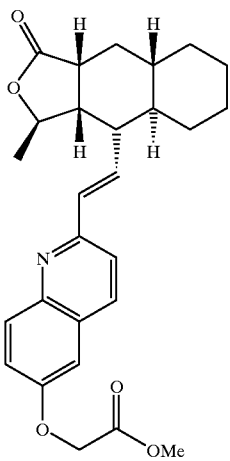

NaH (33 mg of a 60% dispersion in mineral oil, 0.825 mmol) was added to a solution of the product of Step 10 (75 mg, 0.2 mmol) in DMF (1 ml). After stirring for 10 min, methyl bromoacetate (166 ml, 8 eq) was added and after a further 10 min, TLC indicated complete reaction. NH$_4$Cl solution (saturated) was added and the mixture extracted with EtOAc. The organic extracts were dried (MgSO$_4$), concentrated and chromatographed (SiO$_2$, 1:4–1:2 hexane/EtOAc) to give 60 mg (68%) of the title compound. $^1$H NMR (CDCl$_3$) δ 0.8–1.4 (m, 8H), 1.48 (d, J=6.0 Hz, 3H), 1.79 (br d, J=9.0 Hz, 2H), 1.89 (d, J=10.5 Hz, 1H), 1.98 (dd, J=13.5, 6.0 Hz, 1H), 2.46 (m, 2H), 2.75 (q, J=6.5 Hz, 1H), 3.89 (s, 3H), 4.82 (br s, 3H), 6.55 (dd, J=15.7, 9.5 Hz, 1H), 6.58 (d, J=9.5 Hz, 1H), 7.06 (s, 1H), 7.48 (d, J=6.5 Hz, 1H), 7.51 (d, J=8.5 Hz, 1H), 8.03 (t, J=9.0 Hz, 2H). HRMS calcd for C$_{27}$H$_{32}$NO$_5$ (MH$^+$) 450.2280, found 450.2282.

Step 12:

The product of Step 11 (60 mg, 0.136 mmol) was dissolved in 4:1 CH$_3$OH/water (6.5 ml). LiOH (0.25 ml of a 1 M solution in water, 2 eq) was added and the mixture stirred for 2 hs. Water was added and the mixture extracted with EtOAc. The aqueous layer was acidified and extracted with EtOAc (×3), these extracts were dried (MgSO$_4$) and concentrated to give 30 mg of the title compound (50%). $^1$H NMR (CD$_3$OD) δ 0.9–1.5 (m, 8H), 1.42 (d, J=6.0 Hz, 3H), 1.80 (m, 3H), 1.92 (m, 1H), 2.50 (m, 1H), 2.64 (m, 1H), 2.83 (q, J=6.5 Hz, 1H), 4.95 (m, 3H), 6.89 (d, J=15.8 Hz, 1H), 7.16 (dd, J=15.8, 10.0 Hz, 1H), 7.56 (d, J=2.5 Hz, 1H), 7.76 (dd, J=9.5, 2.5 Hz, 1H), 8.08 (d, J=9.5 Hz, 1H), 8.16 (d, J=9.0 Hz, 1H), 8.71 (d, J=9.0 Hz, 1H); MS m/z 420 (18), 392 (100), 302 (2), 117 (8); Anal. Calc'd for C$_{26}$H$_{29}$NO$_5$.HCl.2 H$_2$O: C, 61.47: H, 6.75: N, 2.76. Found: C, 61.02: H, 6.45: N, 2.91.

Using the procedure of Example 1, employing starting materials known in the art or prepared according to procedures similar to those described below in the following examples, the compounds shown in the following Table 1 are prepared, wherein the variables are as defined in the table:

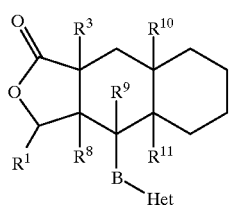

| Ex. | R¹ | R³ | R⁸ | R⁹ | R¹⁰ | R¹¹ | B | Het | Physical Data |
|---|---|---|---|---|---|---|---|---|---|
| 1A | ·····ıCH₃ | ·····ıH | ·····ıH | H | ·····ıH | ◄H | CH=CH-CH₃ | 2-(4,6-dimethylpyridyl) | HRMS (MH+) found: 340.2281 |
| 1B | ·····ıCH₃ | ·····ıH | ·····ıH | H | ·····ıH | ◄H | CH=CH-CH₃ (dashed) | 2-(6-methylpyridyl) | MS (Cl) m/z = 326 (MH+, 100%) |
| 1C | ·····ıCH₃ | ·····ıH | ·····ıH | H | ·····ıH | ◄H | CH=CH-CH₃ | 2-quinolyl | MS (Cl) m/z = 326 (MH+, 100%); [α]$_D^{23}$ = −25.5° (c 0.18, CH₃OH) |
| 1D | ◄CH₃ | ◄H | ◄H | H | ◄H | ·····ıH | CH=CH-CH₃ (dashed) | 2-quinolyl | MS (Cl) m/z = 326 (MH+, 100%); [α]$_D^{23}$ = +15.8° (c 0.16, CH₃OH) |
| 1E | ·····ıCH₃ | ·····ıH | ·····ıH | H | ·····ıH | ◄H | CH=CH-CH₃ | 2-(6-methylpyridyl) | MS (Cl) m/z = 326 (MH+, 100%) |
| 1F | ·····ıCH₃ | ·····ıH | ·····ıH | H | ·····ıH | ◄H | CH=CH-CH₃ | 2-(6-methylpyridyl) | MS (Cl) m/z = 326 (MH+, 100%); mp = 147–148° C.; [α]$_D^{25}$ = −32.1° (c, 0.52, CH₃OH) |

-continued

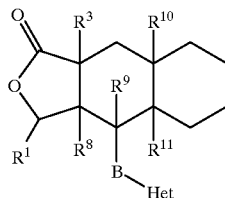

| Ex. | R¹ | R³ | R⁸ | R⁹ | R¹⁰ | R¹¹ | B | Het | Physical Data |
|---|---|---|---|---|---|---|---|---|---|
| 1G | ◄CH₃ | ◄H | ◄H | H | ◄H | ⋯H | ⋮CH=CH-CH₃ | 2-methylpyridin-6-yl | (+)-isomer MS (Cl) m/z = 326 (MH+, 100%) |
| 1H | ⋯CH₃ | ⋯H | ⋯H | H | ⋯H | ◄H | ⋮CH=CH-CH₃ | 5-methylpyridin-2-yl | HRMS (MH+) found: 326.2118 |
| 1I | ⋯CH₃ | ⋯H | ⋯H | H | ⋯H | ◄H | CH=CH-CH₃ | ◄CH₃ | HRMS (MH+) found: 326.2115 |
| 1J | ⋯CH₃ | ⋯H | ⋯H | H | ⋯H | ◄H | CH=CH-CH₃ | 5-methylpyridin-2-yl | HRMS (MH+) found: 326.2118 |
| 1K | ⋯CH₃ | ⋯H | ⋯H | H | ⋯H | ◄H | CH=CH-CH₃ | 3-methylpyridin-2-yl | HRMS (MH+) found: 326.2115 |
| 1L | ⋯CH₃ | ⋯H | ⋯H | H | ⋯H | ◄H | CH=CH-CH₃ | 6-chloropyridin-2-yl | MS (Cl) m/z = 346 (MH+, 100%) |

-continued

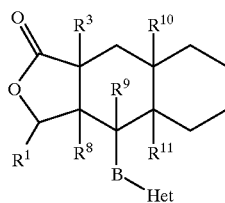

| Ex. | R$^1$ | R$^3$ | R$^8$ | R$^9$ | R$^{10}$ | R$^{11}$ | B | Het | Physical Data |
|---|---|---|---|---|---|---|---|---|---|
| 1M | ⋯CH$_3$ | ⋯H | ⋯H | H | ⋯H | ◂H | propyl | 3-methylpyridin-2-yl | MS m/z = 218(100), 326(7), 120(7), 107(10) |
| 1N | ⋯CH$_3$ | ⋯H | ⋯H | H | ⋯H | ◂H | propyl | 5-methylpyridin-2-yl | MS m/z = 328(100), 326(10), 120(6), 107(12) |
| 1O | ⋯CH$_3$ | ⋯H | ⋯H | H | ⋯H | ◂H | propyl (dashed) | 5-methylpyridin-2-yl | MS m/z = 328(100), 326(7), 120(7), 107(12) |
| 1P | ⋯CH$_3$ | ⋯H | ⋯H | H | ⋯H | ◂H | propyl | 6-methylpyridin-2-yl | MS m/z = 328(100), 326(6), 120(9), 107(13) |
| 1Q | ⋯CH$_3$ | ⋯H | ⋯H | H | ⋯H | ◂H | CH=CH-CH$_3$ | pyridin-2-yl | MS (CI) m/z = 312 (MH+, 100%) |
| 1R | ⋯CH$_3$ | ⋯H | ⋯H | H | ⋯H | ◂H | CH=CH-CH$_3$ | 6-butylpyridin-2-yl | MS (CI) m/z = 368 (MH+, 100%) |

-continued

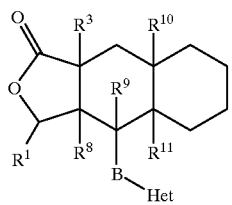

| Ex. | R¹ | R³ | R⁸ | R⁹ | R¹⁰ | R¹¹ | B | Het | Physical Data |
|---|---|---|---|---|---|---|---|---|---|
| 1S | ˙˙˙˙CH₃ | ˙˙˙˙H | ˙˙˙˙H | H | ˙˙˙˙H | ˙˙˙˙H | CH=CH-CH₃ | 6-methylpyridin-2-yl | MS (Cl) m/z = 326 (MH+, 100%) |
| 1T | ˙˙˙˙CH₃ | ˙˙˙˙H | ˙˙˙˙H | H | ˙˙˙˙H | ◂H | CH=CH-CH₃ | 6-(cyclopentylamino)pyridin-2-yl | MS (Cl) m/z = 395 (MH+, 100%) |
| 1U | ˙˙˙˙CH₃ | ˙˙˙˙H | ˙˙˙˙H | H | ˙˙˙˙H | ◂H | CH=CH-CH₃ | 6-(4-methylpiperazin-1-yl)pyridin-2-yl | MS (Cl) m/z = 410 (MH+, 100%) |
| 1V | ˙˙˙˙CH₃ | ˙˙˙˙H | ˙˙˙˙H | H | ˙˙˙˙H | ◂H | CH=CH-CH₃ | 6-(benzylamino)pyridin-2-yl | MS (Cl) m/z = 417 (MH+, 100%) |
| 1W | ˙˙˙˙CH₃ | ˙˙˙˙H | ˙˙˙˙H | H | ˙˙˙˙H | ◂H | CH=CH-CH₃ | quinolin-2-yl | MS (Cl) m/z = 362 (MH+, 100%) |

-continued

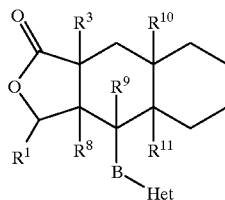

| Ex. | R¹ | R³ | R⁸ | R⁹ | R¹⁰ | R¹¹ | B | Het | Physical Data |
|---|---|---|---|---|---|---|---|---|---|
| 1X | ...''''CH₃ | ...''''H | ...''''H | H | ...''''H | ◄H | CH=CH-CH₃ | 2-ethylpyridin-6-yl | MS (Cl) m/z = 340 (MH+, 100%) |
| 1Y | ...''''CH₃ | ...''''H | ...''''H | H | ...''''H | ◄H | CH=CH-CH₃ | 2-hexylpyridin-6-yl | MS (Cl) m/z = 396 (MH+, 100%) |
| 1Z | ...''''CH₃ | ...''''H | ...''''H | H | ...''''H | ◄H | CH=CH-CH₃ | 2-benzylpyridin-6-yl | MS (Cl) m/z = 402 (MH+, 100%) |
| 1AA | ...''''CH₃ | ...''''H | ...''''H | H | ...''''H | ◄H | CH=CH-CH₃ | 6-methylquinolin-2-yl | HRMS (MH+) found: 376.2266 |
| 1AB | ...''''CH₃ | ...''''H | ...''''H | H | ...''''H | ◄H | CH=CH-CH₃ | 6-methoxyquinolin-2-yl | HRMS (MH+) found: 392.2219 |

-continued

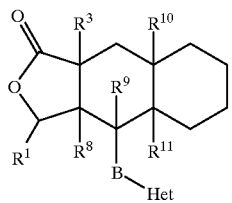

| Ex. | R¹ | R³ | R⁸ | R⁹ | R¹⁰ | R¹¹ | B | Het | Physical Data |
|---|---|---|---|---|---|---|---|---|---|
| 1AC | ⁗CH₃ | ⁗H | ⁗H | H | ⁗H | ◂H | CH=CH–CH₃ | 7-methylquinolin-2-yl | HRMS (MH+) found: 376.2270 |
| 1AD | ⁗CH₃ | ⁗H | ⁗H | H | ⁗H | ◂H | CH=CH–CH₃ | 8-methoxyquinolin-2-yl | HRMS (MH+) found: 392.2219 |
| 1AE | ⁗CH₃ | ⁗H | ⁗H | H | ⁗H | ◂H | CH=CH–CH₃ | 6-propylpyridin-2-yl | MS (Cl) m/z = 354 (MH+, 100%) |
| 1AF | ⁗CH₃ | ⁗H | ⁗H | H | ⁗H | ◂H | CH=CH–CH₃ | 6-isopropylpyridin-2-yl | MS (Cl) m/z = 354 (MH+, 100%) |
| 1AG | ⁗CH₃ | ⁗H | ⁗H | H | ⁗H | ◂H | CH=CH–CH₃ | 6-ethylpyridin-2-yl | MS (Cl) m/z = 340 (MH+, 100%); $[\alpha]_D^{23} = -25.2°$ (c, 0.24, CH₃OH) |

-continued

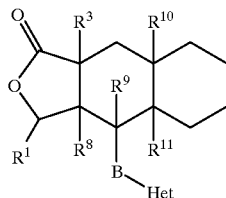

| Ex. | R¹ | R³ | R⁸ | R⁹ | R¹⁰ | R¹¹ | B | Het | Physical Data |
|---|---|---|---|---|---|---|---|---|---|
| 1AH | ⋯CH₃ | ⋯H | ⋯H | H | ⋯H | ◀H | CH=CH-CH₃ | 2-ethyl-pyridine N-oxide | MS (FAB) m/z = 356 (MH+, 100%) |
| 1AI | ⋯CH₃ | ⋯H | ⋯H | H | ⋯H | ◀H | CH=CH-CH₃ | 5,6-dimethylpyridin-2-yl | HRMS (MH+) found: 340.2285 |
| 1AJ | ⋯CH₃ | ⋯H | ⋯H | H | ⋯H | ◀H | CH=CH-CH₃ | quinolin-2-yl | MS (FAB) m/z = 362 (MH+, 100%) |
| 1AK | ⋯CH₃ | ⋯H | ⋯H | H | ⋯H | ◀H | CH=CH-CH₃ | 6-(hydroxymethyl)pyridin-2-yl | MS (FAB) m/z = 342 (MH+, 100%) |
| 1AL | ⋯CH₃ | ⋯H | ⋯H | H | ⋯H | ◀H | CH=CH-CH₃ | 8-methylquinolin-2-yl | HRMS (MH+) found: 376.2274 |

-continued

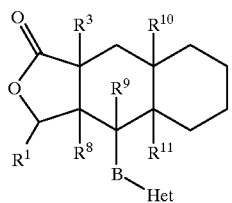

| Ex. | R$^1$ | R$^3$ | R$^8$ | R$^9$ | R$^{10}$ | R$^{11}$ | B | Het | Physical Data |
|---|---|---|---|---|---|---|---|---|---|
| 1AM | ⋯CH$_3$ | ⋯H | ⋯H | H | ⋯H | ◂H | CH=CH-CH$_3$ | 1-methylquinolinium-2-yl | MS (FAB) m/z = 376 (MH+, 100%) |
| 1AN | ⋯CH$_3$ | ⋯H | ⋯H | H | ⋯H | ◂H | CH=CH-CH$_3$ | 6-carboxypyridin-2-yl | MS (FAB) m/z = 356 (MH+, 100%) |
| 1AO | ⋯CH$_3$ | ⋯H | ⋯H | H | ⋯H | ◂H | CH=CH-CH$_3$ | 6-(1,2-dihydroxyethyl)pyridin-2-yl | MS (FAB) m/z = 372 (MH+, 100%) |
| 1AP | ⋯CH$_3$ | ⋯H | ⋯H | H | ⋯H | ◂H | CH=CH-CH$_3$ | 6-(dimethylaminomethyl)pyridin-2-yl | MS (FAB) m/z = 369 (MH+, 100%) |
| 1AQ | ⋯CH$_3$ | ⋯H | ⋯H | H | ⋯H | ◂H | CH=CH-CH$_3$ | 6-cyclopropylpyridin-2-yl | MS (FAB) m/z = 352 (MH+, 100%) |

-continued

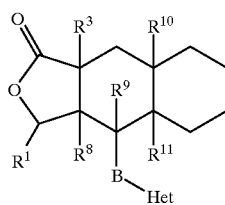

| Ex. | R[1] | R[3] | R[8] | R[9] | R[10] | R[11] | B | Het | Physical Data |
|---|---|---|---|---|---|---|---|---|---|
| 1AR | ⋯CH₃ | ⋯H | ⋯H | H | ⋯H | ◂H | CH=CH-CH₃ | 6-(2,3-dihydroxypropyl)pyridin-2-yl | MS (FAB) m/z = 386 (MH+, 100%) |
| 1AS | ⋯CH₃ | ⋯H | ⋯H | HH | ⋯H | ◂H | CH=CH-CH₃ | 6-(ethoxycarbonyloxy)quinolin-2-yl | MS m/z = 464(100) |
| 1AT | ⋯CH₃ | ⋯H | ⋯H | H | ⋯H | ◂H | CH=CH-CH₃ | 6-(dimethylamino)pyridin-2-yl | MS (CI) m/z = 355 (MH+, 100%) |
| 1AU | ⋯CH₃ | ⋯H | ⋯H | H | ⋯H | ◂H | CH=CH-CH₃ | 6-(methylamino)pyridin-2-yl | MS (FAB) m/z = 341 (MH+, 100%) |
| 1AV | ⋯CH₃ | ⋯H | ⋯H | H | ⋯H | ◂H | CH=CH-CH₃ | 6-(2-hydroxyethoxy)quinolin-2-yl | HRMS (MH+) found: 422.2340 |

-continued
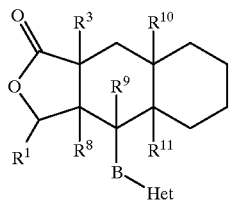
| Ex. | R¹ | R³ | R⁸ | R⁹ | R¹⁰ | R¹¹ | B | Het | Physical Data |
|---|---|---|---|---|---|---|---|---|---|
| 1AW | ┈CH₃ | ┈H | ┈H | H | | ┈H | ◂H, CH=CH-CH₃ | quinoline-2-yl, 6-O-CH₂-C(O)-O-tBu | HRMS (MH+) found: 492.2738 |
| 1AX | ┈CH₃ | ┈H | ┈H | H | | ┈H | ◂H, CH=CH-CH₃ | quinoline-2-yl, 6-O-CH₂-C(O)-OMe | HRMS (MH+) found: 450.2282 |
| 1AY | ┈CH₃ | ┈H | ┈H | | | ┈H | ◂H, CH=CH-CH₃ | 5-methoxypyridin-2-yl | MS (Cl) m/z = 342 (MH+, 100%) |
| 1AZ | ┈CH₃ | ┈H | ┈H | ┈H | | ┈H | ◂H, CH=CH-CH₃ | 5-phenylpyridin-2-yl | MB (FAB) m/z = 388 (MH+, 100%) |

-continued
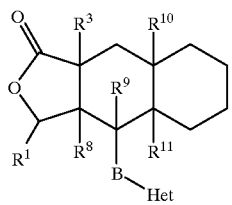
| Ex. | R¹ | R³ | R⁸ | R⁹ | R¹⁰ | R¹¹ | B | Het | Physical Data |
|---|---|---|---|---|---|---|---|---|---|
| 1BA | ⋯CH₃ | ⋯H | ⋯H | H | ⋯H | ◂H | CH=CH-CH₃ | 6-ethoxyquinolin-2-yl | HRMS (MH+) found: 406.2374 |
| 1BB | ⋯CH₃ | ⋯H | ⋯H | H | ⋯H | ◂H | CH=CH-CH₃ | 6-(2-(tert-butoxycarbonylamino)ethoxy)quinolin-2-yl | HRMS (MH+) found: 521.3009 |
| 1BC | ⋯CH₃ | ⋯H | ⋯H | H | ⋯H | ◂H | CH=CH-CH₃ | 1H-benzimidazol-2-yl | HRMS (MH+) found: 351.2082 |
| 1BD | ⋯CH₃ | ⋯H | ⋯H | H | ⋯H | ◂H | CH=CH-CH₃ | 6-(2-aminoethoxy)quinolin-2-yl | MS m/z = 421(100), 232(21), 201(4) |

-continued
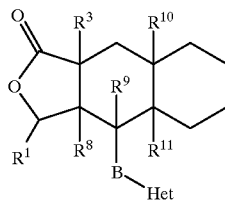
| Ex. | R¹ | R³ | R⁸ | R⁹ | R¹⁰ | R¹¹ | B | Het | Physical Data |
|---|---|---|---|---|---|---|---|---|---|
| 1BE | ⋯CH₃ | ⋯H | ⋯H | H | ⋯H | ◂H | CH=CH-CH₃ | 6-fluoroquinolin-2-yl | MS (FAB) m/z = 380 (MH+, 100%) |
| 1BF | ⋯CH₃ | ⋯H | ⋯H | H | ⋯H | ◂H | CH=CH-CH₃ | 6-chloroquinolin-2-yl | MS (FAB) m/z = 396 (MH+, 100%) |
| 1BG | ⋯CH₃ | ⋯H | ⋯H | H | ⋯H | ◂H | CH=CH-CH₃ | 6-hydroxyquinolin-2-yl | HRMS (MH+) found: 378.2060 |
| 1BH | ⋯CH₃ | ⋯H | ⋯H | H | ⋯H | ◂H | CH=CH-CH₃ | 6-methoxyquinolin-2-yl | MS: 406 (M + H⁺) |

-continued
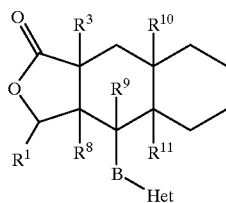
| Ex. | R¹ | R³ | R⁸ | R⁹ | R¹⁰ | R¹¹ | B | Het | Physical Data |
|---|---|---|---|---|---|---|---|---|---|
| 1BI | ⋯CH₃ | ⋯H | ⋯H | ⋯H | ⋯H | ◂H | CH=CH-CH₃ | pyridine-C₆H₄-CF₃ (para) | MS (ESI) m/z = 456 (MH+, 100%) |
| 1BJ | ⋯CH₃ | ⋯H | ⋯H | ⋯H | ⋯H | ◂H | CH=CH-CH₃ | pyridine-C₆H₄-CF₃ (meta) | MS (ESI) m/z = 456 (MH+, 100%) |
| 1BK | ⋯CH₃ | ⋯H | ⋯H | ⋯H | ⋯H | ◂H | CH=CH-CH₃ | pyridine-C₆H₄-CH₃ | MS (ESI) m/z = 402 (MH+, 100%) |

-continued

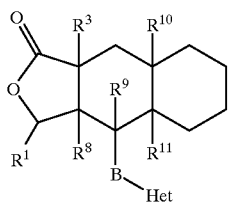

| Ex. | R¹ | R³ | R⁸ | R⁹ | R¹⁰ | R¹¹ | B | Het | Physical Data |
|---|---|---|---|---|---|---|---|---|---|
| 1BL | ·····CH₃ | ·····H | ·····H | ·····H | ·····H | ◄H | CH=CH-CH₃ | 5-(thiophen-3-yl)pyridin-2-yl | MS (CI) m/z = 394 (MH+, 43%), 188(100%) |
| 1BM | ·····CH₃ | ·····H | ·····H | H | ·····H | ◄H | CH=CH-CH₃ | 6-hydroxyquinolin-2-yl | $[\alpha]_D^{25} = -42.88°$ (c, 1.0, CH₃OH) |
| 1BN | ◄CH₃ | ◄H | ◄H | H | ◄H | ·····H | CH=CH-CH₃ | 6-hydroxyquinolin-2-yl | HRMS (MH+) found: 378.2060 $[\alpha]_D^{25} = +39.95°$ (C 1.5, CH₃OH) |
| 1BO | ·····CH₃ | ·····H | ·····H | ·····H | ·····H | ◄H | CH=CH-CH₃ | 5-(isoquinolin-3-yl)pyridin-2-yl | MS (FAB) m/z = 438 (MH+, 100%) |

-continued
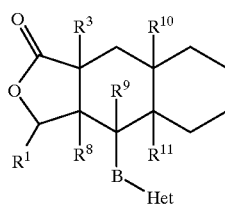
| Ex. | R[1] | R[3] | R[8] | R[9] | R[10] | R[11] | B | Het | Physical Data |
|---|---|---|---|---|---|---|---|---|---|
| 1BP | ⸺CH₃ | ⸺H | ⸺H | ⸺H | ⸺H | ◂H | CH=CH-CH₃ | 4-(dimethylamino)phenyl-pyridin-2-yl | MS (CI) m/z = 431 (MH+, 100%) |
| 1BQ | ⸺CH₃ | ⸺H | ⸺H | ⸺H | ⸺H | ◂H | CH=CH-CH₃ | benzo[1,3]dioxol-5-yl-pyridin-2-yl | MS (FAB) m/z = 432 (MH+, 100%) |
| 1BR | ⸺CH₃ | ⸺H | ⸺H | H | ⸺H | ◂H | n-propyl | 6-methoxyquinolin-2-yl | MS (FAB) m/z = 394 (MH+, 100%) |

-continued
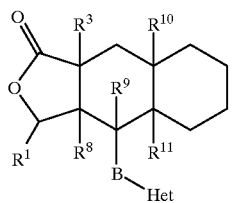
| Ex. | R¹ | R³ | R⁸ | R⁹ | R¹⁰ | R¹¹ | B | Het | Physical Data |
|---|---|---|---|---|---|---|---|---|---|
| 1BS | ⋯CH₃ | ⋯H | ⋯H | ⋯H | | ⋯H | ◂H | (pyridine-phenyl-OCF₃ group) | MS (FAB) m/z = 472 (MH+, 100%) |
| 1BT | ⋯CH₃ | ⋯CH₃ | ⋯H | ⋯H | | ⋯H | ◂H | (pyridine-mesityl group) | MS (FAB) m/z = 430 (MH+, 100%) |
| 1BU | ◂CH₃ | ◂H | ◂H | H | | ◂H | ⋯H | (8-hydroxyquinoline group) | MS m/z = 378(100), 377(15), 154(2), 150(2) |
| 1BV | ◂CH₃ | ◂H | ◂H | H | | ◂H | ⋯H | (quinoline-6-OCH₂COOH group) | MS m/z = 433(5), 420(18), 393(28), 392(100), 117(8) [α]_D^{23} = +15.7° (c 0.45, CH₃OH) |

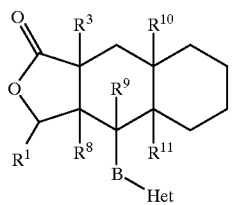
| Ex. | R¹ | R³ | R⁸ | R⁹ | R¹⁰ | R¹¹ | B | Het | Physical Data |
|---|---|---|---|---|---|---|---|---|---|
| 1BW | ⋯CH₃ | ⋯H | ⋯H | H | ⋯H | ◂H | ![CH=CH-CH₃] | ![quinoline-OCH₂COOH] | $[\alpha]_D^{23} = -14.65°$ (c 0.45, CH₃OH) |
| 1BX | ⋯CH₃ | ⋯H | ⋯H | H | ⋯H | ◂H | ![CH=CH-CH₃] | ![4-methoxyquinoline] | HRMS (MH+) found: 393.2225 |
| 1BY | ⋯CH₃ | ⋯H | ⋯H | H | ⋯H | ◂H | ![CH=CH-CH₃] | ![4-benzyloxyquinoline] | HRMS (MH+) found: 468.2539 |
| 1BZ | ◂CH₃ | ◂H | ◂H | H | ◂H | ⋯H | ![CH=CH-CH₃] | ![6-benzyloxyquinoline] | HRMS (MH+) found: 468.2536 |

-continued
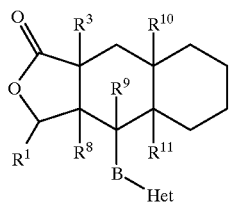
| Ex. | R¹ | R³ | R⁸ | R⁹ | R¹⁰ | R¹¹ | B | Het | Physical Data |
|---|---|---|---|---|---|---|---|---|---|
| 1CA | —CH₃ | —H | —H | H | —H | ⋯H | (butyl) | 6-hydroxyquinolin-2-yl | HRMS (MH+) found: 380.2232 |
| 1CB | ⋯CH₃ | ⋯H | ⋯H | ⋯H | ⋯H | —H | CH=CHCH₃ | 5-(4-fluorophenyl)pyridin-2-yl | MS (ESI) m/z = 406 (MH+, 100%) |
| 1CC | ⋯CH₃ | ⋯H | ⋯H | ⋯H | ⋯H | —H | CH=CHCH₃ | 5-(3-chloro-4-fluorophenyl)pyridin-2-yl | MS (FAB) m/z = 440 (MH+, 100%) |
| 1CD | ⋯CH₃ | ⋯H | ⋯H | ⋯H | ⋯H | —H | CH=CHCH₃ | 5-(benzo[1,3]dioxol-5-ylmethoxy)pyridin-2-yl | MS (FAB) m/z = 4625 (MH+, 100%) |

-continued

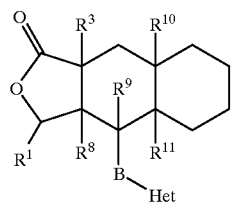

| Ex. | R¹ | R³ | R⁸ | R⁹ | R¹⁰ | R¹¹ | B | Het | Physical Data |
|---|---|---|---|---|---|---|---|---|---|
| 1CE | ⋯CH₃ | ⋯H | ⋯H | ⋯H | ⋯H | ◂H | CH=CH-CH₃ | 5-(pyridin-4-ylmethoxy)pyridin-2-yl | MS (FAB) m/z = 419 (MH+, 100%) |
| 1CF | ⋯CH₃ | ⋯H | ⋯H | ⋯H | ⋯H | ◂H | CH=CH-CH₃ | 5-[(3-methoxycarbonylphenyl)methoxy]pyridin-2-yl | MS (FAB) m/z = 476 (MH+, 100%) |
| 1CG | ⋯CH₃ | ⋯H | ⋯H | ⋯H | ⋯H | ◂H | CH=CH-CH₃ | 5-[3-(dimethylaminomethyl)phenyl]pyridin-2-yl | MS (FAB) m/z = 445 (MH+, 100%) |
| 1CH | ⋯CH₃ | ⋯H | ⋯H | ⋯H | ⋯H | ◂H | CH=CH-CH₃ | 5-[3-(hydroxymethyl)phenyl]pyridin-2-yl | MS (FAB) m/z = 418 (MH+, 100%) |

-continued
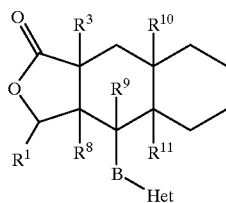
| Ex. | R¹ | R³ | R⁸ | R⁹ | R¹⁰ | R¹¹ | B | Het | Physical Data |
|---|---|---|---|---|---|---|---|---|---|
| 1CI | ⋯CH₃ | ⋯H | ⋯H | ⋯H | | ⋯H | CH=CH-CH₃ | 3-(pyridin-2-yl)benzaldehyde | MS (FAB) m/z = 416 (MH+, 100%) |
| 1CJ | ⋯CH₃ | ⋯H | ⋯H | ⋯H | | ⋯H | CH=CH-CH₃ | 5-((3-iodobenzyl)oxy)pyridin-2-yl | MS (FAB) m/z = 544 (MH+, 100%) |
| 1CK | CH₃ | H | H | H | H | ⋯H | CH=CH-CH₃ | 6-(pyrrolidine-1-carbonyl)quinolin-2-yl | HRMS found: 459.2635 |

US 6,326,380 B1
75 76
-continued
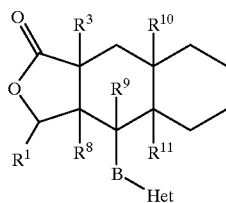
| Ex. | R¹ | R³ | R⁸ | R⁹ | R¹⁰ | R¹¹ | B | Het | Physical Data |
|---|---|---|---|---|---|---|---|---|---|
| 1CL | ⋯CH₃ | ⋯H | ⋯H | ⋯H | ⋯H | ◂H | CH=CH-CH₃ | pyridin-2-yl with 5-OCH₂-(4-methoxyphenyl) | MS (FAB) m/z = 448 (MH+, 100%) |
| 1CM | ⋯CH₃ | ⋯H | ⋯H | ⋯H | ⋯H | ◂H | CH=CH-CH₃ | pyridin-2-yl with 5-OCH₂-(3-methoxyphenyl) | MS (FAB) m/z = 448 (MH+, 100%) |
| 1CN | ⋯CH₃ | ⋯H | ⋯H | ⋯H | ⋯H | ◂H | CH=CH-CH₃ | pyridin-2-yl with 5-OCH₂-(3-trifluoromethylphenyl) | MS (FAB) m/z = 486 (MH+, 100%) |

-continued

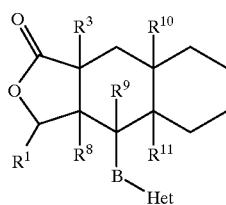

| Ex. | R¹ | R³ | R⁸ | R⁹ | R¹⁰ | R¹¹ | B | Het | Physical Data |
|---|---|---|---|---|---|---|---|---|---|
| 1CO | ·····ııCH₃ | ·····ııH | ·····ııH | ·····ııH | ·····ııH | ◂■H | (CH=CH-CH₃ group) | (pyridine-O-CH₂-phenyl-COOH group) | MS (FAB) m/z = 462 (MH+, 100%) |
| 1CP | ·····ııCH₃ | ·····ııH | ·····ııH | ·····ııH | ·····ııH | ◂■H | (CH=CH-CH₃ group) | (pyridine-O-CH₂-phenyl-OCH₃ group) | MS (Cl) m/z = 448 (MH+, 100%) |
| 1CQ | ·····ııCH₃ | ·····ııH | ·····ııH | ·····ııH | ·····ııH | ◂■H | (CH=CH-CH₃ group) | (pyridine-O-CH₂-phenyl-CF₃ group) | MS (Cl) m/z = 486 (MH+, 100%) |

-continued
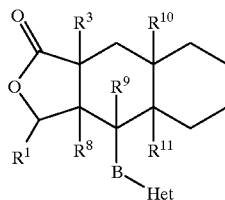
| Ex. | $R^1$ | $R^3$ | $R^8$ | $R^9$ | $R^{10}$ | $R^{11}$ | B | Het | Physical Data |
|---|---|---|---|---|---|---|---|---|---|
| 1CR | ⋯CH$_3$ | ⋯H | ⋯H | ⋯H | ⋯H | ◂H | CH=CH-CH$_3$ | 5-(4-chlorophenyl)pyridin-2-yl | MS (Cl) m/z = 422 (MH+, 100%) |
| 1CS | ⋯CH$_3$ | ⋯H | ⋯H | ⋯H | ⋯H | ◂H | CH=CH-CH$_3$ | 5-(1-phenylethoxy)pyridin-2-yl | MS (Cl) m/z = 432 (MH+, 100%) |
| 1CT | ⋯CH$_3$ | ⋯H | ⋯H | ⋯H | ⋯H | ◂H | CH=CH-CH$_3$ | 5-(2-phenylethoxy)pyridin-2-yl | MS (Cl) m/z = 432 (MH+, 100%) |
| 1CU | ⋯CH$_3$ | ⋯H | ⋯H | ⋯H | ⋯H | ◂H | CH=CH-CH$_3$ | 5-(3-phenylpropoxy)pyridin-2-yl | MS (FAB) m/z = 446 (MH+, 100%) |

-continued

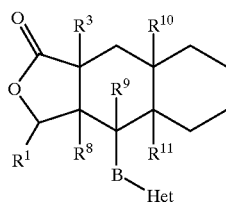

| Ex. | R$^1$ | R$^3$ | R$^8$ | R$^9$ | R$^{10}$ | R$^{11}$ | B | Het | Physical Data |
|---|---|---|---|---|---|---|---|---|---|
| 1CV | ◀CH$_3$ | ◀H | ◀H | ◀H | ◀H | ⋯H | CH=CH–CH$_3$ | 5-(benzyloxy)pyridin-2-yl | MS (CI) m/z = 418 (MH+, 100%); $[\alpha]_D^{24}$ = +26.2° (c 0.46, CH$_3$OH) |
| 1CW | ◀CH$_3$ | ◀H | ◀H | ◀H | ◀H | ⋯H | CH=CH–CH$_3$ | 5-(3-chlorophenyl)pyridin-2-yl | MS (CI) m/z = 422 (MH+, 100%); $[\alpha]_D^{24}$ = +19.8° (c 0.39, CH$_3$OH) |
| 1CX | ◀CH$_3$ | ◀H | ◀H | ◀H | ◀H | ⋯H | CH=CH–CH$_3$ | 5-(thiophen-2-yl)pyridin-2-yl | MS (CI) m/z = 394 (MH+, 100%); $[\alpha]_D^{24}$ = +23.8° (c 0.20, CH$_3$OH) |
| 1CY | ⋯CH$_3$ | ⋯H | ⋯H | ⋯H | ⋯H | ◀H | CH=CH–CH$_3$ | 5-(3-carboxyphenyl)pyridin-2-yl | MS (FAB) m/z = 432 (MH+, 100%) |

-continued
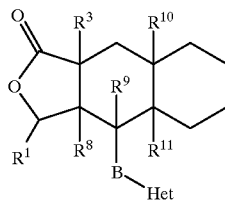
| Ex. | R$^1$ | R$^3$ | R$^8$ | R$^9$ | R$^{10}$ | R$^{11}$ | B | Het | Physical Data |
|---|---|---|---|---|---|---|---|---|---|
| 1CZ | ⋯CH$_3$ | ⋯H | ⋯H | ⋯H | ⋯H | ◂H | CH=CH-CH$_3$ | 2-(6-hydroxyquinolinyl) | MS: 396 (M + H$^+$) |
| 1DA | ◂CH$_3$ | ◂H | ◂H | ◂H | ◂H | ⋯H | CH=CH-CH$_3$ | 2-(6-aminoquinolinyl) | HRMS (MH+) found: 377.2224 |
| 1DB | ◂CH$_3$ | ◂H | ◂H | ◂H | ◂H | ⋯H | CH=CH-CH$_3$ | 2-(6-carboxyquinolinyl) | MS m/z = 406(100), 241(25), 225(51), 194(56), 168(53) |
| 1DC | ◂CH$_3$ | ◂H | ◂H | ◂H | ◂H | ⋯H | CH=C(CH$_3$)$_2$ | 2-(6-methoxyquinolinyl) | HRMS (MH+) found: 406.2381 |

-continued
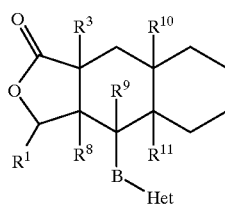
| Ex. | R¹ | R³ | R⁸ | R⁹ | R¹⁰ | R¹¹ | B | Het | Physical Data |
|---|---|---|---|---|---|---|---|---|---|
| 1DD | ",,,CH₃ | ",,,H | ",,,H | ",,,H | | ",,,H | H (bold wedge); CH=CH-CH₃ | pyridine-phenyl-NHC(O)CH₃ | MS (Cl) m/z = 445 (MH+, 100%) |
| 1DE | CH₃ (bold) | H (bold) | H (bold) | H | | H (bold) | ",,,H; CH=CH-CH₃ | quinoline-O-CH₂-C(O)-morpholine | HRMS (MH+) found: 505.2698 |
| 1DF | ",,,CH₃ | ",,,H | ",,,H | ",,,H | ",,,H | H (bold); CH=CH-CH₃ | pyridine-phenyl-phenyl | MS (FAB) m/z = 464 (MH+, 100%) |

-continued
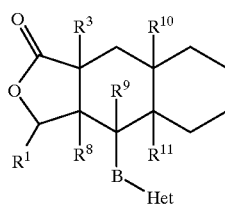
| Ex. | $R^1$ | $R^3$ | $R^8$ | $R^9$ | $R^{10}$ | $R^{11}$ | B | Het | Physical Data |
|---|---|---|---|---|---|---|---|---|---|
| 1DG | ⋯CH₃ | ⋯H | ⋯H | ⋯H | ⋯H | H | CH=CH-CH₃ | 5-(3-OCF₃-phenyl)pyridin-2-yl | MS (FAB) m/z = 472 (MH+, 100%) |
| 1DH | CH₃ | H | H | H | H | ⋯H | CH=CH-CH₃ | 6-(OCH(CH₃)C(O)OCH₃)quinolin-2-yl | HRMS (MH+) found: 464.2431 |
| 1DI | CH₃ | H | H | H | H | ⋯H | CH=CH-CH₃ | 6-(OCH(Ph)C(O)OCH₃)quinolin-2-yl | HRMS (MH+) found: 526.2592 |

-continued

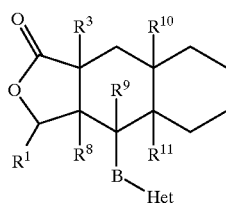

| Ex. | R$^1$ | R$^3$ | R$^8$ | R$^9$ | R$^{10}$ | R$^{11}$ | B | Het | Physical Data |
|---|---|---|---|---|---|---|---|---|---|
| 1DJ | ◀CH$_3$ | ◀H | ◀H | ◀H | ◀H | ⋯H | CH=CH-CH$_3$ | pyridyl-phenyl-3-CH$_3$ | MS (ESI) m/z = 402 (MH+, 100%); [α]$_D^{22}$ = +23.2° (c 0.55, CH$_3$OH) |
| 1DK | ◀CH$_3$ | ◀H | ◀H | ◀H | ◀H | ⋯H | CH=CH-CH$_3$ | pyridyl-phenyl-2-CH$_3$ | MS (ESI) m/z = 402 (MH+, 100%); [α]$_D^{22}$ = +18.1° (c 0.42, CH$_3$OH) |
| 1DL | ◀CH$_3$ | ◀H | ◀H | ◀H | ◀H | ⋯H | CH=CH-CH$_3$ | pyridyl-phenyl-2-OCH$_3$ | MS (FAB) m/z = 418 (MH+, 100%); [α]$_D^{23}$ = +19.5° (c 0.86, CH$_3$OH) |
| 1DM | ◀CH$_3$ | ◀H | ◀H | H | ◀H | ⋯H | CH=CH-CH$_3$ | quinolinyl-O-CH(CH$_3$)-C(O)NH-phenyl | HRMS (MH+) found: 525.2746 |

-continued
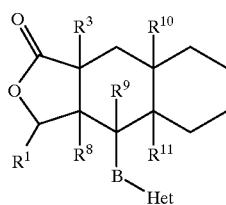
| Ex. | R$^1$ | R$^3$ | R$^8$ | R$^9$ | R$^{10}$ | R$^{11}$ | B | Het | Physical Data |
|---|---|---|---|---|---|---|---|---|---|
| 1DN | CH$_3$ | H | H | H | H | H | CH=CHCH$_3$ | quinolin-2-yl with 6-O-CH(CH$_2$CH$_3$)C(O)OCH$_3$ | HRMS (MH+) found: 478.2584 |
| 1DO | CH$_3$ | H | H | H | H | H | CH=CH-CH$_3$ | 5-(3-fluorophenyl)pyridin-2-yl | MS (ESI) m/z = 418 (MH+, 100%) [α]$_D^{23}$ = +23.9° (c 0.38, CH$_3$OH) |
| 1DP | CH$_3$ | H | H | H | H | H | CH=CH-CH$_3$ | 5-(3-nitrophenyl)pyridin-2-yl | MS (ESI) m/z = 433 (MH+, 100%) [α]$_D^{22}$ = +22.3° (c 0.44, CH$_3$OH) |

-continued
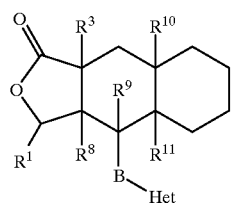
| Ex. | R¹ | R³ | R⁸ | R⁹ | R¹⁰ | R¹¹ | B | Het | Physical Data |
|---|---|---|---|---|---|---|---|---|---|
| 1DQ | ◂CH₃ | ◂H | ◂H | ◂H | ◂H | ⋯H | CH=CH-CH₃ | pyridine-phenyl-OCH₃ | MS (ESI) m/z = 418 (MH+, 100%) |
| 1DR | ◂CH₃ | ◂H | ◂H | ◂H | ◂H | ⋯H | CH=CH-CH₃ | pyridine-benzodioxole | MS (CI) m/z = 432 (MH+, 100%) |
| 1DS | ◂CH₃ | ◂H | ◂H | ◂H | ◂H | ⋯H | CH=CH-CH₃ | pyridine-3,5-dichlorophenyl | MS (ESO) m/z = 456 (MH+, 100%) [α]$_D^{22}$ = +20.3° (c 0.30, CH₃OH) |
| 1DT | ◂CH₃ | ◂H | ◂H | ◂H | ◂H | ⋯H | CH=CH-CH₃ | pyridine-5-chlorothiophene | MS (ESI) m/z = 428 (MH+, 100%) [α]$_D^{24}$ = +25.4° (c 0.26, CH₃OH) |

-continued
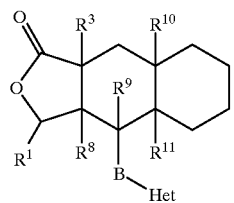
| Ex. | R¹ | R³ | R⁸ | R⁹ | R¹⁰ | R¹¹ | B | Het | Physical Data |
|---|---|---|---|---|---|---|---|---|---|
| 1DU | —CH₃ | —H | —H | —H | —H | ⋯H | CH=CH-CH₃ | 5-(2-fluorophenyl)pyridin-2-yl | MS (CI) m/z = 406 (MH+, 100%) [α]$_D^{24}$ = +17.2° (c 0.50, CH₃OH) |
| 1DV | ⋯CH₃ | ⋯H | ⋯H | ⋯H | ⋯H | —H | CH=CH-CH₃ | 5-(3-(phenylsulfonylamino)phenyl)pyridin-2-yl | MS (FAB) m/z = 543 (MH+, 100%) |
| 1DW | ⋯CH₃ | ⋯H | ⋯H | ⋯H | ⋯H | —H | CH=CH-CH₃ | 5-(3-benzamidophenyl)pyridin-2-yl | MS (FAB) m/z = 507 (MH+, 100%) |
| 1DX | ⋯CH₃ | ⋯H | ⋯H | ⋯H | ⋯H | —H | CH=CH-CH₃ | 5-chloro-6-methoxyquinolin-2-yl | MS (CI) m/z = 426 (MH+, 100%) |

-continued

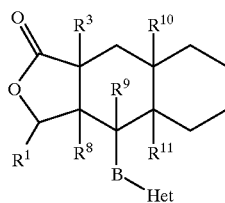

| Ex. | R¹ | R³ | R⁸ | R⁹ | R¹⁰ | R¹¹ | B | Het | Physical Data |
|---|---|---|---|---|---|---|---|---|---|
| 1DY | ◄━CH₃ | ◄━H | ◄━H | ◄━H | ◄━H | ⋯H | CH=CH-CH₃ | 5-(2-trifluoromethylphenyl)pyridin-2-yl | MS (Cl) m/z = 456 (MH+, 100%) |
| 1DZ | ◄━CH₃ | ◄━H | ◄━H | ◄━H | ◄━H | ⋯H | CH=CH-CH₃ | 5-(2-chlorophenyl)pyridin-2-yl | MS (Cl) m/z = 422 (MH+, 95%) $[\alpha]_D^{23} = +15.1°$ (c 0.35, CH₃OH) |
| 1EA | ◄━CH₃ | ◄━H | ◄━H | ◄━H | ◄━H | ⋯H | CH=CH-CH₃ | 5-(pyridin-2-yl)pyridin-2-yl | MS (Cl) m/z = 389 (MH+, 100%) |
| 1EB | ◄━CH₃ | ◄━H | ◄━H | ◄━H | ◄━H | ⋯H | CH=CH-CH₃ | 5-(pyridin-3-yl)pyridin-2-yl | MS (FAB) m/z = 389 (MH+, 100%) |

-continued
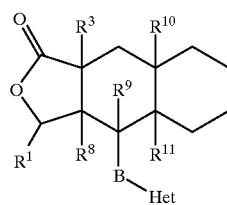
| Ex. | R¹ | R³ | R⁸ | R⁹ | R¹⁰ | R¹¹ | B | Het | Physical Data |
|---|---|---|---|---|---|---|---|---|---|
| 1EC | ◂CH₃ | ◂H | ◂H | ◂H | ◂H | ┄H | CH=CH-CH₃ | 2-pyridyl-5-phenyl | MS (FAB) m/z = 388 (MH+, 100%) |
| 1ED | ◂CH₃ | ◂H | ◂H | ◂H | ◂H | ┄H | CH=CH-CH₃ | 2-pyridyl-5-(3-acetylphenyl) | MS (Cl) m/z = 430 (MH+, 100%) |
| 1FE | ◂CH₃ | ◂H | ◂H | ◂H | ◂H | ┄H | CH=CH-CH₃ | 2-pyridyl-5-(3-isopropylphenyl) | MS (Cl) m/z = 430 (MH+, 100%) |
| 1EF | ◂CH₃ | ◂H | ◂H | ◂H | ◂H | ┄H | CH=CH-CH₃ | 2-pyridyl-5-benzyl | MS (Cl) m/z = 402 (MH+, 100%) [α]$_D^{24}$ = +15.7° (c 0.33, CHCl₃) |

-continued
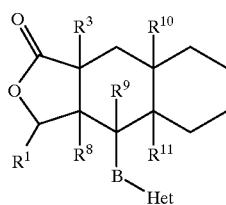
| Ex. | R¹ | R³ | R⁸ | R⁹ | R¹⁰ | R¹¹ | B | Het | Physical Data |
|---|---|---|---|---|---|---|---|---|---|
| 1EG | ⋯CH₃ | ⋯H | ⋯H | ⋯H | ⋯H | ◂H | CH=CH-CH₃ | pyridine-phenyl-O-CH₂-C(O)-OCH₃ | MS (CI) m/z = 476 (MH+, 100%) |
| 1EH | ⋯CH₃ | ⋯H | ⋯H | ⋯H | ⋯H | ◂H | CH=CH-CH₃ | pyridine-phenyl-NH-S(O)₂-CH₃ | MS (FAB) m/z = 481 (MH+, 100%) |
| 1EI | ⋯CH₃ | ⋯H | ⋯H | ⋯H | ⋯H | ◂H | CH=CH-CH₃ | pyridine-phenyl-O-CH₂-C(O)-OH | MS (ESI) m/z = 462 (MH+, 100%) |

-continued
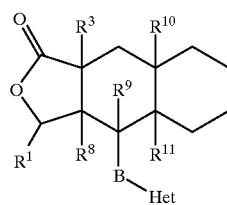
| Ex. | R¹ | R³ | R⁸ | R⁹ | R¹⁰ | R¹¹ | B | Het | Physical Data |
|---|---|---|---|---|---|---|---|---|---|
| 1EJ | CH₃ | H | H | H | H | H | CH=CH-CH₃ | pyridine-phenyl-CF₃ | MS (ESI) m/z = 456 (MH+, 100%) $[\alpha]_D^{20}$ = +40.0° (c 0.39, CHCl₃) |
| 1EK | CH₃ | H | H | H | H | H | CH=CH-CH₃ | pyridine-phenyl-2,3-F₂ | MS (ESI) m/z = 424 (MH+, 100%) $[\alpha]_D^{22}$ = +25.5° (c 0.26, CH₃OH) |
| 1EL | CH₃ | H | H | H | H | H | CH=CH-CH₃ | pyridine-phenyl-F-CF₃ | MS (ESI) m/z = 474 (MH+, 100%) $[\alpha]_D^{22}$ = +22.4° (c 0.50, CH₃OH) |
| 1EM | CH₃ | H | H | H | H | H | CH=CH-CH₃ | pyridine-phenyl-NHSO₂-propyl | MS (FAB) m/z = 509 (MH+, 100%) |

-continued
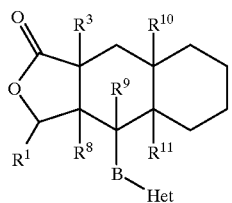
| Ex. | R¹ | R³ | R⁸ | R⁹ | R¹⁰ | R¹¹ | B | Het | Physical Data |
|---|---|---|---|---|---|---|---|---|---|
| 1EN | ◂CH₃ | ◂H | ◂H | ◂H | ◂H | ⋯H | CH(ethyl)(methyl) | pyridyl-phenyl-NHSO₂iPr | MS (FAB) m/z = 509 (MH+, 100%) |
| 1EO | ◂CH₃ | ◂H | ◂H | ◂H | ◂H | ⋯H | CH(ethyl)(methyl) | pyridyl-furyl | MS (ESI) m/z = 378 (MH+, 100%) |
| 1EP | ◂CH₃ | ◂H | ◂H | ◂H | ◂H | ⋯H | CH(ethyl)(methyl) | pyridyl-phenyl-NHSO₂Bu | MS (ESI) m/z = 523 (MH+, 100%) |

-continued
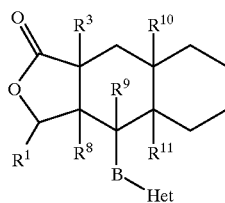
| Ex. | R¹ | R³ | R⁸ | R⁹ | R¹⁰ | R¹¹ | B | Het | Physical Data |
|---|---|---|---|---|---|---|---|---|---|
| 1EQ | CH₃ | H | H | H | H | H | CH=CH-CH₃ | pyridine-phenyl-NHSO₂Et | MS (ESI) m/z = 495 (MH+, 100%) |
| 1ER | CH₃ | H | H | H | H | H | CH=CH-CH₃ | pyridine-phenyl-NHSO₂CH₂CF₃ | MS (ESI) m/z = 549 (MH+, 100%) |
| 1ES | CH₃ | H | H | H | H | H | CH=CH-CH₃ | pyridine-(3,5-bis-CF₃)phenyl | MS (FAB) m/z = 524 (MH+, 100%) |
| 1ET | CH₃ | H | H | H | H | H | CH=CH-CH₃ | pyridine-(3-OH)phenyl | MS (Cl) m/z = 404 (MH+, 100%) [α]$_D^{23}$ = +32.6° (c 0.27, CH₃OH) |

-continued
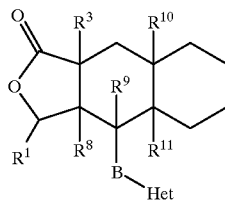
| Ex. | R$^1$ | R$^3$ | R$^8$ | R$^9$ | R$^{10}$ | R$^{11}$ | B | Het | Physical Data |
|---|---|---|---|---|---|---|---|---|---|
| 1EU | CH$_3$ | H | H | H | H | H | CH$_2$CH=CH-CH$_3$ (prop-1-enyl) | 5-(imidazol-2-yl)pyridin-2-yl | MS (ESI) m/z = 378 (MH+, 100%) |
| 1EV | CH$_3$ | H | H | H | H | H | C(OH)(CH$_3$)- | 6-methoxyquinolin-2-yl | HRMS (MH+) found 408.2174 |
| 1EW | CH$_3$ | H | H | H | H | H | CH=CH-CH$_3$ | 6-(acetylamino)quinolin-2-yl | HRMS (MH+) found 419.2331 |
| 1EX | CH$_3$ | H | H | H | H | H | CH=CH-CH$_3$ | 6-(propionylamino)quinolin-2-yl | HRMS (MH+) found 433.2489 |

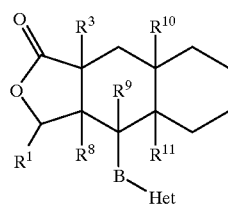
| Ex. | R¹ | R³ | R⁸ | R⁹ | R¹⁰ | R¹¹ | B | Het | Physical Data |
|---|---|---|---|---|---|---|---|---|---|
| 1EY | CH₃ | H | H | H | H | H | CH=CH-CH₃ | quinoline-NHC(O)Ph | HRMS (MH+) found 481.2495 |
| 1EZ | CH₃ | H | H | H | H | H | CH=CH-CH₃ | quinoline-OCH₂-tetrazole | HRMS (MH+) found 460.2335 |
| 1FA | CH₃ | H | H | H | H | H | CH=CH-CH₃ | quinoline-(5-chlorothiophene) | HRMS (MH+) found 478.1611 |

-continued
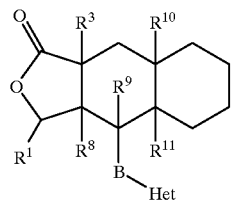
| Ex. | R¹ | R³ | R⁸ | R⁹ | R¹⁰ | R¹¹ | B | Het | Physical Data |
|---|---|---|---|---|---|---|---|---|---|
| 1FB | ◂CH₃ | ◂H | ◂H | H | ◂H | ⋯H | CH=CH-CH₃ | quinolin-2-yl with thiophen-3-yl at 6-position | HRMS (MH+) found 444.1998 |
| 1FC | ◂CH₃ | ◂H | ◂H | H | ◂H | ⋯H | CH=CH-CH₃ | benzo[h]quinolin-3-yl | HRMS (MH+) found 412.2277 |
| 1FD | ⋯CH₃ | ⋯H | ⋯H | H | ⋯H | ◂H | C(=O)NHCH₃ | 6-methylpyridin-2-yl | MS: 323 (M + H) |
| 1FE | ⋯CH₃ | ⋯H | ⋯H | H | ⋯H | ◂H | C(=O)NHCH₃ | 6-methylpyridin-2-yl | MS: 309 (M + 1) |
| 1FF | ⋯CH₃ | ⋯H | ⋯H | H | ⋯H | ◂H | CH₂OCH₃ | 6-methylpyridin-2-yl | HRMS (MH+) found 376.2266 |

-continued

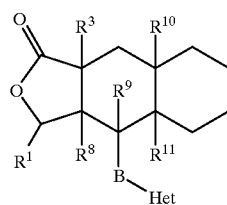

| Ex. | R¹ | R³ | R⁸ | R⁹ | R¹⁰ | R¹¹ | B | Het | Physical Data |
|---|---|---|---|---|---|---|---|---|---|
| 1FG | •••ıııCH₃ | •••ıııH | •••ıııH | H | •••ıııH | ◂H | NH-C(=O)-CH₃ | 6-methylpyridin-2-yl | MS (FAB) m/z = 343 (MH+, 100%) |
| 1FH | ◂CH₃ | ◂H | ◂H | ◂H | ◂H | •••ıııH | CH=CH-CH₃ | 6-(3,5-difluorophenyl)pyridin-2-yl | MS (CI) m/z = 424 (MH+, 100%) |
| 1FI | ◂CH₃ | ◂H | ◂H | ◂H | ◂H | •••ıııH | CH=CH-CH₃ | 6-(2,5-dichlorophenyl)pyridin-2-yl | MS (ESI) m/z = 456 (MH+, 100%) |
| 1FJ | ◂CH₃ | ◂H | ◂H | ◂H | ◂H | •••ıııH | CH=CH-CH₃ | 6-(3-ethoxycarbonylphenyl)pyridin-2-yl | MS (CI) m/z = 460 (MH+, 100%) |

-continued
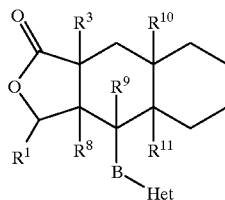
| Ex. | R¹ | R³ | R⁸ | R⁹ | R¹⁰ | R¹¹ | B | Het | Physical Data |
|---|---|---|---|---|---|---|---|---|---|
| 1FK | CH₃ | H | H | H | H | H | CH=CH-CH₃ | 5-(3-(CH₂CO₂Et)phenyl)pyridin-2-yl | MS (ESI) m/z = 474 (MH+, 100%) |
| 1FL | CH₃ | H | H | H | H | H | CH=CH-CH₃ | 5-(3-CN-phenyl)pyridin-2-yl | MS (ESI) m/z = 413 (MH+, 100%) |
| 1FM | CH₃ | H | H | H | H | H | CH=CH-CH₃ | 5-(2-CO₂Et-phenyl)pyridin-2-yl | MS (FAB) m/z = 460 (MH+, 100%) |
| 1FN | CH₃ | H | H | H | H | H | CH=CH-CH₃ | 5-(2,5-difluorophenyl)pyridin-2-yl | MS (ESI) m/z = 424 (MH+, 100%) |

-continued
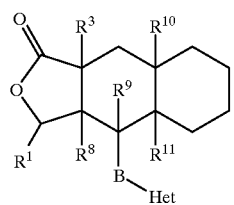
| Ex. | R¹ | R³ | R⁸ | R⁹ | R¹⁰ | R¹¹ | B | Het | Physical Data |
|---|---|---|---|---|---|---|---|---|---|
| 1FO | CH₃ | H | H | H | H | H | CH=CH-CH₃ | pyridine-phenyl-OCF₃ | MS (ESI) m/z = 472 (MH+, 100%) |
| 1FP | CH₃ | H | H | H | H | H | CH=CH-CH₃ | pyridine-(2,6-difluorophenyl) | MS (ESI) m/z = 424 (MH+, 100%) |
| 1FQ | CH₃ | H | H | H | H | H | CH=CH-CH₃ | pyridine-phenyl-SO₂NH₂ | MS (ESI) m/z = 467 (MH°, 100%) |
| 1FR | CH₃ | H | H | H | H | H | CH=CH-CH₃ | pyridine-phenyl-SO₂CH(CH₃)₂ | MS (ESI) m/z = 494 (MH+, 100%) |

-continued
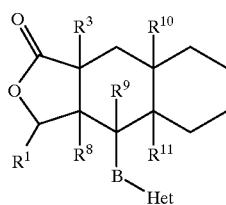
| Ex. | R¹ | R³ | R⁸ | R⁹ | R¹⁰ | R¹¹ | B | Het | Physical Data |
|---|---|---|---|---|---|---|---|---|---|
| 1FS | CH₃ | H | H | H | H | H | CH=CH-CH₃ | 5-(3-bromophenyl)pyridin-2-yl | MS (FAB) m/z = 466 (MH+, 100%) |
| 1FT | CH₃ | H | H | H | H | H | CH=CH-CH₃ | 5-(2,4-difluorophenyl)pyridin-2-yl | MS (FAB) m/z = 424 (MH+, 100%) |
| 1FU | CH₃ | H | H | H | H | H | CH=CH-CH₃ | 5-(2,3,5-trifluorophenyl)pyridin-2-yl | MS (FAB) m/z = 442 (MH+, 100%) |

-continued
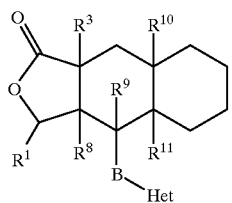
| Ex. | R$^1$ | R$^3$ | R$^8$ | R$^9$ | R$^{10}$ | R$^{11}$ | B | Het | Physical Data |
|---|---|---|---|---|---|---|---|---|---|
| 1FV | CH$_3$ | H | H | H | H | H | CH=CH-CH$_3$ | pyridyl-(3,4-difluorophenyl) | MS (CI) m/z = 424 (MH+, 100%) |
| 1FW | CH$_3$ | H | H | H | H | H | CH=CH-CH$_3$ | pyridyl-(2-hydroxymethylphenyl) | MS (ESI) m/z = 418 (MH+, 100%) |
| 1FX | CH$_3$ | H | H | H | H | H | CH=CH-CH$_3$ | pyridyl-(2-(N(CH$_3$)$_2$)methylphenyl) | MS (ESI) m/z = 445 (MH+, 100%) |
| 1FY | CH$_3$ | H | H | H | H | H | CH=CH-CH$_3$ | pyridyl-(3-(OCH$_2$CH$_2$OH)phenyl) | MS (ESI) m/z = 448 (MH+, 100%) |

-continued
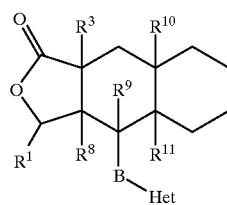
| Ex. | R¹ | R³ | R⁸ | R⁹ | R¹⁰ | R¹¹ | B | Het | Physical Data |
|---|---|---|---|---|---|---|---|---|---|
| 1FZ | CH₃ | H | H | H | H | H | CH=CH-CH₃ | pyridyl-phenyl-OCH₂CH₂OCH₃ | MS (ESI) m/z = 462 (MH+, 100%) |
| 1GA | CH₃ | H | H | H | H | H | CH=CH-CH₃ | pyridyl-phenyl-OCH₂CH₂OCH₂CH₂OH | MS (ESI) m/z = 492 (MH+, 100%) |
| 1GB | CH₃ | H | H | H | H | H | CH=CH-CH₃ | pyridyl-phenyl-OCH₂CH₂OCH₂CH₂OCH₂CH₂OH | MS (ESI) m/z = 536 (MH+, 100%) |
| 1GC | CH₃ | H | H | H | H | H | CH=CH-CH₃ | pyridyl-phenyl-NHSO₂CH₃ | MS (ESI) m/z = 481 (MH+, 100%) |

-continued
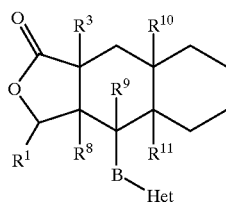
| Ex. | R¹ | R³ | R⁸ | R⁹ | R¹⁰ | R¹¹ | B | Het | Physical Data |
|---|---|---|---|---|---|---|---|---|---|
| 1GD | ◂CH₃ | ◂H | ◂H | ◂H | ◂H | ⋯H | CH=CH-CH₃ | pyridine-phenyl-NH-C(O)-NH-CH₂CH₃ | MS (ESI) m/z = 474 (MH+, 100%) |
| 1GE | ◂CH₃ | ◂H | ◂H | ◂H | ◂H | ⋯H | CH=CH-CH₃ | pyridine-phenyl-C(O)NH₂ | MS (FAB) m/z = 431 (MH+, 100%) |
| 1GF | ◂CH₃ | ◂H | ◂H | ◂H | ◂H | ⋯H | CH=CH-CH₃ | pyridine-phenyl-C(=NH)NH₂ | MS (FAB) m/z = 430 (MH+, 100%) |

EXAMPLE 2

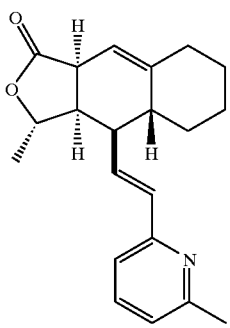

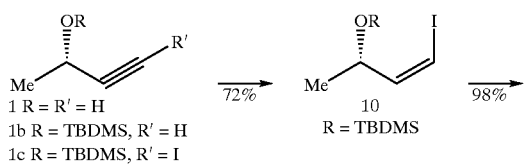

1 R = R' = H
1b R = TBDMS, R' = H
1c R = TBDMS, R' = I

10 R = TBDMS

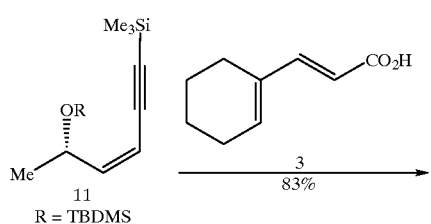

11 R = TBDMS

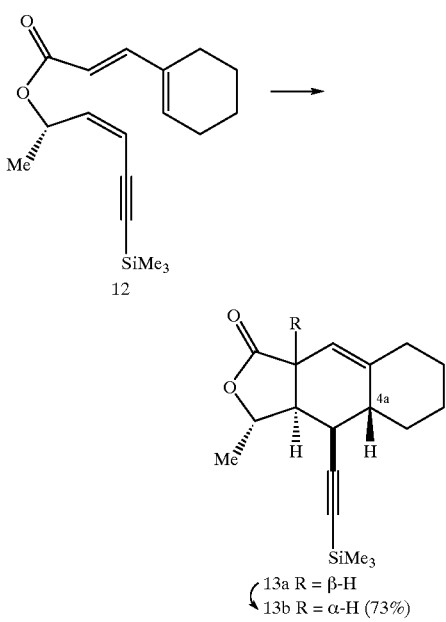

12

13a R = β-H
13b R = α-H (73%)

Step 1: To a solution of compound 1b (4.532 g, 24.6 mmol) in THF (15 ml), cooled to 0° C. under argon, was added a solution of n-BuLi (1.6 M in cyclohexane, 17 ml, 27 mmol). After stirring at 0° C. for 40 min, a solution of $I_2$ (6.24 g, 24.6 mmol) in THF (10 ml) was added and the reaction mixture was stirred for an additional 15 min. The reaction was quenched by addition of water (25 ml) and diluted with hexane (50 ml). The aqueous phase was extracted with hexane (3×50 ml). The combined organic phase was washed with 5% sodium thiosulfate solution (2×50 ml), dried over $MgSO_4$ and evaporated in vacuo to give the acetylenic iodide 1c as an orange oil (7.281 g, 95%).

$[\alpha]_D^{23}$ −48.8 (c 1.23, $CHCl_3$); IR ($CH_2Cl_2$) 2200 $cm^{-1}$; $^1H$ NMR (400 MHz, $CDCl_3$) δ 0.11 (s, 3 H), 0.12 (s, 3 H), 0.90 (s, 9 H, $C(CH_3)_3$), 1.40 (d, J=6.5 Hz, 3 H, $CH_3$), 4.63 (q, J=6.4 Hz, 1 H, CH(OTBS)); $^{13}C$ NMR (100 MHz, $CDCl_3$) δ −4.65, −0.31, 18.21, 25.35, 25.76, 60.50, 96.98.

Step 2: To a solution of cyclohexene (6.8 ml, 67 mmol) in anhydrous pentane (50 ml) stirred at 0° C. under argon was added borane-methyl sulfide complex (2 M in THF, 16.7 ml, 33.4 mmol). The solution was warmed to room temperature and stirred for 1 h to give a cloudy suspension to which was added the acetylenic iodide 1c (8.446 g, 27.2 mmol). The resulting clear solution was stirred at room temperature for 80 min, and glacial acetic acid (5 ml, 87.3 mmol) was added. After stirring the reaction mixture for 20 min, ethanolamine (5.2 ml, 86.2 mmol) was added and stirring was continued for an additional 15 min. The mixture was diluted with EtOAc (300 ml), washed with water (2×100 ml), and brine (100 ml). The organic phase was dried over anhydrous $MgSO_4$ and concentrated in vacuo to yield the crude product as a yellow oil. Purification by column chromatography on silica gel (hexane) gave cis-vinyl iodide 10 as a colorless oil (7.167 g, 84%).

$[\alpha]_D^{23}$ +68.1 (c 0.79, $CHCl_3$); IR (KBr pellet) 1610 $cm^{-1}$; $^1H$ NMR (400 MHz, $CDCl_3$) δ 0.13 (s, 3 H), 0.16 (s, 3 H), 0.95 (s, 9 H, $C(CH_3)_3$), 1.27 (d, J=6.4, 3H, $CH_3$), 4.56 (dq, J=6.4, 6.2 Hz, 1 H, OCH), 6.18 (d, J=7.6 Hz, 1H, HC═C HI), 6.28 (dd, J=7.6, 7.6 Hz, 1 H, CH═CHI); $^{13}C$ NMR (100 MHz, $CDCl_3$) δ −5.15, −4.95, 17.80, 22.37, 25.29, 71.63, 78.25, 145.09.

Step 3: To a solution of $PdCl_2(PhCN)_2$ (58.1 mg, 0.15 mmol) and CuI (58.8 mg, 0.31 mmol) in piperidine (3 ml) was added a solution of the cis-vinyl iodide 10 (303 mg, 0.97 mmol) in anhydrous THF (3 ml). This was followed by addition of (trimethylsilyl)acetylene (0.35 ml, 2.48 mmol) which was accompanied by a color change from dark green to pale green and then to black over 5 min. The solution was stirred at room temperature under argon for 18 h. The solvents were removed in vacuo and the mixture was purified by flash chromatography on silica gel (hexane, followed by 5% EtOAc in hexane) to give the product 11 as a yellow oil (267 mg, 98%).

$[\alpha]_D^{25}$ +128.7 (c 0.745, $CHCl_3$); IR ($CH_2Cl_2$) 2151, 1252 $cm^{-1}$; $^1H$ NMR (400 MHz, $CDCl_3$) δ 0.12 (s, 3 H), 0.15 (s, 3 H), 0.25 (s, 9 H, $Si(CH_3)_3$), 0.95 (s, 9 H, $C(CH_3)_3$), 1.29 (d, J=6.2 Hz, 3 H, $CH_3$), 4.89 (dq, J=8.5, 6.3 Hz, 1 H, OCH), 5.46 (d, J=11.0 Hz, 1 H, CH═C), 5.97 (dd, J=8.5, 11.0 Hz, 1H, C═CH); $^{13}C$ NMR (100 MHz, $CDCl_3$) δ −4.88, −4.58, 1.08, 18.21, 23.61, 25.91, 67.03, 99.53, 101.13, 107.40, 148.86.; MS (Cl/$CH_4$) 283 ($MH^+$), 267, 225.

Step 4: To a solution of the protected enyne 11 (1.744 g, 10.38 mmol) in CH$_3$OH (30 ml) was added TFA (0.6 ml). The reaction mixture was stirred at rt for 2 h. The solvent was removed in vacuo and the residue was diluted with Et$_2$O (40 ml) and water (40 ml). The aqueous phase was extracted with Et$_2$O (3×40 ml), the combined organic phase was washed with brine (50 ml), dried over MgSO$_4$, and concentrated. The final trace of solvent was removed under high vacuum.

To a solution of the deprotected enyne from above in anhydrous CH$_2$Cl$_2$ (30 ml) was added 1-(3-dimethylaminopropyl)-3-ethylcarbodiimide hydrochloride (4.412 g, 23.01 mmol), dimethylaminopyridine (DMAP) (2.836 g, 23.2 mmol), TEMPO (1 mg), and dienoic acid 3 (2.414 g, 15.9 mmol). The reaction mixture was stirred at room temperature under argon for 18 h. The solvents were removed and the mixture was diluted with EtOAc (300 ml). The organic phase was washed with water (150 ml), 0.5 N HCl solution (2×100 ml), and brine (100 ml) and dried over anhydrous MgSO$_4$. Evaporation under reduced pressure yielded the ester 12 as a brown oil (2.601 g, 83%). An analytical sample was prepared by further chromatography on silica gel (5% EtOAc in hexane).

[α]$_D^{25}$+190.7 (c 1.04, CHCl$_3$); IR (CH$_2$Cl$_2$) 2151, 1715 cm$^{-1}$; $^1$H NMR (400 MHz, CDCl$_3$) δ 0.20 (s, 9 H, C(CH$_3$)$_3$), 1.40 (d, J=6.4 Hz, 3 H, CH$_3$), 1.58–1.66 (m, 2 H, CH$_2$), 1.66–1.73 (m, 2 H, CH$_2$), 2.10–2.18 (m, 2 H, CH$_2$), 2.23–2.30 (m, 2 H, CH$_2$), 5.57 (dd, J=11.0, 1.1 Hz, 1 H, C=CH), 5.76 (d, J=15.6 Hz, 1H, CH=C), 5.86 (dq, J=6.44, 7.56 Hz, 1 H, CH=C), 5.97 (dd, J=7.8, 11.0 Hz, 1 H, CH=C), 6.22 (t (broad), J=4.0 Hz, CH=C), 7.31 (s, 1 H, CH=C); 13C NMR (100 MHz, CDCl$_3$) δ –0.203, 19.81, 21.98, 22.01, 24.07, 26.40, 69.02, 100.20, 101.51, 110.35, 114.55, 134.85, 138.77, 143.55, 148.21, 166.65; HRMS (FAB): Calcd for C$_{18}$H$_{27}$O$_2$Si (M$^+$) m/e 302.1702, found m/e 302.1695.

Step 5: To a solution of intermediate 12 (2.125 g, 7.03 mmol) in anhydrous, degassed toluene (25 ml) was added TEMPO (1 mg). The solution was heated in a sealed tube at 185° C. for 2.5 h. The reaction mixture was cooled to room temperature, added DBU (1 ml) and stirred for 30 min. The mixture was diluted with EtOAc (300 ml) and washed with water (100 ml), 0.5 N HCl solution (2×100 ml), and brine (100 ml). The organic phase was dried over anhydrous MgSO$_4$, filtered and evaporated to give the crude product as a yellow oil (2.290 g). Purification by chromatography on silica gel (8% EtOAc in hexane) gave the tricyclic derivative 13b as a pale yellow oil (1.541 g, 73%).

[α]$_D^{21}$+115.6 (c 1.01, CHCl$_3$); IR (CH$_2$Cl$_2$) 2170, 1768 cm$^{-1}$; $^1$H NMR (400 MHz, CDCl$_3$) δ 0.21 (s, 9 H, Si(CH$_3$)$_3$), 0.98 (dddd, J=12.0, 10.5, 10.5, 3.5 Hz, 1 H, C$_5$H$_{ax}$), 0.92–1.04 (m, 1 H, CH), 1.23–1.36 (m, 1 H), 1.40–1.54 (m, 1 H), 1.66 (d, J=6.1 Hz, 3 H, CH$_3$), 1.78–1.94 (m, 2 H), 1.96–2.15 (m, 2 H), 2.31–2.44 (m, 2 H), 2.54–2.68 (m, 2 H), 3.23–3.29 (m, 1 H, C(O)CH), 4.52–4.62 (m, 1 H, OCH(CH$_3$), 5.35 (d, J=2.2 Hz, 1 H, C=CH); $^{13}$C NMR (100 MHz, CDCl$_3$) δ –0.10, 21.29, 25.80, 26.79, 32.94, 33.18, 34.87, 38.16, 43.49, 44.73, 77.67, 88.22, 107.05, 113.12, 142.13, 175.75; HRMS (FAB) Calcd for C$_{18}$H$_{27}$O$_2$Si (MH$^+$) m/e 303.1780, found m/e 303.1775.

Step 6:

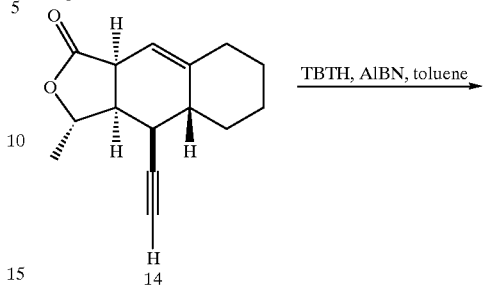

Alkyne 14 (1 g), generated by desilylation of 13b using K$_2$CO$_3$ in CH$_3$OH, was dissolved in toluene (20 ml) in the presence of tributyltin hydride (1.75 ml) and AIBN (100 mg), and the mixture heated at 120° C. for 2 h. The solution was poured onto a column of silica gel, and the desired product eluted with EtOAc-hexane (5:95).

$^1$H-NMR (CDCl$_3$): δ 0.8–0.9 (m, 9H); 1.2–1.6 (m); 3.2 (m, 1H); 4.5 (m, 1H); 5.3 (s, 1H); 5.75 (dd, J=8.3, 18 Hz, 1H); 6.05 (d, J=18 Hz, 1H).

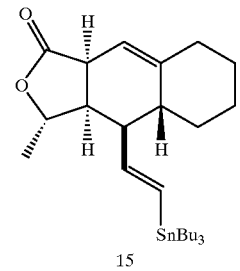

Step 7:

A solution of 15 (224 mg), 6-bromopicoline (356 mg), and Pd(PPh$_3$)$_4$ (50 mg) in toluene (4 ml) was heated overnight in pressure tube at 120° C. The resulting solution was poured onto a column of silica gel and the title compound eluted with EtOAc-hexane (5:95 to 10:90) mixtures.

$^1$H-NMR (CDCl$_3$): δ 1.35 (d, 6 Hz, 3H); 2.46 (s, 3H); 3.2 (m, 1H); 4.5 (m, 1H); 5.3 (s, 1H); 6.5 (m, 2H); 6.9 (d, 1H); 7.1 (d, 1H); 7.5 (t, 1H).

Using a similar procedure, compounds of the following structure are prepared, wherein the variables are as defined in the following Table 2:

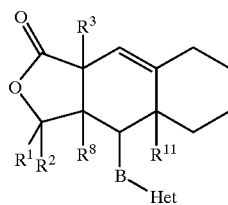

| Ex. | R¹ | R² | R³ | R⁸ | R¹¹ | B | Het | Physical Data |
|---|---|---|---|---|---|---|---|---|
| 2A | ·······CH₃ | H | ·······H | ·······H | ◄─H | CH=CH-CH₃ | tetrahydroquinoline with methyl | MS: 378 (M + H⁺) |
| 2B | ◄─CH₃ | H | ◄─H | ◄─H | ·······H | C≡C-CH₃ | 6-chloropyridin-3-yl | MS: 342 (M + H⁺) |
| 2C | ◄─CH₃ | H | ◄─H | ◄─H | ·······H | C=C=CH-CH₃ | 6-chloropyridin-3-yl | MS: 344 (M + H⁺) |
| 2D | ·······CH₃ | H | ·······H | ·······H | ◄─H | — | quinolin-7-yl | MS: 334 (M + H⁺) |
| 2E | ·······CH₃ | H | ·······H | ·······H | ◄─H | CH=CH-CH₃ | 6-methylpyridin-2-yl | MS: 324 (M + H⁺) |

-continued
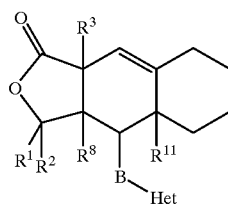
| Ex. | R¹ | R² | R³ | R⁸ | R¹¹ | B | Het | Physical Data |
|---|---|---|---|---|---|---|---|---|
| 2F | ⋯CH₃ | H | ⋯H | ⋯H | ◄H | CH=CH-CH₃ | 2-pyridyl | MS: 310 (M + H⁺) |
| 2G | ⋯CH₃ | H | ⋯H | ⋯H | ◄H | CH=CH-CH₃ | 3-pyridyl | MS: 310 (M + H⁺) |
| 2H | ⋯CH₃ | H | ⋯H | ⋯H | ◄H | CH=CH-CH₃ | 5-pyrimidyl | MS: 311 (M + H⁺) |
| 2I | ⋯CH₃ | H | ⋯H | ⋯H | ◄H | CH=CH-CH₃ | 2-thiazolyl | MS: 316 (M + H⁺) |
| 2J | ⋯CH₃ | H | ⋯H | ⋯H | ◄H | CH₂CH₂CH₂CH₃ | 6-methyl-2-pyridyl | MS: 326 (M + H⁺) |
| 2K | ⋯CH₃ | H | ⋯H | ⋯H | ◄H | CH=CH-CH₃ | 2-pyrazinyl | MS: 311 (M + H⁺) |

-continued
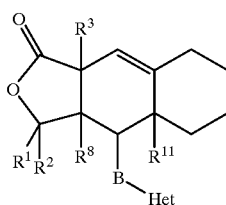
| Ex. | R[1] | R[2] | R[3] | R[8] | R[11] | B | Het | Physical Data |
|---|---|---|---|---|---|---|---|---|
| 2L | ·····CH₃ | H | ·····H | ·····H | ◄─H | CH=CH−CH₃ | 2-quinolinyl | MS: 360 (M + H⁺) |
| 2M | ·····CH₃ | H | ·····H | ·····H | ◄─H | — | 6-quinolinyl | MS: 334 (M + H⁺) |
| 2N | ·····CH₃ | H | ·····H | ·····H | ◄─H | — | 4-pyridyl | MS: 284 (M + H⁺) |
| 2O | ·····CH₃ | H | ·····H | ·····H | ◄─H | CH=CH−CH₃ | 3-quinolinyl | MS: 360 (M + H⁺) |
| 2P | ·····CH₃ | H | ·····H | ·····H | ◄─H | CH=CH−CH₃ | 4-isoquinolinyl | MS: 360 (M + H⁺) |

-continued
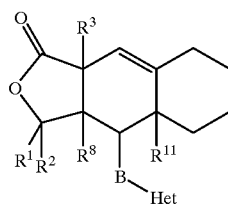
| Ex. | R¹ | R² | R³ | R⁸ | R¹¹ | B | Het | Physical Data |
|---|---|---|---|---|---|---|---|---|
| 2Q | ....ıCH₃ | H | ....ııH | ....ııH | ◄H | CH=CH | benzoxazol-2-yl | MS: 350 (M + H⁺) |
| 2R | ....ıCH₃ | H | ....ııH | ....ııH | ◄H | CH=CH | 6-methoxypyridin-2-yl | MS: 340 (M + H⁺) |
| 2S | ....ıCH₃ | H | ....ııH | ....ııH | ◄H | CH=CH | 3-methylquinolin-2-yl | MS: 374 (M + H⁺) |
| 2T | ....ıCH₃ | H | ....ııH | ....ııH | ◄H | CH=CH | 4-methylquinolin-2-yl | MS: 374 (M + H⁺) |
| 2U | ....ıCH₃ | H | ....ııH | ....ııH | ◄H | CH=CH | 6-methylpyridin-3-yl | MS: 324 (M + H⁺) |

-continued
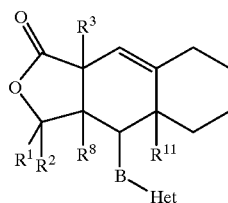
| Ex. | R¹ | R² | R³ | R⁸ | R¹¹ | B | Het | Physical Data |
|---|---|---|---|---|---|---|---|---|
| 2V | ⋯CH₃ | H | ⋯H | ⋯H | ◄H | CH=CH-CH₃ | 4-quinolinyl | MS: 360 (M + H⁺) |
| 2W | ⋯CH₃ | H | ⋯H | ⋯H | ◄H | CH=CH-CH₃ | 5,6,7,8-tetrahydroquinolin-4-yl | MS: 364 (M + H⁺) |
| 2X | ⋯CH₃ | H | ⋯H | ⋯H | ◄H | CH=CH-CH₃ | 6-vinylpyridin-2-yl | MS: 336 (M + H⁺) |
| 2Y | ⋯CH₃ | H | ⋯H | ⋯H | ◄H | CH=CH-CH₃ | 2-ethyl-3-methylpyridin-6-yl | MS: 352 (M + H⁺) |
| 2Z | ⋯CH₃ | H | ⋯H | ⋯H | ◄H | CH=CH-CH₃ | 5,6,7,8-tetrahydroquinolin-2-yl | MS: 364 (M + H⁺) |

-continued
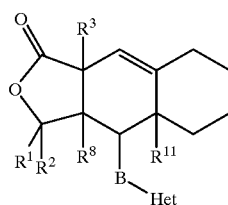
| Ex. | R¹ | R² | R³ | R⁸ | R¹¹ | B | Het | Physical Data |
|---|---|---|---|---|---|---|---|---|
| 2AA | ⸺CH₃ | H | ⸺H | ⸺H | ◂H | CH=CH-CH₃ | 6-methoxy-4-methylquinolin-2-yl | MS: 404 (M + H⁺) |
| 2AB | ⸺CH₃ | H | ⸺H | ⸺H | ◂H | CH=CH-CH₃ | 5,6-dimethylpyridin-2-yl | MS: 338 (M + H⁺) |
| 2AC | ⸺CH₃ | H | ⸺H | ⸺H | ◂H | CH=CH-CH₃ | 6,7,8,9-tetrahydro-5H-cyclohepta[b]pyridin-2-yl | MS: 378 (M + H⁺) |
| 2AD | ⸺CH₃ | H | ⸺H | ⸺H | ◂H | CH=CH-CH₃ | 5-cyanopyridin-2-yl | MS: 335 (M + H⁺) |

-continued
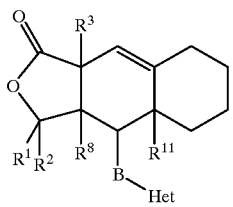
| Ex. | R¹ | R² | R³ | R⁸ | R¹¹ | B | Het | Physical Data |
|---|---|---|---|---|---|---|---|---|
| 2AE | ⋯CH₃ | H | ⋯H | ⋯H | ◀H | CH=CH(CH₃) | 6-isopropylquinolin-2-yl | MS: 402 (M + H⁺) |
| 2AF | ⋯CH₃ | H | ⋯H | ⋯H | ◀H | CH=CH(CH₃) | 6,7-dihydro-5H-cyclopenta[b]pyridin-2-yl | MS: 350 (M + H⁺) |
| 2AG | ⋯CH₃ | H | ⋯H | ⋯H | ◀H | CH=CH(CH₃) | 5-(trifluoromethyl)pyridin-2-yl | MS: 378 (M + H⁺) |
| 2AH | ⋯CH₃ | H | ⋯H | ⋯H | ◀H | CH=CH(CH₃) | 6-(methoxymethyl)pyridin-2-yl | MS: 354 (M + H⁺) |
| 2AI | ⋯CH₃ | H | ⋯H | ⋯H | ◀H | CH=CH(CH₃) | 6-methylpyridazin-3-yl | MS: 325 (M + H⁺) |

-continued
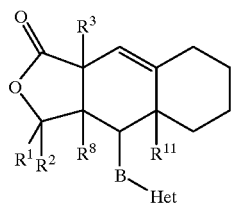
| Ex. | R¹ | R² | R³ | R⁸ | R¹¹ | B | Het | Physical Data |
|---|---|---|---|---|---|---|---|---|
| 2AJ | ⋯CH₃ | H | ⋯H | ⋯H | ◄H | CH=CH (vinyl) | quinolin-7-yl | MS: 360 (M + H⁺) |
| 2AK | ⋯CH₃ | H | ⋯H | ⋯H | ◄H | C=C=C (allenyl) | quinolin-7-yl | MS: 360 (M + H⁺) |
| 2AL | CH₃CH₂ | H | ⋯H | ⋯H | ◄H | CH=CH | quinolin-2-yl | MS: 374 (M + H⁺) |
| 2AM | ⋯CH₃ | H | ⋯H | ⋯H | ◄H | CH=CH | quinoxalin-2-yl | MS: 361 (M + H⁺) |
| 2AN | ⋯CH₃ | H | ⋯H | ⋯H | ◄H | CH=CH | 6-(methoxymethyl)pyridin-2-yl | MS: 368 (M + H⁺) |

-continued

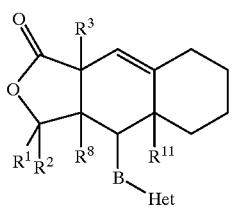

| Ex. | R¹ | R² | R³ | R⁸ | R¹¹ | B | Het | Physical Data |
|---|---|---|---|---|---|---|---|---|
| 2AO | —CH₃ | —CH₃ | ·····''H | ·····''H | ◄─H | CH=CH(CH₃)— | 2-quinolinyl | MS: 374 (M + H⁺) |
| 2AP | ·····''CH₃ | H | ·····''H | ·····''H | ◄─H | CH=CH(CH₃)— | 1-methyl-2-indolyl | MS: 362 (M + H⁺) |
| 2AQ | ·····''CH₃ | H | ·····''H | ·····''H | ◄─H | CH=CH(CH₃)— | 6-(2,2,2-trifluoroethoxymethyl)pyridin-2-yl | MS: 422 (M + H⁺) |
| 2AR | ·····''CH₃ | H | ·····''H | ·····''H | ◄─H | allene (C=C=C(CH₃)) | 6-(2,2,2-trifluoroethoxymethyl)pyridin-2-yl | HRMS found: 422.1944 |
| 2AS | ·····''CH₃ | H | ·····''H | ·····''H | ◄─H | CH=CH(CH₃)— | 4-(methoxycarbonyl)quinolin-2-yl | MS: 418 (M + H⁺) |
| 2AT | ·····''CH₃ | H | ·····''H | ·····''H | ◄─H | CH=CH(CH₃)— | 6-(2-methoxyethyl)pyridin-2-yl | HRMS found: 368.2224 |

-continued

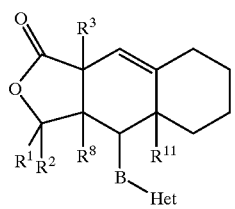

| Ex. | R¹ | R² | R³ | R⁸ | R¹¹ | B | Het | Physical Data |
|---|---|---|---|---|---|---|---|---|
| 2AU | ⋯CH₃ | H | ⋯H | ⋯H | ◂H | CH=CH (with methyl) | quinoline-4-carboxylic acid, 2-yl | HRMS (M + H⁺) found: 404.1858 |
| 2AV | ⋯CH₃ | H | ⋯H | ⋯H | ◂H | CH=CH (with methyl) | 6-(methylthio)pyridin-2-yl | HRMS (M + H⁺) found: 356.1685 |
| 2AW | ⋯CH₃ | H | ⋯H | ⋯H | ◂H | CH=CH (with methyl) | 2-(methylthio)pyridin-4-yl | HRMS (M + H⁺) found: 356.1685 |
| 2AX | ⋯CH₃ | H | ⋯H | ⋯H | ◂H | CH=CH (with methyl) | 5-phenylpyridin-2-yl | HRMS (M + H⁺) found: 386.2115 |
| 2AY | ⋯CH₃ | H | ⋯H | ⋯H | ◂H | CH=CH (with methyl) | 6-propylpyridin-2-yl | HRMS (M + H⁺) found: 352.2274 |

-continued

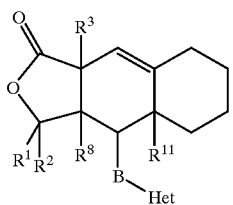

| Ex. | R¹ | R² | R³ | R⁸ | R¹¹ | B | Het | Physical Data |
|---|---|---|---|---|---|---|---|---|
| 2AZ | ....ıııCH₃ | H | ....ıııH | ....ıııH | ◀H | CH=CH-CH₃ | 6-ethylpyridin-2-yl | HRMS (M + H⁺) found: 338.2113 |
| 2BA | ....ıııCH₃ | H | ....ıııH | ....ıııH | ◀H | CH₃-C=C | 6-ethylpyridin-2-yl | HRMS (M + H⁺) found: 338.2110 |
| 2BB | ....ıııCH₃ | H | ....ıııH | ....ıııH | ◀H | CH=CH-CH₃ | 2-methyl-3-phenylpyridin-6-yl | HRMS (M + H⁺) found: 400.2273 |
| 2BC | ....ıııCH₃ | H | ....ıııH | ....ıııH | ◀H | CH=CH-CH₃ | 6,7-dimethoxyquinolin-2-yl | HRMS (M + H⁺) found: 420.2181 |
| 2BD | ....ıııCH₃ | H | ....ıııH | ....ıııH | ◀H | CH=CH-CH₃ | 2-ethyl-3-phenylpyridin-6-yl | HRMS (M + H⁺) found: 414.2432 |

-continued
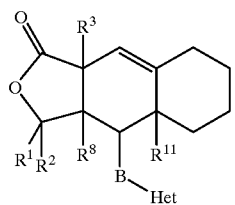
| Ex. | R¹ | R² | R³ | R⁸ | R¹¹ | B | Het | Physical Data |
|---|---|---|---|---|---|---|---|---|
| 2BE | ⋯CH₃ | H | ⋯H | ⋯H | ◀H | C=C (allene) | 5-phenyl-6-ethyl-pyridin-2-yl | HRMS (M + H⁺) found: 414.2432 |
| 2BF | H | H | ⋯H | ⋯H | ◀H | CH=CH(CH₃) | quinolin-2-yl | HRMS (M + H⁺) found: 346.1811 |
| 2BG | H | H | ⋯H | ⋯H | ◀H | CH=CH(CH₃) | 6-methyl-pyridin-2-yl | HRMS (M + H⁺) found: 310.1808 |
| 2BH | ⋯CH₂CH₃ | H | ⋯H | ⋯H | ◀H | CH=CH(CH₃) | 6-methyl-pyridin-2-yl | HRMS (M + H⁺) found: 338.2127 |
| 2BI | ⋯CH₃ | H | ⋯H | ⋯H | ◀H | CH=CH(CH₃) | 6-isopropyl-quinolin-2-yl | HRMS (M + H⁺) found: 416.2593 |

-continued

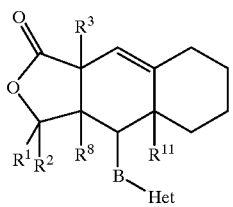

| Ex. | R¹ | R² | R³ | R⁸ | R¹¹ | B | Het | Physical Data |
|---|---|---|---|---|---|---|---|---|
| 2BJ | ⋯CH₃ | H | ⋯H | ⋯H | ◂H | CH=CH(CH₃) | 5-phenyl-pyridin-2-yl | HRMS (M + H⁺) found: 386.2215 |
| 2BK | ⋯CH₃ | H | ⋯H | ⋯H | ◂H | CH=CH(CH₃) | 3-phenyl-pyridin-2-yl | HRMS (M + H⁺) found: 386.2115 |
| 2BL | ⋯CH₃ | H | ⋯H | ⋯H | ◂H | CH=CH(CH₃) | 6-pentyl-pyridin-2-yl | HRMS (M + H⁺) found: 380.2594 |
| 2BM | ⋯CH₃ | H | ⋯CH₃ | ⋯H | ◂H | CH=CH(CH₃) | 6,7-dimethoxy-quinolin-2-yl | HRMS (M + H⁺) found: 434.2331 |
| 2BN | ⋯CH₃ | H | ⋯H | ⋯H | ◂H | C=C=C (allene) | 6-methyl-[1,3]dioxolo[4,5-g]quinolin-7-yl | HRMS (M + H⁺) found: 404.1867 |

-continued
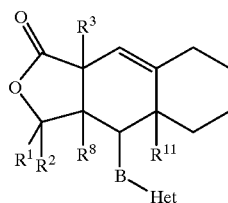
| Ex. | R¹ | R² | R³ | R⁸ | R¹¹ | B | Het | Physical Data |
|---|---|---|---|---|---|---|---|---|
| 2BO | ⋯CH₃ | H | ⋯H | ⋯H | ◀H | CH=CH(CH₃) | 2-quinolinyl-6,7-methylenedioxy | HRMS (M + H⁺) found: 404.1871 |
| 2BP | ⋯CH₃ | H | ⋯H | ⋯H | ◀H | CH=CH(CH₃) | benzo[f]quinolin-3-yl | HRMS (M + H⁺) found: 410.2126 |
| 2BQ | ⋯CH₃ | H | ⋯H | ⋯H | ◀H | C=C=CH(CH₃) | benzo[f]quinolin-3-yl | HRMS (M + H⁺) found: 410.2122 |
| 2BR | ⋯CH₃ | H | ⋯H | ⋯H | ◀H | CH=CH(CH₃) | 5-phenylpyridin-2-yl | HRMS (M + H⁺) found: 400.2269 |

-continued
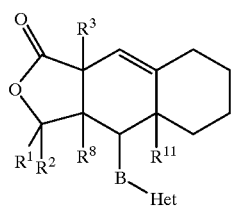
| Ex. | R¹ | R² | R³ | R⁸ | R¹¹ | B | Het | Physical Data |
|---|---|---|---|---|---|---|---|---|
| 2BS | ⋯CH₃ | H | ⋯H | ⋯H | ◀H | CH=CH (with CH₃) | 4-phenylquinolin-2-yl | HRMS (M + H⁺) found: 436.2271 |
| 2BT | ⋯CH₃ | H | CH₃CH₂ | ⋯H | ◀H | CH=CH (with CH₃) | quinolin-2-yl | MS: 388 (M + H⁺) |
| 2BU | ⋯CH₃ | H | ⋯CH₃ | ⋯H | ◀H | CH=CH (with CH₃) | 1,10-phenanthrolin-3-yl | HRMS (M + H⁺) found: 411.2072 |
| 2BV | ⋯CH₃ | H | CH₂OH | ⋯H | ◀H | CH=CH (with CH₃) | quinolin-2-yl | HRMS (M + H⁺) found: 390.2064 |

-continued
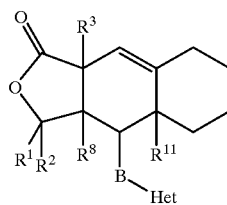
| Ex. | R¹ | R² | R³ | R⁸ | R¹¹ | B | Het | Physical Data |
|---|---|---|---|---|---|---|---|---|
| 2BW | ⋯CH₃ | H | CH₂=CHCH₂⋯ | ⋯H | ◄H | CH=CH(CH₃) | 2-quinolinyl | HRMS (M + H⁺) found: 400.2293 |
| 2BX | ⋯CH₃ | H | ⋯CH₃ | ⋯H | ◄H | CH=CH(CH₃) | 2-quinolinyl | HRMS (M + H⁺) found: 374.2107 |
| 2BY | ⋯CH₃ | H | ⋯H | ⋯H | ◄H | CH=CH(CH₃) | 6-(N-benzylcarboxamido)-3-pyridyl | HRMS (M + H⁺) found: 443.2336 |
| 2BZ | ⋯CH₃ | H | benzyl | ⋯H | ◄H | CH=CH(CH₃) | 2-quinolinyl | HRMS (M + H⁺) found: 450.2445 |

-continued
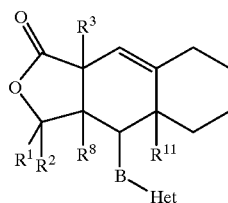
| Ex. | R¹ | R² | R³ | R⁸ | R¹¹ | B | Het | Physical Data |
|---|---|---|---|---|---|---|---|---|
| 2CA | ⋯CH₃ | H | ⋯H | ⋯H | ◀H | CH=CH-CH₃ | 5-(phenoxymethyl)pyridin-2-yl | MS: 416 (M +H⁺) |
| 2CB | ⋯CH₃ | H | ⋯H | ⋯H | ◀H | C=CH-CH₃ | 5-(benzyloxy)quinolin-2-yl | HRMS (M + H⁺) found: 466.2373 |
| 2CC | ⋯CH₃ | H | CH₂COOH | ⋯H | ◀H | CH=CH-CH₃ | quinolin-2-yl | HRMS (M + H⁺) found: 418.2022 |
| 2CD | ⋯CH₃ | H | ⋯H | ⋯H | ◀H | CH=CH-CH₃ | 5-(benzyloxy)-6-methylpyridin-2-yl | HRMS (M + H⁺) found: 430.2375 |

-continued
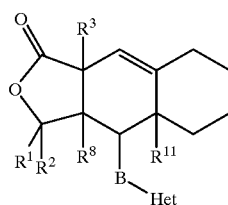
| Ex. | R¹ | R² | R³ | R⁸ | R¹¹ | B | Het | Physical Data |
|---|---|---|---|---|---|---|---|---|
| 2CE | ...CH₃ | H | ...H | ...H | —H | C=C | 5-benzyloxy-6-methylpyridin-2-yl | MS: 430 (M + H⁺) |
| 2CF | ...CH₃ | H | ...H | ...H | —H | CH=CH(CH₃) | 6-(N-benzoylamino)pyridin-3-yl | MS: 429 (M + H⁺) |
| 2CG | ...CH₃ | H | CH₂CO₂CH₃ | ...H | —H | CH=CH(CH₃) | quinolin-2-yl | MS: 432 (M + H⁺) |
| 2CH | ...CH₃ | H | ...H | ...H | —H | CH=CH(CH₃) | 6-(N-cyclohexylcarbamoyl)pyridin-3-yl | MS: 435 (M + H⁺) |

-continued

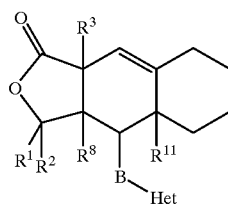

| Ex. | R¹ | R² | R³ | R⁸ | R¹¹ | B | Het | Physical Data |
|---|---|---|---|---|---|---|---|---|
| 2CI | ·····ıCH₃ | H | CH(CH₃)CH₂CH₃ (isobutyl) | ·····ıH | ◄═H | CH=CH-CH₃ | 2-quinolinyl | MS: 416 (M + H⁺) |
| 2CJ | ·····ıCH₃ | H | ·····ıH | ·····ıH | ◄═H | CH=CH-CH₃ | 6-(N-phenylcarbamoyl)-pyridin-3-yl | MS: 429 (M + H⁺) |
| 2CK | ·····ıCH₃ | H | ·····ıH | ·····ıH | ◄═H | CH=CH-CH₃ | 6-(phenylsulfonamido)-pyridin-2-yl | MS: 465 (M + H⁺) |
| 2CL | ·····ıCH₃ | H | ·····ıH | ·····ıH | ◄═H | CH=CH-CH₃ | benzo[g]quinolin-2-yl | HRMS (M + H⁺) found: 410.2130 |

-continued

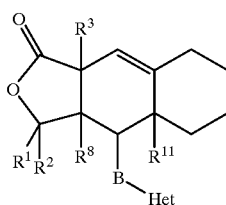

| Ex. | R[1] | R[2] | R[3] | R[8] | R[11] | B | Het | Physical Data |
|---|---|---|---|---|---|---|---|---|
| 2CM | ·····ıııCH₃ | H | H₃C̶ O̶H | ·····ıııH | ◂H | CH=CH(CH₃) | 2-quinolinyl | HRMS (M + H⁺) found: 404.2226 |
| 2CN | ·····ıııCH₃ | H | ·····ıııH | ·····ıııH | ◂H | CH=CH(CH₃) | 5-methoxy-2-quinolinyl | HRMS (M + H⁺) found: 390.2071 |
| 2CO | ·····ıııCH₃ | H | ·····ıııH | ·····ıııH | ◂H | CH=CH(CH₃) | 5-methoxy-2-quinolinyl | HRMS (M + H⁺) found: 404.2231 |
| 2CP | ·····ıııCH₃ | H | ·····ıııH | ·····ıııH | ◂H | CH=CH(CH₃) | 5-benzyloxy-2-quinolinyl | HRMS (M + H⁺) found: 466.2377 |

-continued

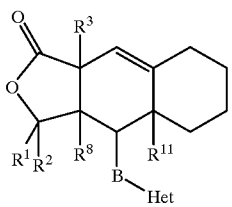

| Ex. | R¹ | R² | R³ | R⁸ | R¹¹ | B | Het | Physical Data |
|---|---|---|---|---|---|---|---|---|
| 2CQ | ••••ılCH₃ | H | ••••ıllH | | ••••ıllH | ⟵H | (butyl group) | (5-methoxyquinolin-2-yl) | HRMS (M + H⁺) found: 392.2223 |
| 2CR | ••••ılCH₃ | H | H₃C-C(CH₃)(CH₃)-O-C(=O)-CH₂- | ••••ıllH | ⟵H | CH=CH (vinyl) | (quinolin-2-yl) | MS: 474 (M + H⁺) |
| 2CS | ••••ılCH₃ | H | ••••ıllH | | ••••ıllH | ⟵H | HN-C(=O)-CH₂- | (6-methylpyridin-2-yl) | MS (FAB): 343 (MH⁺, 100%) |

EXAMPLE 3

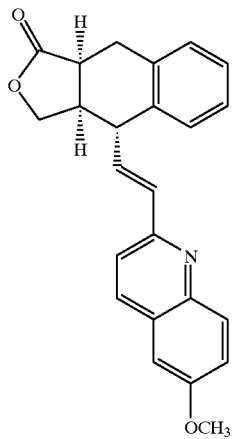

The compound numbers used in the following steps correspond to those shown in reaction Scheme 3, above.

Step 1: A solution of THP-ether 18 (2.8 g, 20 mmol) in dry THF (100 ml) was cooled to −78° C. and n-BuLi (25 mmol, 10 ml, 2.5N in hexanes) was added dropwise. After 15 min at that temperature, benzyl chloroformate (3.75 ml, 25 mmol, 95% pure) was added dropwise. The resulting solution was stirred at −78° C. for 2 h and the reaction quenched by addition of NH₄Cl (sat. sol). After reaching room temperature, the reaction mixture was diluted with Et₂O (50 ml) and washed with brine. The organic phase was dried (MgSO₄) and solvents removed in rotavapor, yielding 7.0 g of crude ester 19. ¹H NMR (CDCl₃) δ 1.3–2.0 (m, 6H), 3.6–3.9 (m, 2H), 4.45 (s, 2H), 5.27 (s, 2H), 7.40 (m, 5H).

Step 2: Crude THP-ether 19 (7.0 g) was dissolved in CH₃OH (15 ml) and a catalytic amount of PTSA (250 mg) added at room temperature. After 15 min, the solution was diluted with Et₂O and brine, and the organic phase washed with NaHCO₃ (sat. sol.) and brine, and dried (MgSO₄). Solvents were removed in rotavapor, yielding 4.6 g of crude alcohol 20. ¹H NMR (CDCl₃) δ 4.45 (s, 2H), 5.27 (s, 2H), 7.40 (m, 5H).

Step 3: Crude alcohol 20 (4.6 g) was dissolved in CH₂Cl₂ (50 ml) containing DMAP (catalytic amounts) and Et₃N (3 ml) at 0° C. Cinnamoyl chloride (3.3 g, 20 mmol) was added and the mixture stirred at 0° C. for 30 min. The resulting suspension was diluted with Et$_2$O and water, and the organic phase successively washed with NaOH (10%, 50 ml), HCl (2N, 50 ml) and brine, dried (MgSO$_4$) and the solvents removed in rotavapor, yielding crude ester 21 (7.2 g). $^1$H NMR (CDCl$_3$) δ 5.0 (s, 2H), 5.27 (s, 2H), 6.50 (d, J=16 Hz, 1H), 7.40–7.70 (m,10H), 7.80 (d, J=16 Hz, 1H).

Step 4: A solution of cinnamic ester 21 (7.2 g) in o-xylene (50 ml) was degassed with Ar and heated at 190° C. in pressure tube for 18 h. The mixture was cooled down, and the solvent removed in rotavapor. After chromatographic purification, lactone 22 (3.0g, 44% yield from ether 18) was obtained. $^1$H NMR (CDCl$_3$) δ 3.62 (m,1H), 3.78 )d, J=15.2 Hz, 1H), 4.08 (t, J=8.8 Hz,1H), 4.68 (t, J=8.8 Hz, 1H), 5.34 (d, J=12.0 Hz, 1H), 5.42 (d, J=12 Hz, 1H), 7.2–7.5 (m, 10H).

Step 5: Lactone 22 (0.9 g) was dissolved in CH$_3$OH (40 ml) and hydrogenated under 60 psi of total pressure in the presence of PtO$_2$ (150 mg) for 14 h. The catalyst was filtered off through a celite bed, and the solvent removed in rotavapor. Acid 23 (270 mg, 41%) crystallizes from EtOAc and hexanes. $^1$H-NMR (CDCl$_3$) δ 2.93 (dd, 3.2; 15.3 Hz, 1H), 3.52 (dd, J=7.8; 15.3 Hz, 1H), 3.23 (m, 1H), 3.55 (m, 1H), 3.61 (d, J=3.2 Hz, 1H), 3.7 (dd, J=5.5; 9.5 Hz, 1H), 4.44 (t, J=9.2 Hz, 1H), 7.1–7.2 (m, 4H).

Step 6: Carboxylic acid 23 (0.18 g) was suspended in CH$_2$Cl$_2$ (5 mL) containing (COCl)$_2$ (0.15 ml) under an N$_2$ atmosphere at room temperature. A drop of DMF was added and the resulting mixture stirred at room temperature for 1 h. Solvents were removed in rotavapor, and the crude solid obtained was washed twice with toluene, removing the solvent in rotavapor. A white solid results, which was treated with a solution of toluene (5 ml) and tributyltin hydride (0.3 ml) containing catalytic amounts of Pd(PPh$_3$)$_4$ at 0° C. After 2 h, the mixture was diluted with Et$_2$O and the organic phase washed with brine. Chromatographic purification afforded aldehyde 24 (95 mg, 56% yield) as a solid. $^1$H-NMR (CDCl$_3$) δ 2.75 (ddd, 1.0; 7.1; 15.5 Hz, 1H), 3.52 (dd, J=2.3; 15.5 Hz, 1H), 3.5 (m, 1H), 3.64 (d, J=1.8 Hz, 1H), 3.78 (m, 1H), 3.83 (dd, J=4.7; 9.2 Hz, 1H), 4.55 (t, J=9.1 Hz, 1H), 7.2–7.4 (m, 4H); 9.56 (s, 1H).

Step 7: A solution of phosphonate 25 (125 mg, 0.45 mmol) in dry THF (10 ml) at 0° C. was treated with n-BuLi (0.2 ml, 0.5 mmol, 2.5N in hexanes). After 15 min, a solution of aldehyde 24 (95 mg) in dry THF was added. The resulting solution was stirred at that temperature for 30 min, and diluted with Et$_2$O and brine. The organic phase was washed with brine and dried (MgSO$_4$). Solvents are removed in rotavapor, and chromatographic purification affords the title compound (50 mg, 32%).

$^1$H-NMR (CDCl$_3$): δ 8.35 (d, J=8.5 Hz, 1H); 8.0 (d, J=9.4 Hz, 1H); 7.54 (d, J=8.6 Hz, 1H); 7.42 (dd, J=2.9; 9.2, 1H); 7.28–7.36 (m, 4H); 7.11 (d, J=2.8 Hz, 1H); 6.94 (dd, J=7.6; 15.9 Hz, 1H); 6.78 (d, J=15.9 Hz, 1H); 4.56 (dd, J=8.3; 9.4 Hz, 1H); 4.18 (dd, J=4.4; 9.4 Hz, 1H); 4.0 (s, 3H); 3.6 (t, J=7.3Hz,1H). $^{13}$C-NMR (CDCl$_3$): 179.4; 157.6; 152.5; 143.9; 137.3; 135.2; 135.1; 133.9; 133.6; 130.5; 128.3; 127.5; 127.3; 126.9; 122.3; 119.3; 105.0; 71.5; 55.4; 45.6; 39.0; 38.4; 28.7.

Using a similar procedure, compounds of the following structural formulas were prepared, wherein the variables are as defined in the table:

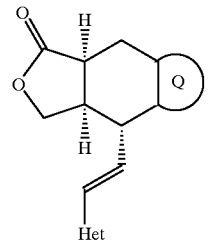

| Ex. | Q | Het | Physical Data |
|---|---|---|---|
| 3A | 4-OCH$_3$, 3-substituted phenyl | 6-OCH$_3$ quinolin-2-yl | MS m/z 430(18), 403(28), 402(100), 401(14) |
| 3B | 2-CH$_3$ substituted phenyl | 6-OCH$_3$ quinolin-2-yl | HRMS (MH$^+$) found: 386.1756 |
| 3C | 4-OCH$_3$, 3-substituted phenyl | 5-(3-CF$_3$-phenyl)pyridin-2-yl | HRMS (MH$^+$) found: 466.1625 |
| 3D | 2-OCH$_3$ substituted phenyl | 6-OCH$_3$ quinolin-2-yl | HRMS (MH$^+$) found: 402.1709 |

| | | |
|---|---|---|
| 3E | 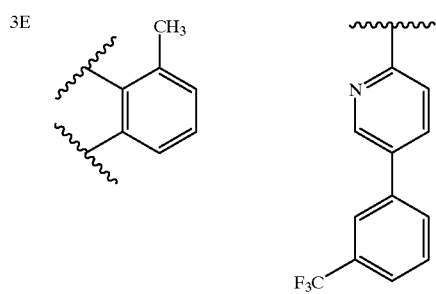 | HRMS (MH+) found: 450.1684 |
| 3F | 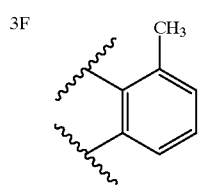 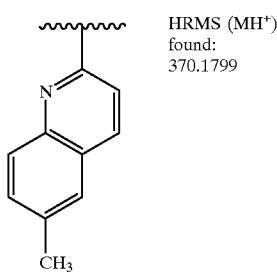 | HRMS (MH+) found: 370.1799 |
| 3G | 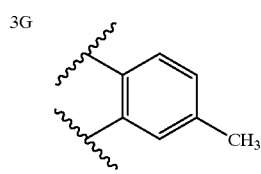 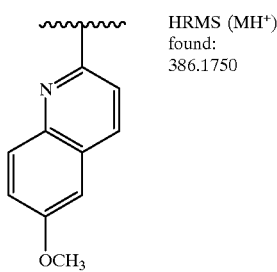 | HRMS (MH+) found: 386.1750 |
| 3H | 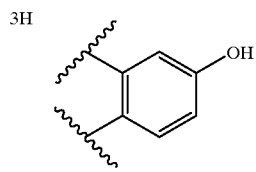 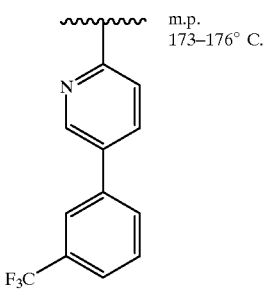 | m.p. 173–176° C. |
| 3I | | HRMS (MH+) found: 454.1427 |
| 3J | 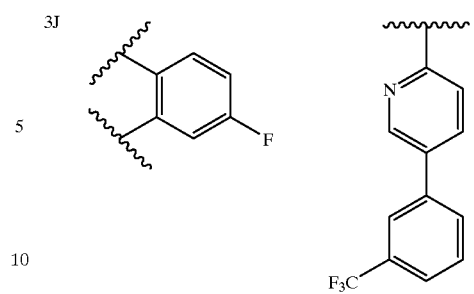 | HRMS (MH+) found: 454.1423 |
| 3K | 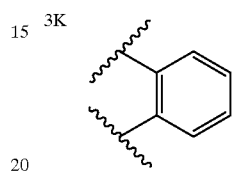 | HRMS (MH+) found: 436.1533 |
| 3L | | HRMS (MH+) found: 472.1332 |
Using a similar procedure, the following compound, 3M, is prepared:
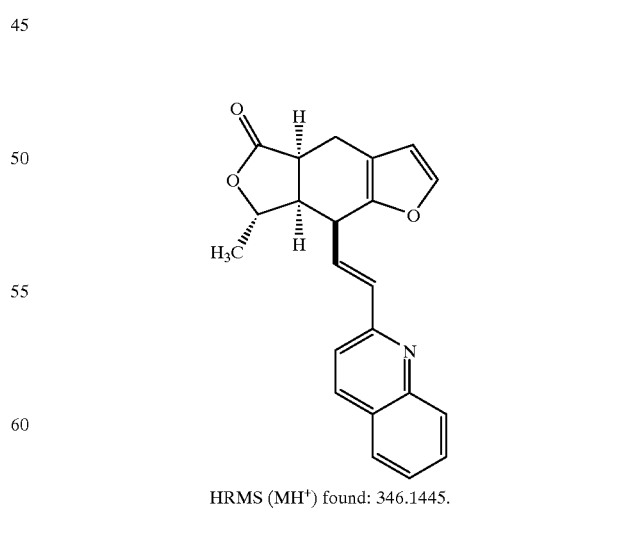
HRMS (MH+) found: 346.1445.

EXAMPLE 4

(+)-(3R,3aS,4S,4aR,8aS,9aR)-Decahydro-4-[(E)-2-[5-[3-(trifluoromethyl)phenyl]-2-pyridinyl]ethenyl]-3-Methylnaphtho-[2,3-c]furan-1(3H)-one

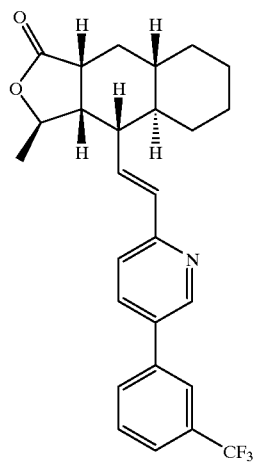

Step 1:

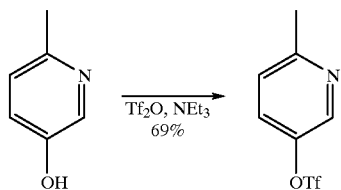

Triflic anhydride (46 ml, 0.275 mol) was added dropwise to a stirred solution of 3-hydroxy-6-methylpyridine (10 g, 0.092 mol) in pyridine (200 ml) at 0° C. and stirred at 0° C. to room temperature for 16 h. The mixture was poured into ice-water (300 ml) and extracted with Et$_2$O. The Et$_2$O layer was washed with water (2×150 ml) and brine, dried (MgSO$_4$), and concentrated in vacuo to give the desired product (18.7 g, 83%) as a brown oil. $^1$H NMR (400 MHz, CDCl$_3$) δ 2.67 (s, 3H), 7.32 (d, 1H, J=8.5 Hz), 7.57 (dd, 1H, J=8.6, 2.8 Hz), 8.53 (d, 1H, J=2.8 Hz). MS (ESI) m/z 242 (MH$^+$, 100%); Anal. calc'd for C$_7$H$_6$F$_3$NO$_3$S: C, 34.86; H, 2.51; N, 5.81. Found: C, 35.24; H, 2.48; N, 5.54.

Step 2:

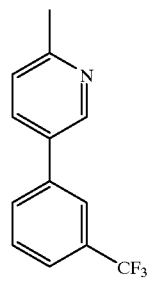

To a solution of the product of Step 1 (8.5 g, 34.5 mmol) and 3-trifluoromethylphenylboronic acid (10 g, 55 mmol) in toluene (100 ml) was added EtOH (25 ml), K$_2$CO$_3$ (14.3 g, 104 mmol) in H$_2$O (50 ml) and Pd(PPh$_3$)$_4$ (400 mg, 0.345 mmol). The mixture was heated in a closed pressure tube under Ar at 120° C. for 16 h. The mixture was diluted with EtOAc, washed with 5% NaOH and brine, dried (MgSO$_4$), and concentrated in vacuo. Flash chromatography of the residue on a silica gel column with EtOAc:hexane (10:90, then 20:80) as eluent gave the desired product (6.7 g, 82%) as yellow solids. $^1$H NMR (400 MHz, CDCl$_3$) δ 2.68 (s, 3H), 7.32 (d, 1H, J=8 Hz), 7.62–7.90 (m, 5H), 8.79 (d, 1H, J=2 Hz). Anal. calc'd for C$_{13}$H$_{10}$F$_3$N.0.10 H$_2$O: C, 65.32; H, 4.30; N, 5.86. Found: C, 65.27; H, 4.44; N, 5.78.

Step 3:

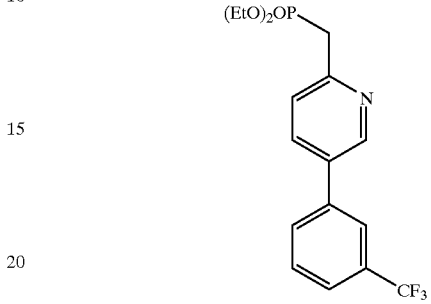

Using a procedure similar to that described in Example 1, Step 8, treat the product of Step 2 to obtain the desired product (8.84 g, 85%) as a tan oil. $^1$H NMR (400 MHz, CDCl$_3$) δ 1.36 (t, 6H, J=7 Hz), 3.56 (d, 2H, J=22 Hz), 4.19 (dq, 4H, J=7,7 Hz), 7.58–7.96 (m, 6H), 8.84 (d, 1H, J=2 Hz); MS (FAB) m/z 374 (MH$^+$, 100%); Anal. calc'd for C$_{17}$H$_{19}$F$_3$NO$_3$P.0.25 H$_2$O: C, 54.04; H, 5.20; N, 3.71. Found: C, 54.22; H, 5.54; N, 3.93.

Step 4: Treat the product of Step 3 in a manner similar to that described in Example 1, Step 9, to obtain the title compound.

$^1$H NMR (400 MHz, CDCl$_3$) δ 0.83–2.03 (m, 12H), 1.49 (d, 3H, J=6 Hz), 2.38–2.51 (m, 2H), 2.72–2.81 (m, 1H), 4.79–4.88 (m, 1H), 6.57–6.73 (m, 2H), 7.30–7.95 (m, 6H), 8.85 (d,1H, J=2 Hz); MS (FAB) m/z 456 (MH$^+$, 100%). HCl salt: off-white solids; [α]$^{22}$D=+17.0° (c 0.33, MeOH); Anal. calc'd for C$_{27}$H$_{28}$F$_3$NO$_2$.HCl.0.50 H$_2$O: C, 64.73; H, 6.04; N, 2.80. Found: C, 64.57; H, 6.32; N, 2.94.

The product of Example 4 is treated as described below to obtain the compounds of Examples 4A, 4B and 4C:

4A

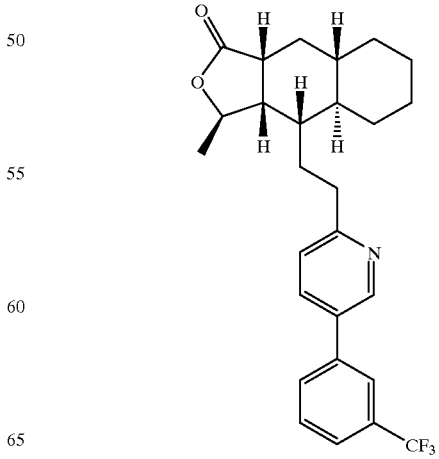

4B
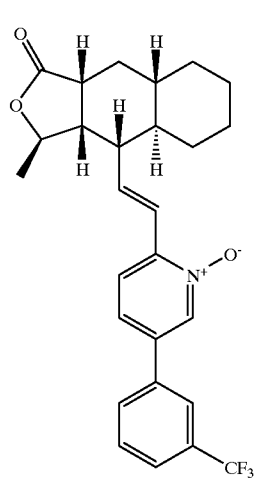

4D
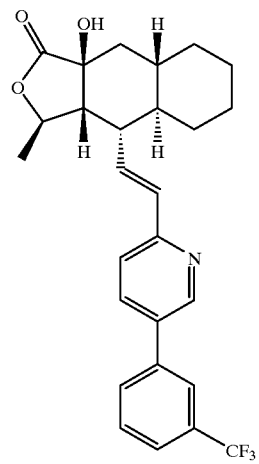

4C
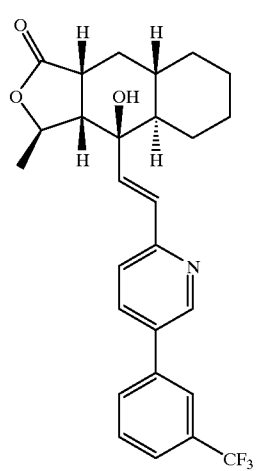

4E

4A: The product of Example 4 (21 mg, 0.050 mmol) was stirred under $H_2$ (1 atm) over Pd/C (30 mg) in $CH_3OH$ (10 mL) at room temperature for 8 h. The mixture was filtered and the filtrate was concentrated in vacuo to obtain 4A (52 mg, 88%) as semi-solids. $[\alpha]^{22}_D = -35.1°$ (c 0.69, MeOH); MS (FAB) m/z 458 (MH$^+$, 100%).

4B: To a solution of the product of Example 4 (20 mg, 0.044 mmol) in $CH_2Cl_2$ (1 mL) was added m-CPBA (11 mg, 0.066 mmol) at room temperature. The mixture was stirred at room temperature for 16 h. The mixture was diluted with $CH_2Cl_2$, washed with $NaHCO_3$ (sat.), dried ($MgSO_4$), and concentrated in vacuo. Preparative TLC separation of the residue with $CH_2Cl_2$:$CH_3OH$ (95:5) as eluent gave 4B (19 mg, 91%) as off-white solids. $[\alpha]^{24}_D = +23.3°$ (c 0.43, $CH_3OH$); MS (ESI) m/z 472 (MH$^+$, 100%).

4C: The product of Example 4 (21 mg, 0.050 mmol) was heated with $SeO_2$ (0.2 mg, 0.23 mmol) in 1,4-dioxane (2 mL) at reflux for 40 min. The mixture was concentrated in vacuo. Preparative TLC separation of the residue with EtOAc:hexane (40:60) as eluent gave 4C (17 mg, 80%) as white solids. $[\alpha]^{20}_D = +42.8°$ (c 0.65, $CH_3OH$); MS (FAB) m/z 472 (MH$^+$, 100%).

The product of Example 4 is treated as described below to obtain the compounds of Example 4D and 4E:

4D: LiN(TMS)$_2$ (0.6 mL, 0.60 mmol) was added to a solution of the product of Example 4 (227 mg, 0.50 mmol) in dry THF (5 mL) at −78° C. and stirred at −78° C. for 30 min. and at room temperature for 1 h. A solution of (10-camphorsulfonyl)oxaziridine (137 mg, 0.60 mmol) in dry THF (2 mL) was added at −78° C. and stirred at −78° C. for 30 min. and at room temperature for 2 h. The mixture was neutralized with saturated NH$_4$Cl solution and extracted with EtOAc. The organic layer was washed with brine, dried, and concentrated in vacuo. Flash chromatography of the residue on a silica gel column with EtOAc: hexane (40:60) as eluent gave 4D (100 mg). MS: 472 (MH$^+$).

4E: LiN(TMS)$_2$ (0.6 mL, 0.60 mmol.) was added to a solution of the product of Example 4 (227 mg, 0.50 mmol) in dry THF (5 mL) at −78° C. and stirred at −78° C. for 30 min. and at room temperature for 1 h. A mixture of paraformaldehyde (225 mg, 2.5 mmol) in dry THF (2 mL) was added at −78° C. and stirred at −78° C. for 30 min and at room temperature for 2 days. The mixture was neutralized with saturated NH$_4$Cl solution and extracted with EtOAc. The organic layer was washed with brine, dried, and concentrated in vacuo. Flash chromatography of the residue on a silica gel column with EtOAc:hexane (40:60) as eluent gave 4E (30 mg). MS: 486 (MH$^+$).

EXAMPLE 5

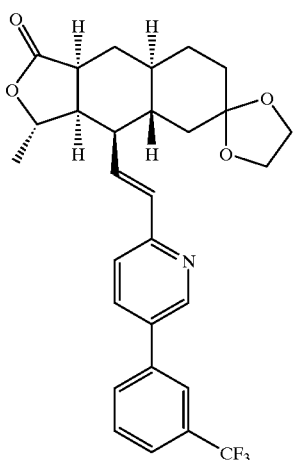

Step 1:

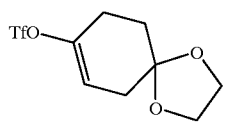

To a solution of 1,4-cyclohexanedione mono-ethylene ketal (10 g, 64 mmol) and 2,6-di-tert-butyl-4-methylpyridine (21 g, 102 mmol) in $CH_2Cl_2$ (350 mL) at room temperature was added triflic anhydride (16 mL, 96 mmol) and the mixture was stirred for 16 h. The mixture was washed with $NaHCO_3$ (sat.). The organic layer was dried ($MgSO_4$) and concentrated in vacuo. Flash chromatography of the residue on a silica gel column with EtOAc:hexane (5:95 then 10:90) as eluent gave the desired product (13.4 g, 72%) as a clear oil.

Step 2:

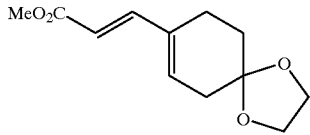

To a solution of the product of Step 1 (13 g, 46 mmol) in DMF (150 mL) was added methyl acrylate (8.4 mL, 92 mmol), $Et_3N$ (19 mL, 138 mmol), and $Pd(PPh_3)_2Cl_2$ (1.62 g, 2.3 mmol). The mixture was stirred at 75° C. for 10 h. The mixture was diluted with $NH_4Cl$ (sat.) and extracted with ether. The organic layer was washed with brine, dried ($MgSO_4$), and concentrated in vacuo. Flash chromatography of the residue on a silica gel column with EtOAc:hexane (15:85) as eluent gave the desired product (9.15 g, 89%) as a clear oil.

Step 3:

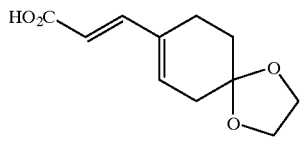

To a solution of the product of Step 2 (9.15 g, 40 mmol) in THF: $CH_3OH$ (450 mL, 1:1) was added NaOH (225 mL, 10%). The mixture was stirred at room temperature for 3 h. The mixture was diluted with water, washed with $CH_2Cl_2$, acidified with 10% HCl, and extracted with EtOAc. The organic layer was washed with brine, dried ($MgSO_4$), and concentrated in vacuo to give the desired compound (8.00 g, 95%) as light-yellow solids.

Step 4:

The product of Step 3 was treated in a manner similar to that described in Example 1, steps 3 through 6 and 9 to obtain the title compound (racemate) as off-white solids; MS (ESI) m/z 514 (MH$^+$, 100%).

The product of Example 5 is treated as described below to obtain the compounds of Examples 5A, 5B and 5C:

5A

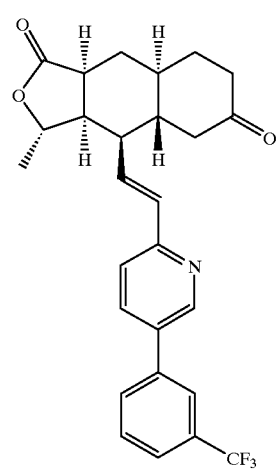

5B

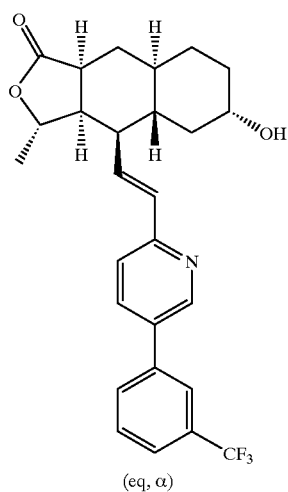

(eq, α)

-continued

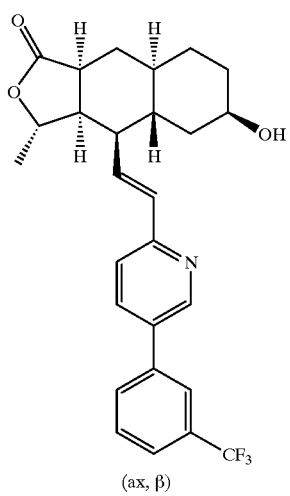

5C (ax, β)

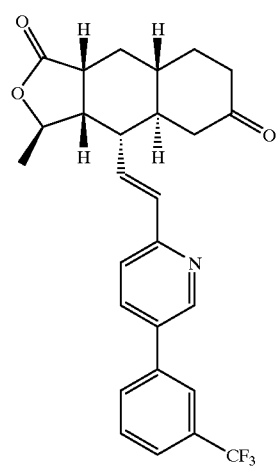

5D

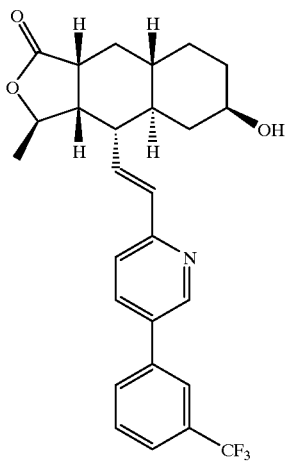

5E

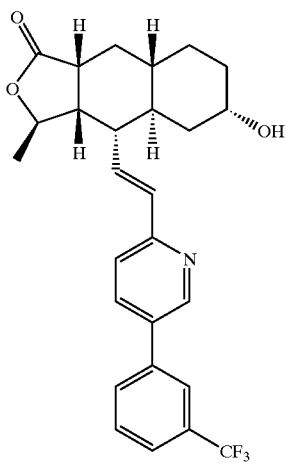

5F

5A: A mixture of the compound of Example 5 (65 mg, 0.13 mmol) and HCl (2 mL, 5%) in acetone (2 mL) was stirred at reflux temperature for 16 h. The mixture was neutralized with NaHCO$_3$ (sat.) and extracted with EtOAc. The organic layer was washed with brine, dried (MgSO$_4$) and concentrated in vacuo. Preparative TLC separation of the residue with EtOAc:hexane (40:60) as eluent gave 5A (42 mg, 71%), the HCl salt, as white solids. MS (FAB) m/z 470 (MH$^+$, 100%).

5B: To a solution of 5A (70 mg, 0.15 mmol) in THF:CH$_3$OH (10 mL, 1:1) was added NaBH$_4$ (11 mg, 0.30 mmol). The mixture was stirred at room temperature for 10 min. The mixture was diluted with NH$_4$Cl (sat.) and extracted with EtOAc. The organic layer was washed with brine, dried (MgSO$_4$) and concentrated in vacuo. Preparative TLC separation of the residue with EtOAc:hexane (60:40) as eluent gave 5B (39 mg, 55%), the HCl salt, as white solids. MS (FAB) m/z 472 (MH$^+$, 100%).

5C: To a solution of 5A (70 mg, 0.15 mmol) in dry THF (5 mL) was added K-Selectride® (0.23 mL, 0.23 mmol, 1.0 M in THF) at −78° C. The mixture was stirred at −78° C. for 1.5 h. The mixture was diluted with NH$_4$Cl (sat.) and extracted with EtOAc. The organic layer was washed with brine, dried (MgSO$_4$) and concentrated in vacuo. Preparative TLC separation of the residue with EtOAc:hexane (60:40) as eluent gave 5C (45 mg, 63%), the HCl salt, as white solids. MS (FAB) m/z 472 (MH$^+$, 100%).

Compounds 5D, 5E and 5F are prepared in a manner similar to that described for Examples 5A–5C using enantiomerically pure starting materials:

5D: MS: 470 (MH$^+$); 5E: MS: 472 (MH$^+$); 5F: MS: 472 (MH$^+$)

From 5D, the following compounds 5G and 5H can be prepared by conventional methods known to those skilled in the art:

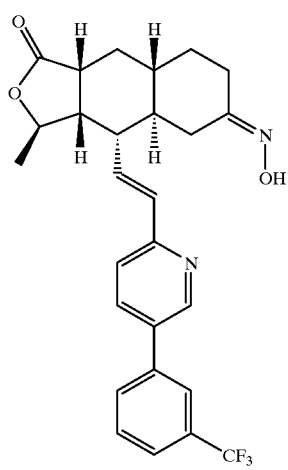

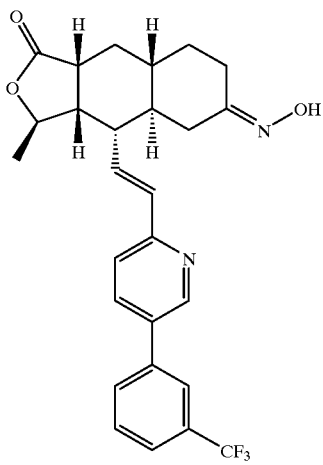

5G: MS: 485 (MH+); 5H: MS: 485 (MH+).

EXAMPLES 6, 6A, 6B, 6C

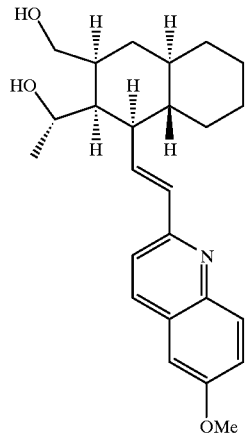

6: To a stirred solution of Example 1AB (0.91 g, 2.3 mmol) in dry THF (20 mL) at room temperature was added LAH (0.18 g, 4.6 mmol) in portions. The mixture was stirred at room temperature for 30 min. NaOH (10%, 0.50 mL) was added dropwise, followed by EtOAc (50 mL) and MgSO$_4$ powders. The mixture was stirred vigorously for 10 min and filtered. The filtrate was concentrated in vacuo to give the title compound (0.88 g, 96%) as white solids. MS (FAB) m/z 396 (MH+, 100%).

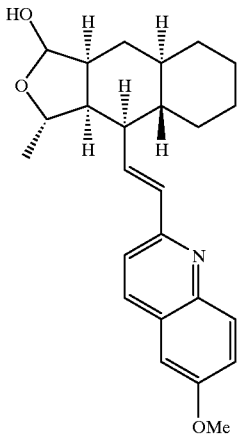

6A: To a solution of Example 1AB (0.200 g, 0.511 mmol) in dry toluene (10 mL) at −78° C. was added DIBAL (0.76 mL, 0.77 mmol, 1.0 M in toluene) dropwise and the mixture was stirred at −78° C. for 1.5 h. EtOAc was added and stirred to room temperature. Water was added and stirred vigorously for 1 h. The organic layer was separated and the aqueous layer was extracted with EtOAc. The combined organic layers were dried (MgSO$_4$) and concentrated in vacuo. Flash chromatography of the residue on a silica gel column with EtOAc:hexane (30:70) as eluent gave the title compound (0.100 g, 50%) as white solids. MS (FAB) m/z 394 (MH+, 100%).

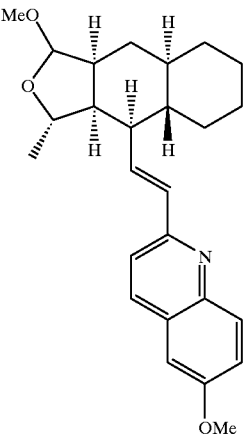

6B: To a solution of Example 6A (50 mg, 0.13 mmol) in CH$_3$OH (20 mL) at 0° C. was added BF$_3$.OEt$_2$ (31 mL, 0.26 mmol) dropwise and the mixture was stirred at 0° C. to room temperature for 3 h. CH$_3$OH was concentrated in vacuo. The residue was partitioned between EtOAc and NaHCO₃ (sat.). The organic layer was dried (MgSO₄) and concentrated in vacuo. Preparative TLC separation of the residue with EtOAc:hexane (20:80) as eluent gave the title compound (30 mg). HCl salt: off-white solids. MS (FAB) m/z 408 (MH⁺, 100%).

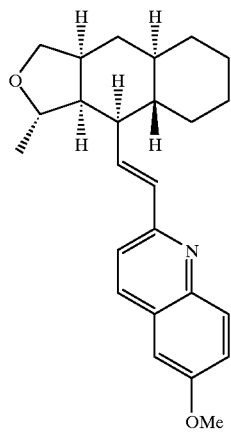

6C: To a solution of Example 6A (50 mg, 0.13 mmol) in CH₂Cl₂ (20 mL) at −78° C. was added BF₃.OEt₂ (31 mL, 0.26 mmol) and Et₃SiH (0.24 mL, 1.3 mmol). The mixture was stirred at −78° C. to room temperature for 3 h. The mixture was partitioned between CH₂Cl₂ and NaHCO₃ (sat.). The organic layer was dried (MgSO₄) and concentrated in vacuo. Preparative TLC separation of the residue with EtOAc:hexane (20:80) as eluent gave the title compound (38 mg). HCl salt: off-white solids. MS (FAB) m/z378 (MH⁺, 100%).

EXAMPLES 7, 7A, 7B

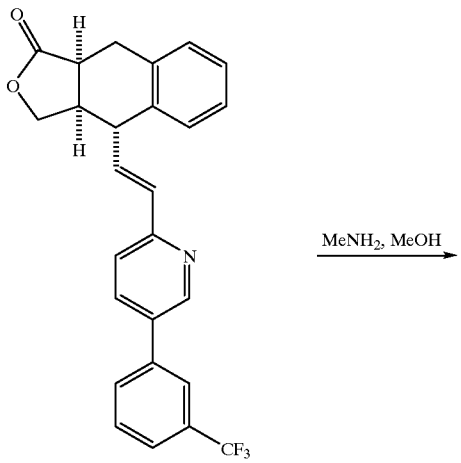

MeNH₂, MeOH →

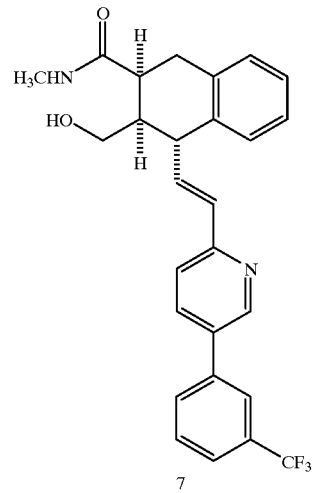

7

7. The lactone, prepared in a manner similar to Example 3, (75 mg, 0.17 mmol) was dissolved in a 2.0 M solution of CH₃NH₂ in CH₃OH (3.0 mL) and stirred under N₂ at room temperature for 1 h. At that time, tlc showed no starting material left, as well as the presence of a more-polar spot. The solution is dissolved in Et₂O (30 mL) and extracted with brine (30 mL×2), dried (Na₂SO₄) and the solvents removed in rotary evaporator. The title compound (Example 7) was obtained as a white solid (70 mg, 86%). ¹H-NMR (CDCl₃) δ 2.5 (m, 1H); 2.82 (d, J=4.6 Hz, 3H); 3.0 (dd, J=5.4; 16.8 Hz, 1H); 3.07 (m, 1H); 3.25 (dd, J=10.1; 16.8 Hz, 1H); 3.67 (dd, J=5.5; 11.6 Hz, 1H); 3.79 (m, 1H); 3.89 (dd, J=8.0; 11.4 Hz, 1H); 6.33 (d, J=15.6 Hz, 1H); 6.49 (m, 1H); 6.95 (dd, J=7.0; 15.6 Hz, 1H); 7.2 (m, 4H); 7.25 (d, J=8.2 Hz, 1H); 7.64 (t, J=7.6 Hz, 1H); 7.70 (d, J=7.9,1H); 7.78 (d, J=7.6, 1H); 7.82 (m, 2H); 8.73 (d, J=1.8 Hz, 1H).

¹³C-NMR (CDCl₃): 175.93; 154.80; 147.57; 139.59; 138.22; 134.93; 134.79; 134.24; 133.43; 130.81; 130.57; 130.07; 129.58; 129.11; 126.74; 126.30; 124.68; 123.50; 121.74; 62.52; 44.54; 42.89; 39.58; 28.66; 26.40. MS: 467 (M+1). HRMS: 467.1947 (calc.: 467.1946).

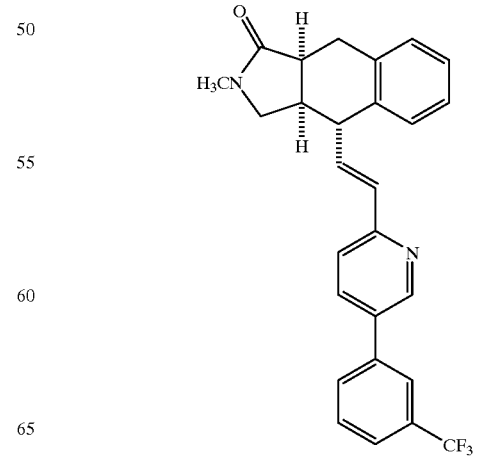

7A: The product of Example 7 (40 mg) was dissolved in dry CH$_2$Cl$_2$ (3 mL) under N$_2$ atmosphere and SOCl$_2$ (0.1 mL) was added dropwise via syringe. The solution was stirred at room temperature for 1 h. The reaction was quenched by addition of NaHCO$_3$ (sat. sol., 15 mL). The aqueous suspension was extracted with Et$_2$O (3×30 mL). The organic fractions are combined and washed with brine, dried (Na$_2$SO$_4$) and taken to dryness in rotary evaporator. The title compound (35 mg, 91%) was obtained as a white solid. $^1$H-NMR (CDCl$_3$): δ 2.82 (m, 1H); 3.0 (dd, J=6.4; 14.7 Hz, 1H); 3.04 (s, 3H); 3.23 (m, 1H); 3.30 (dd, J=8.2; 14.7 Hz, 1H); 3.48 (t, 7.9 Hz, 1H); 4.20 (dd, J=4.4; 9.3Hz, 1H), 4.48 (dd, J=7.8; 9.2 Hz, 1H); 6.70 (d, J=15.6 Hz, 1H); 7.0 (dd, J=8.4; 15.6 Hz, 1H); 7.25–7.35 (m, 4H); 7.43 (d, J=7.7 Hz, 1H); 7.64 (t, J=7.6 Hz, 1H); 7.72 (d, J=7.6,1H); 7.83 (d, J=7.4,1H); 7.88 (s, broad, 1H); 8.73 (dd, J=2.4; 8.1Hz, 1H); 8.84 (d, J=1.8 Hz, 1H).
$^{13}$C-NMR (CDCl$_3$): 167.21; 154.36; 148.03; 138.42; 138.18; 136.28; 135.01; 134.89; 133.77; 132.32; 130.15; 129.63; 128.26; 127.07; 126.88; 126.56; 124.74; 124.70; 123.72; 123.68; 121.84; 73.17; 45.12; 40.88; 39.01; 34.18; 30.79. MS: 449 (M+1). HRMS: 449.1842 (calc.: 449.1841).

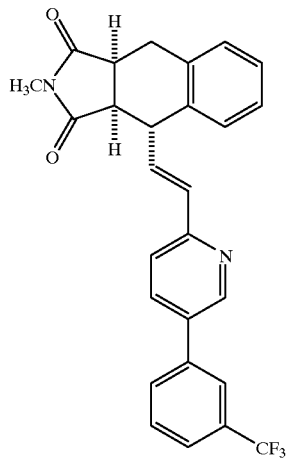

7B: The crude product of Example 7 (45 mg) was dissolved in acetone (2 mL) at 0 ° C. under N$_2$ atmosphere. Jones reagent was added dropwise until its red color persisted. The reaction was quenched by dropwise addition of ethanol until red color was fully discharged. The resulting green suspension was diluted with Et$_2$O and water, and the organic phase washed with brine, dried (MgSO$_4$) and the solvents removed in rotavapor. The crude acid was dissolved in dry CH$_2$Cl$_2$ (5 mL) under N$_2$ atmosphere and SOCl$_2$ (0.1 mL) added dropwise via syringe. The solution was stirred at room temperature for 1 h. The reaction was quenched by addition of NaHCO$_3$ (sat. sol., 15 mL). The aqueous suspension was extracted with Et$_2$O (3×30 mL). The organic fractions were combined and washed with brine, dried (Na$_2$SO$_4$) and taken to dryness in rotary evaporator. After flash chromatography (30% EtOAc in hexanes) the desired imide (35 mg, 77%) was obtained. $^1$H-NMR (CDCl$_3$): δ 2.86 (s, 3H); 3.20 (m, 2H); 3.5 (m, 1H); 3.58 (dd, J=1.8; 9.2 Hz, 1H); 4.4 (m, 1H); 6.38 (dd, J=1.2; 15.6 Hz, 1H); 7.10 (dd, J=5.2; 15.6 Hz,1H); 7.2–7.4 (m, 5H); 7.65 (t, J=7.7 Hz, 1H); 7.72 (d, J=7.6, 1H); 7.8 (d, J=7.6,1H); 7.86 (s, 1H); 7.92 (d, J=8.2 Hz, 1H); 8.86 (s, 1H). MS: 463 (M+1). HRMS: 463.1634 (calc.: 463.1633).

EXAMPLE 8

(+)-(3R,3aS,4S,4aR,8aS,9aR)-Decahydro-4-[(E)-2-(6-ethyl-2-pyridinyl)ethenyl]-3-methylnaphtho[2,3-c]furan-1(3H)-one

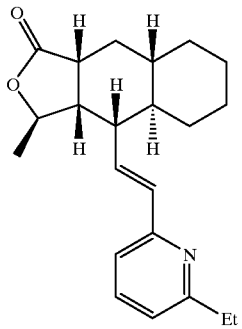

Step 1: Preparation of

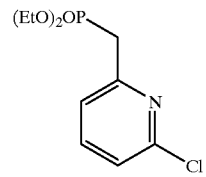

Using a procedure similar to that of Example 1, Step 8, 2-chloro-6-methylpyridine was treated with diethylchlorophosphate to obtain a clear oil.

$^1$H NMR (400 MHz, CDCl$_3$) δ 1.34 (t, 6H, J=7 Hz), 3.43 (d, 2H, J=22 Hz), 4.15 (dq, 4H, J=7, 7 Hz), 7.27 (dd,1H, J=8, 2 Hz), 7.38 (dd,1H, J=8,2 Hz), 7.66 (t, 1H, J=8 Hz); MS (FAB) m/z 264 (MH$^+$, 100%).

Step 2: Preparation of

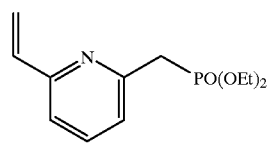

To a solution of the product of Step 1 (5.24 g, 19.9 mmol) in anhydrous THF (100 mL) was added Pd(PPh$_3$)$_4$ (1.2 g, 1.0 mmol) and vinyltributyltin (8.72 mL, 29.9 mmol). The mixture was heated in a closed pressure tube under Ar at 120° C. for 16 h. The aqueous layer was neutralized with 10% NaOH and solid NaHCO$_3$ and extracted with CH$_2$Cl$_2$. The organic layer was dried (MgSO$_4$) and concentrated in vacuo. Flash chromatography of the residue on a silica gel column with EtOAc:hexane (40:60 then 80:20) as eluent gave the desired product (3.66 g, 72%) as a clear oil. $^1$H NMR (400 MHz, CDCl$_3$) δ 1.32 (t, 6H, J=7 Hz), 3.48 (d, 2H, J=22 Hz), 4.15 (dq, 4H, J=7, 7 Hz), 5.52 (d, 1H, J=11 Hz), 6.26 (d, 1H, J=17 Hz), 6.85 (dd, 1H, J=17,11 Hz), 7.26–7.34 (m, 2H), 7.66 (t, 1H, J=8 Hz); MS (Cl) m/z256 (MH$^+$, 100%); Anal. calc'd for $C_{12}H_{18}NO_3P \cdot 0.50\ H_2O$: C, 54.54; H, 7.25; N, 5.30; P, 11.72. Found: C, 54.80; H, 7.21; N, 5.34; P, 11.87.

Step 3: Preparation of

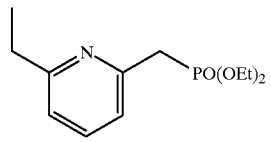

To a stirred solution of the product of Step 2 (3.58 g, 14.0 mmol) in CH$_3$OH (100 mL) was added 5% Pd/C (0.36 g). The mixture was stirred under H$_2$ (1 atm) at room temperature for 16 h. The mixture was diluted with EtOAc and extracted with 10% HCl. The solids were filtered and washed with CH$_3$OH. The filtrate and washings were combined and concentrated in vacuo to give the desired product (3.56 g, 99%) as a clear oil. $^1$H NMR (400 MHz, CDCl$_3$) δ 1.32 (t, 6H, J=7 Hz), 1.34 (t, 3H, J=7.6 Hz), 2.84 (q, 2H, J=7.6 Hz), 3.44 (d, 2H, J=22 Hz), 4.13 (dq, 4H, J=7, 7 Hz), 7.08 (d, 1H, J=7.6 Hz), 7.25 (d, 1H, J=7.6 Hz), 7.59 (t, 1H, J=7.6 Hz); MS (Cl) m/z 258 (MH$^+$, 100%); Anal. calc'd for $C_{12}H_{20}NO_3P \cdot 0.50\ H_2O$: C, 54.13; H, 7.95; N, 5.26; P, 11.63. Found: C, 54.19; H, 7.95; N, 5.25; P, 11.65.

Step 4: Using a procedure similar to that described in Example 1, Step 9, combine the product of Step 3 with the product of Example 1, Step 6, to obtain the title compound as a white gum. $^1$H NMR (400 MHz, CDCl$_3$) δ 0.78–2.01 (m, 12H), 1.36 (t, 3H, J=7.6 Hz), 1.49 (d, 3H, J=6 Hz), 2.36–2.43 (m, 2H), 2.70–2.78 (m, 1H), 2.86 (q, 2H, J=7.6 Hz), 4.77–4.85 (m, 1H), 6.47–6.58 (m, 2H), 7.06 (d, 1H, J=7.6 Hz), 7.11 (d, 1H, J=7.6 Hz), 7.59 (t, 1H, J=7.6 Hz). HCl salt: off-white solids; $[\alpha]^{22}_D$=+21.3° (c 0.41, CH$_3$OH); MS (ESI) m/z 340 (MH$^+$, 100%). Anal. calc'd for $C_{22}H_{29}NO_2 \cdot HCl \cdot 1.50\ H_2O$: C, 65.58; H, 8.25; N, 3.48. Found: C, 65.54; H, 8.40; N, 3.68.

EXAMPLES 9, 9A and 9B

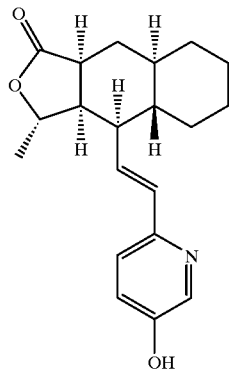

9

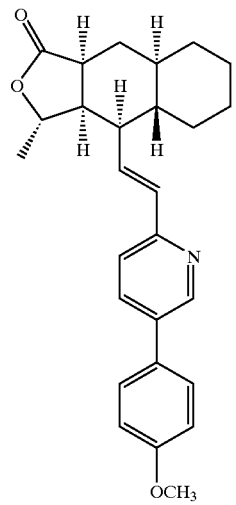

9A

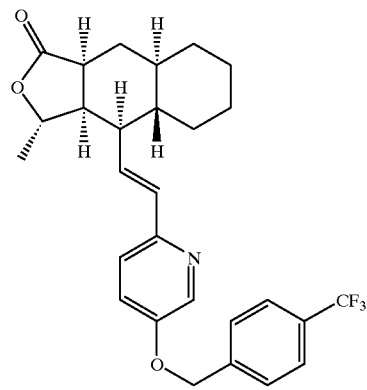

9B

EXAMPLE 9

Step 1: Using a procedure similar to that of Example 1, Step 7, treat 3-hydroxy-6-methylpyridine with triisopropylsilyl chloride.

Step 2: Using a procedure similar to that of Example 1, Step 8, treat the product of Step 1 with diethylchlorophosphate.

Step 3:

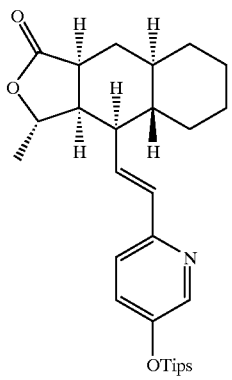

Using a procedure similar to that of Example 1, Step 9, combine the product of Step 3 with the product of Example 1, Step 6, to obtain the desired product (Tips is triisopropylsilyl) as white solids; MS (FAB) m/z 484 (MH$^+$, 100%).

Step 4: By treating the product of Step 3 as described in Example 1, Step 10, the product of Example 9 was obtained. HCl salt, off-white solids; MS (Cl) m/z342 (MH⁺, 100%).

EXAMPLE 9A,

Step 1:

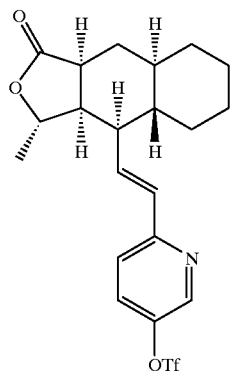

To a solution of the product of Example 9 (30 mg, 0.092 mmol) and Et₃N (64 mL, 0.46 mmol) in CH₂Cl₂ (5 mL) at room temperature was added triflic anhydride (46 mL, 0.28 mmol) and the mixture was stirred for 10 min, then washed with water. The organic layer was dried (MgSO₄) and concentrated in vacuo. Flash chromatography of the residue on a silica gel column with EtOAc:hexane (40:60) as eluent gave the desired triflate (42 mg, 100%). HCl salt, light-yellow solids. MS (FAB) m/z460 (MH⁺, 100%).

Step 2: To a solution of the product of Step 1 (37 mg, 0.081 mmol) and p-methoxyphenylboronic acid (24 mg, 0.16 mmol) in toluene (2 mL) was added EtOH (0.5 mL), K₂CO₃ (44 mg, 0.32 mmol) in H₂O (1 mL), and Pd(PPh₃)₄ (9 mg, 0.008 mmol). The mixture was heated in a closed pressure tube under Ar at 120° C. for 16 h. The mixture was diluted with EtOAc, washed with 5% NaOH and brine, dried (MgSO₄) and concentrated in vacuo. Preparative TLC separation of the residue with EtOAc:hexane (40:60) as eluent gave 9A (24 mg, 71%). HCl salt, white solids. MS (Cl) m/z418 (MH⁺, 100%).

EXAMPLE 9B:

A mixture of the product of Example 9 (33 mg, 0.10 mmol), 4-(trifluoromethyl)benzyl bromide (36 mg, 0.15 mmol), and K₂CO₃ (42 mg, 0.30 mmol) in acetone (2 mL) was stirred at reflux temperature for 3 h. The solids were filtered and washed with EtOAc. The filtrate and the washings were combined and concentrated in vacuo. Preparative TLC separation of the residue with EtOAc:hexane (40:60) as eluent gave Example 9B (41 mg, 85%). HCl salt, off-white solids. MS (Cl) m/z 486 (MH⁺, 100%).

EXAMPLE 10, 10A, 10B

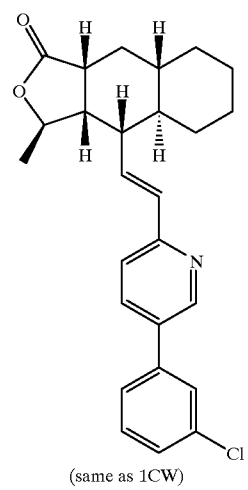

(same as 1CW)

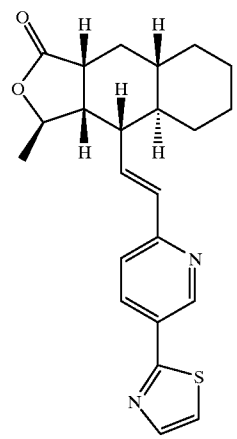

10A

-continued

10B

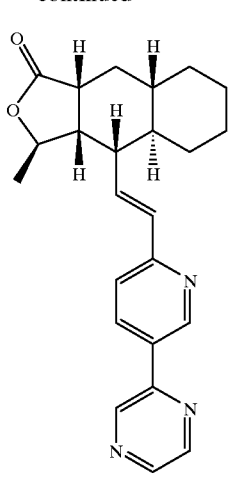

Alternatives to coupling procedure of Example 9:

Method A:

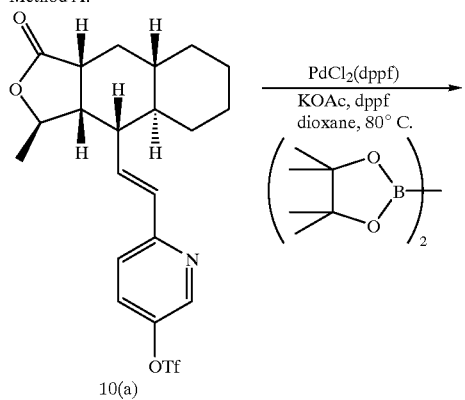

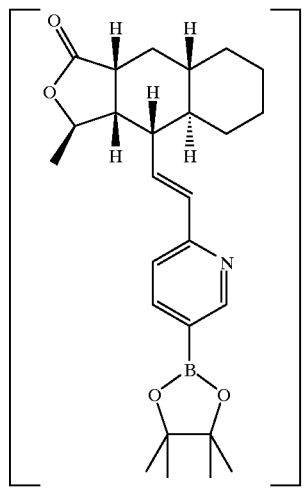

A mixture of 10(a) (prepared similarly to Example 9A, step 1, using appropriate starting material, 460 mg, 1.00 mmol), diboron pinacol ester (305 mg, 1.20 mmol), potassium acetate (294 mg, 3.00 mmol), 1,1′-bis (diphenylphosphino)ferrocene (55 mg, 0.10 mmol), and dichloro[1,1′-bis(diphenylphosphino)ferrocene]palladium (II) dichloromethane adduct (82 mg, 0.10 mmol) in 1,4-dioxane (5 mL) was heated in a closed pressure tube under $N_2$ at 80° C. for 2 h. The mixture was cooled to room temperature. To this mixture was added 1-bromo-3-chlorobenzene (235 μL, 2.00 mmol), $K_3PO_4$ (636 mg, 3.00 mmol), dichloro-[1,1′-bis(di-phenylphosphino)ferrocene]-palladium (II) dichloromethane adduct (41 mg, 0.050 mmol), and 1,4-dioxane (5 mL). The mixture was heated in a closed pressure tube under nitrogen at 80° C. for 16 h. The mixture was partitioned between $NH_4Cl$ (saturated) and EtOAc. The organic layer was washed with brine, dried ($MgSO_4$), and concentrated in vacuo. Flash chromatography of the residue on a silica gel column with EtOAc:hexane (20:80, then 25:75) as eluent gave (+)-Example 10 (360 mg, 85%) as off-white solids. HCl salt: off-white solids; MS (FAB) m/z 422 ($MH^+$, 100).

Method B:

10A: A mixture of 10(a) (46 mg, 0.10 mmol), 2-tributylstannylthiazole (112 mg, 0.30 mmol), and tetrakis(triphenylphosphine)palladium (12 mg, 0.010 mmol) in N-methylpyrrolidinone (1 mL) was heated in a closed pressure tube under nitrogen at 120° C. for 20 h. The mixture was partitioned between $H_2O$ and ether. The organic layer was washed with brine, dried ($MgSO_4$), and concentrated in vacuo. Preparative TLC of the residue on a silica gel plate with EtOAc:hexane (30:70) as eluent gave Example 10A (17 mg). MS: 395 ($MH^+$).

10B: Example 10B was prepared using a similar procedure: MS: 392 ($MH^+$).

EXAMPLE 11

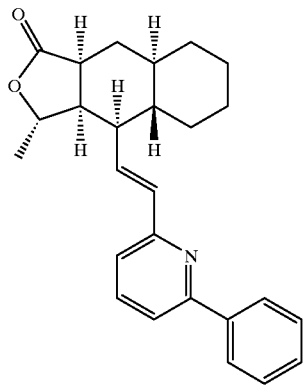

To a solution of Example 1L (20 mg, 0.058 mmol) and phenylboronic acid (14 mg, 0.12 mmol) in toluene (2 mL) was added EtOH (0.5 mL), $K_2CO_3$ (32 mg, 0.23 mmol) in $H_2O$ (1 mL), and $Pd(PPh_3)_4$ (7 mg, 0.006 mmol). The mixture was heated in a closed pressure tube under Ar at 120° C. for 16 h. The mixture was diluted with EtOAc, washed with 5% NaOH and brine, dried ($MgSO_4$), and concentrated in vacuo. Preparative TLC separation of the residue with EtOAc:hexane (20:80) as eluent gave the title compound (10 mg, 71%). HCl salt, off-white solids. MS (Cl) m/z 388 ($MH^+$, 100%).

EXAMPLE 12

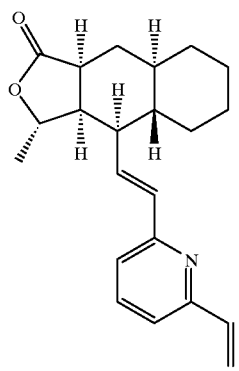

Example 1L (333 mg, 0.963 mmol) was heated with vinyltri-n-butyltin (424 μL, 1.44 mmol) and Pd(PPh$_3$)$_4$ (62 mg, 0.05 mmol) in THF (10 mL) in a closed pressure tube under Ar at 120° C. for 16 h. The mixture was diluted with EtOAc, washed with NH$_4$Cl (sat.) and brine, dried (MgSO$_4$) and concentrated in vacuo. Flash chromatography of the residue on a silica gel column with EtOAc:hexane (20:80) as eluent gave the title compound (281 mg, 86%) as white solids. MS (Cl) m/z 338 (MH$^+$, 100%).

EXAMPLE 13

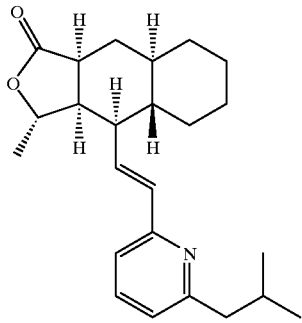

To a solution of ZnCl$_2$ (0.96 mL, 0.5 M in THF) was added isobutylmagnesium chloride (0.22 mL, 2.0 M in ether) at −78° C. The mixture was stirred at −78° C. to room temperature for 1 h. Example 1L (30 mg) and Pd(PPh$_3$)$_4$ (10 mg) were added to the resulting mixture. The mixture was heated in a closed pressure tube under Ar at 120° C. for 2.5 h. The mixture was diluted with EtOAc, washed with NH$_4$Cl (sat.), dried (MgSO$_4$) and concentrated in vacuo. Preparative TLC separation of the residue with EtOAc:hexane (20:80) as eluent gave the title compound (16 mg) as the HCl salt, white solids. MS (FAB) m/z 368 (MH$^+$, 100%).

EXAMPLE 14

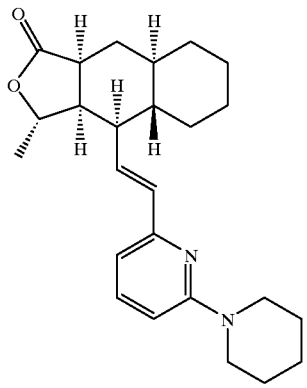

Example 1L (20 mg, 0.058 mmol) was heated with piperidine (0.5 mL) in a closed pressure tube under Ar at 190° C. for 13 h. The mixture was diluted with EtOAc, washed with NaHCO$_3$ (sat.) and brine, dried (MgSO$_4$), and concentrated in vacuo. Preparative TLC separation of the residue with EtOAc:hexane (30:70) as eluent gave the title compound (15 mg, 66%). HCl salt, white solids. MS (Cl) m/z 395 (MH$^+$, 100%).

EXAMPLE 15

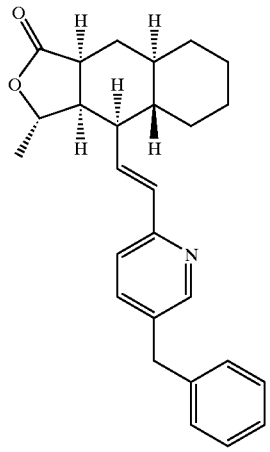

To a solution of ZnCl$_2$ (0.95 mL, 0.44 mmol, 0.5 M in THF) was added benzylmagnesium chloride (0.44 mL, 0.44 mmol, 1.0 M in ether) at −78° C. The mixture was stirred at −78° C. to room temperature for 1 h. The product of Example 9A, Step 1 (40 mg, 0.087 mmol) and Pd(PPh$_3$)$_4$ (10 mg, 0.009 mmol) were added to the resulting mixture. The mixture was heated in a closed pressure tube under Ar at 120° C. for 16 h. The mixture was diluted with EtOAc, washed with brine, dried (MgSO$_4$) and concentrated in vacuo. Preparative TLC separation of the residue with EtOAc:hexane (30:70) as eluent gave the title compound (34 mg, 97%). HCl salt, off-white solids. MS (FAB) m/z 402 (MH$^+$, 100%).

EXAMPLES 16, 16A, 16B and 16C

Step 1:

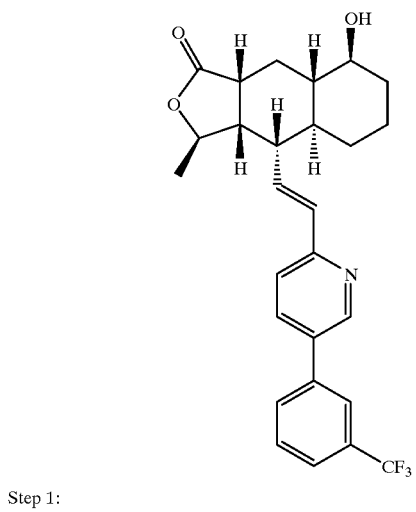

37A

37B

A mixture of 6 (3.15 g) and SeO$_2$ (3.10 g) in 1,4-dioxane (50 mL) and pyridine (5 mL) was heated in a closed pressure tube at 100° C. for 1 h. The mixture was cooled to room temperature, filtered, and concentrated in vacuo. Flash chromatography of the residue on a silica gel column with EtOAc:hexane (30:70) as eluent gave 37B (950 mg) and 37A (1.05 g).

Step 2:

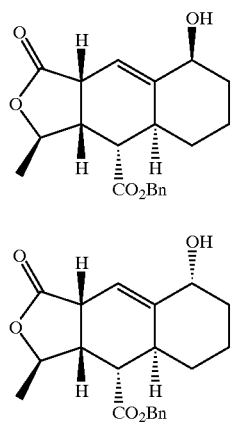

A mixture of 37A (1.05 g) and PtO$_2$ (250 mg) in EtOAc (70 mL) was stirred under a hydrogen balloon at room temperature for 16 h. The mixture was filtered and the filtrate was concentrated in vacuo to give the desired product (670 mg, 85%).

Step 3:

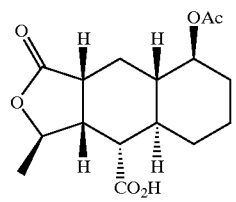

A mixture of the product of Step 2 (670 mg) and Ac$_2$O (2 mL) in pyridine (5 mL) was stirred at room temperature for 16 h. The mixture was poured into a mixture of dilute HCl solution and ice and stirred for 1 h. The resulting mixture was extracted with ether. The organic layer was washed with brine, dried, and concentrated in vacuo to give the desired product (700 mg).

Step 4:

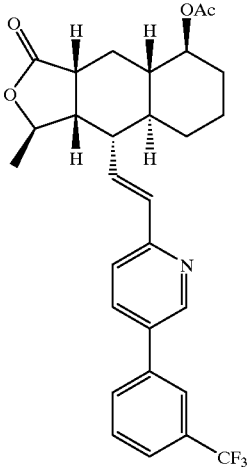

Treat the product of Step 3 in a manner similar to that described in Example 1, Steps 6 and 9, using the appropriate phosphonate to obtain the desired compound.

Step 5:

A mixture of the product of Step 4 (100 mg), NaOH (10%, 2 mL), and CH$_3$OH (2 mL) in THF (7 mL) was stirred at 0° C. for 3 h. The mixture was neutralized with saturated NH$_4$Cl solution and extracted with ether. The organic layer was washed with brine, dried, and concentrated in vacuo. Flash chromatography of the residue on a silica gel column with EtOAc:hexane (45:55, then 50:50) as eluent gave the title product (25 mg). MS (FAB) m/z 472 (MH$^+$, 100).

Using the appropriate phosphonates in the procedure of Example 16, Steps 4–5, the following compounds 16A and 16B were prepared:

16A

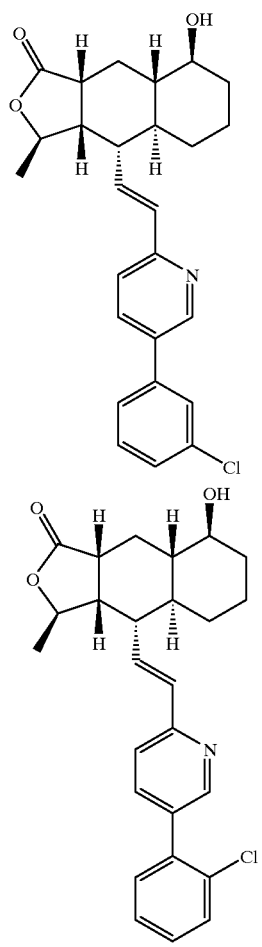

16A: (MS (ESI) m/z 438 (MH⁺, 100);
16B: MS (ESI) m/z 438 (MH⁺, 100).

Using the procedure of Example 16, Steps 2–5, employing starting material 37B, the following compound 16C was prepared:

16C

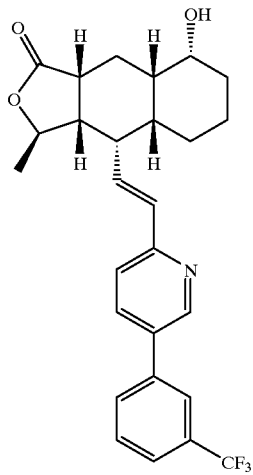

MS (FAB) m/z 472 (MH⁺, 100).

EXAMPLES 17 and 17A

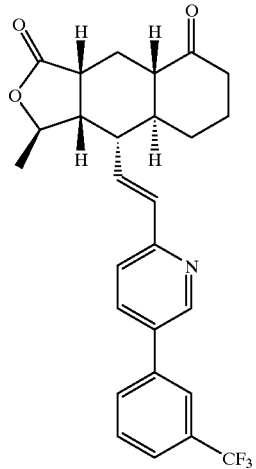

Jones reagent was added to a solution of the product of Example 16 hydrochloride (20 mg) in acetone (5 mL) at room temperature until red color persisted. The reaction was quenched with EtOH and extracted with ether. The organic layer was washed with brine, dried, and concentrated in vacuo to give the title compound (20 mg). "MS (FAB) m/z 470 (MH⁺, 100).

From the compound of Example 17, the following compound can be prepared by conventional methods known to those skilled in the art:

17A

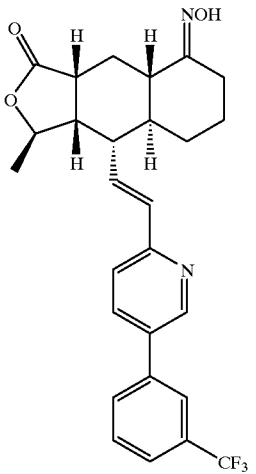

MS (ESI) m/z 485 (MH⁺, 100).

From 17A, the following compound can be prepared by conventional methods known to those skilled in the art:

17B

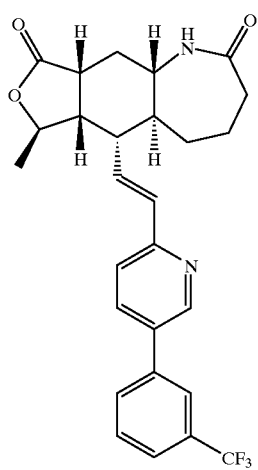

MS (FAB) m/z 485 (MH⁺, 100).

EXAMPLES 18, 18A, 18B, 18C, and 18D

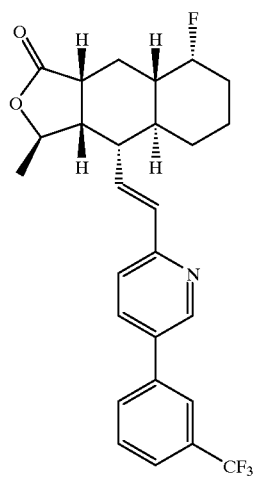

DAST (diethylaminosulfurtrifluoride) (2–3 drops) was added to a solution of the product of Example 16 (12 mg) in CH₂Cl₂ (2 mL) at 0° C. and the mixture was allowed to warm to room temperature. The mixture was washed with NaHCO₃ solution (sat'd) and brine, dried and concentrated in vacuo. Flash chromatography of the residue on a silica gel column with EtOAc:hexane (35:65) as eluent gave the title product (8 mg). MS (ESI) m/z 474 (MH⁺, 100).

Using the procedure of Example 18, employing as starting material the product of Example 16C, the compound 18A was prepared; similarly, using the approrpiate starting materials, compounds 18B, 18C and 18D were also prepared:

18A

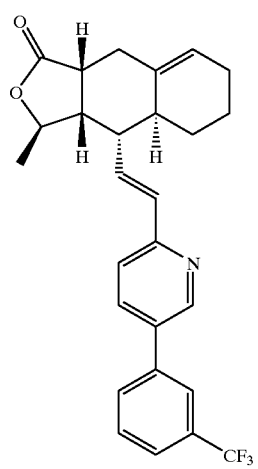

18B

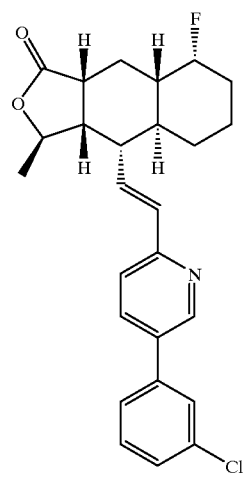

18C

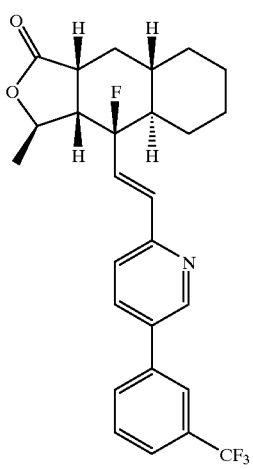

-continued

18D

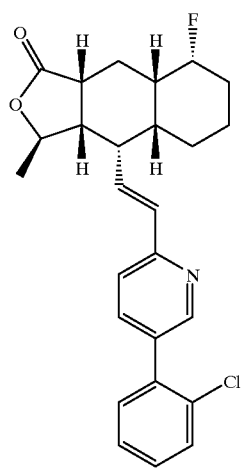

18A: MS (FAB) m/z 454 (MH+, 100).

18B: MS (ESI) m/z 440 (MH+, 100).

18C: MS (ESI) m/z 474 (MH+, 100).

18D: MS (ESI) m/z 440 (MH+, 100).

EXAMPLE 19

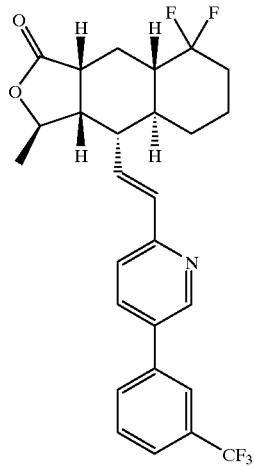

DAST (250 mL) was added to a solution of the product of Example 17 (60 mg) in CH$_2$Cl$_2$ (5 mL) and stirred at room temperature for 3 days. The mixture was washed with saturated NaHCO$_3$ solution and brine, dried, and concentrated in vacuo. Flash chromatography of the residue on a silica gel column with EtOAc:hexane (35:65) as eluent gave the title product. MS (FAB) m/z 492 (MH+, 100).

EXAMPLES 20, 20A and 20B

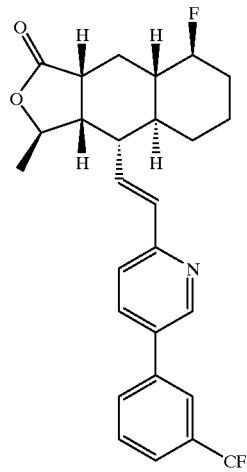

Step 1:

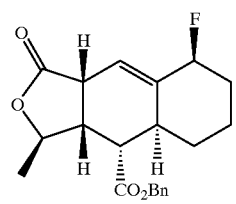

DAST was added to a solution of compound 37B (180 mg) in CH$_2$Cl$_2$ at −78° C. and stirred for 15 min. The mixture was washed with saturated NaHCO$_3$ solution and brine, dried, and concentrated in vacuo. Flash chromatography of the residue on a silica gel column with EtOAc: hexane (10:90) as eluent gave the desired product (100 mg).

Step 2:

Treat the product of Step 1 in a manner similar to that described in Example 16, Steps 2 and 4, gave the title compound. MS (ESI) m/z 474 (MH+, 100).

Using the appropriate phosphonate in the above procedure, 20A is prepared; using the procedure of 4C, the compound 20B is prepared from the product of Example 18:

20A

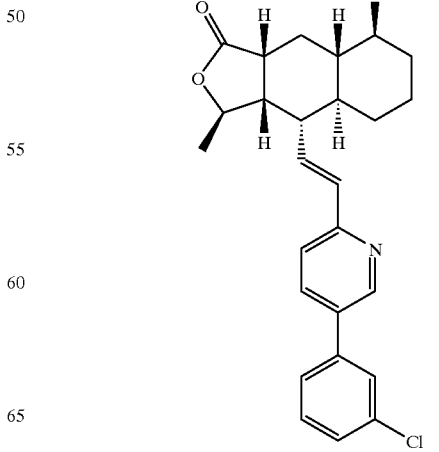

EXAMPLE 22, 22A

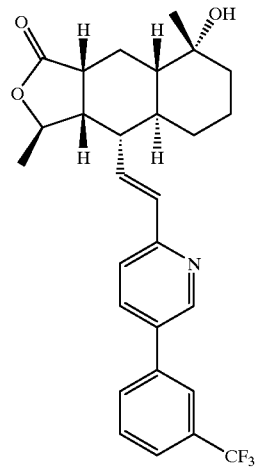

20A: MS (Cl) m/z 440 (MH⁺, 100).

20B: MS (ESI) m/z 490 (MH⁺, 100).

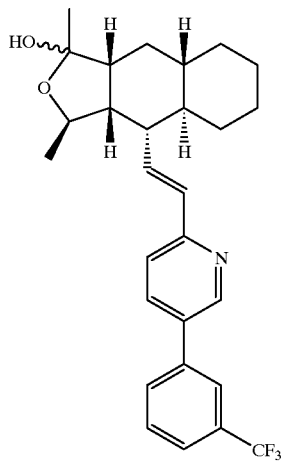

EXAMPLE 21

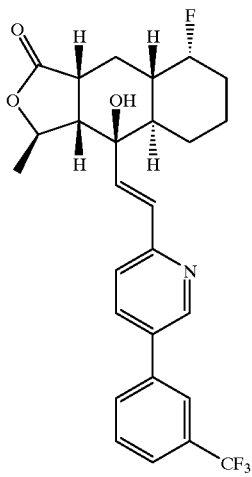

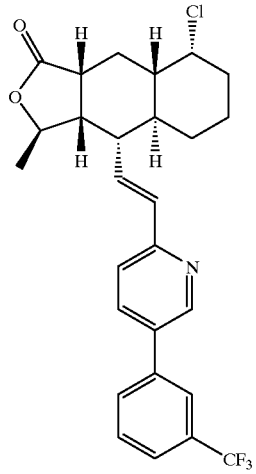

The product of Example 16 (30 mg, 0.063 mmol) was refluxed in SOCl₂ (1 mL) for 3 h. The mixture was concentrated in vacuo. Preparative TLC of the residue on a silica gel plate with EtOAc:hexane (30:70) as eluent gave the title product (13 mg). MS (FAB) m/z 490 (MH⁺, 100).

22: MeMgBr (0.1 mL, 1.4 M) was added to a solution of the product of Example 17 (50 mg) in dry THF (3 mL) and stirred at room temperature for a few minutes. The mixture was neutralized with saturated NH₄Cl solution and extracted with ether. The organic layer was washed with brine, dried, and concentrated in vacuo. Flash chromatography of the residue on a silica gel column with EtOAc:hexane (40:60) as eluent gave the title product (10 mg). MS (FAB) m/z 486 (MH⁺, 100).

22A: Using the product of Example 4 in a similar procedure, 22A was prepared. MS (FAB) m/z 454 (MH⁺, 100).

EXAMPLES 23, 23A, 23B

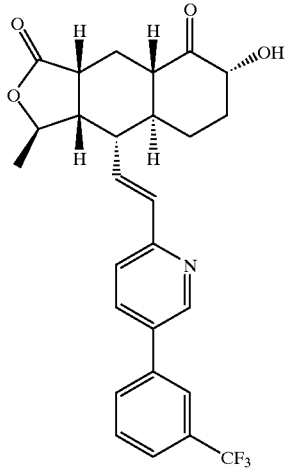

23

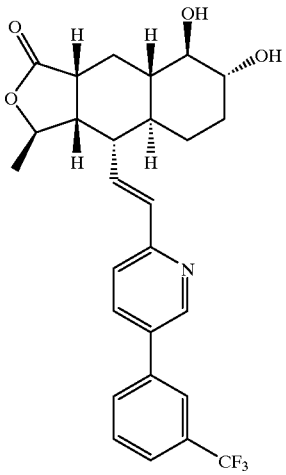

23B

23A: MS (FAB) m/z 488 (MH+, 100).
23B: MS (FAB) m/z 488 (MH+, 100).

EXAMPLE 24 n-BuLi (0.15 mL, 0.22 mmol) was added to a solution of diisopropylamine (0.060 mL, 0.22 mmol) in dry THF at −78° C. and stirred for a few minutes. A solution of the product of Example 17 (40 mg, 0.10 mmol) in dry THF (2 mL) was added at −78° C. and stirred for 15 min. A solution of (10-camphorsulfonyl)oxaziridine (46 mg, 0.20 mmol) in dry THF (2 mL) was added at −78° C. and stirred to room temperature (2 h). The mixture was neutralized with saturated NH$_4$Cl solution and extracted with ether. The organic layer was washed with brine, dried, and concentrated in vacuo. Flash chromatography of the residue on a silica gel column with EtOAc:hexane (60:40, then 70:30) as eluent gave the title product (10 mg). MS (ESI) m/z 486 (MH+, 100).

The product of Example 23 is treated in a manner similar to that described for Example 5B to give the following compounds:

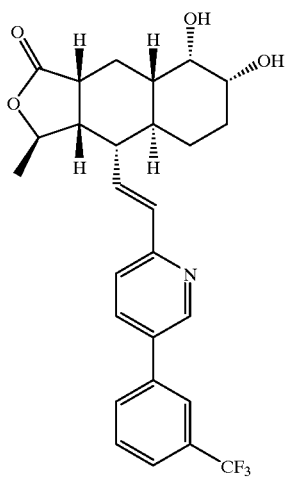

23A

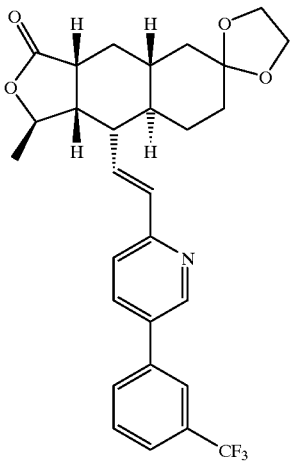

Step 1:

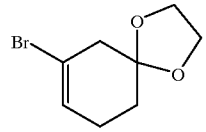

See *J. Organomettallic Chem.*, 521 (1996) pp203–210; *J. Org. Chem.*, 47 (1982), pp2825–2832.

Step 2:

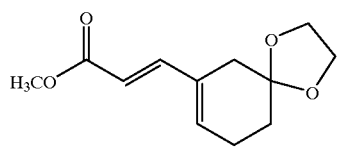

The product of Step 1(27.5 g, 0.1255 mol) was dissolved in DMF (400 mL) and methylacrylate (23 ml, 0.251 mol), Et$_3$N (52.25 mL, 0.3765 mol) and Pd(Ph$_3$P)$_2$Cl$_2$ (4.37 g, 5 mol %) were added successively. The mixture was heated at 750° C. for 16 h. The reaction mixture was combined with NH₄Cl (sat'd), extracted with ether and dried (MgSO₄). The extracts were concentrated in vacuo and the residue chromatographed (9:1–4:1 hexane/EtOAc) to give 20 g (71%) of the desired compound. ¹H NMR (CDCl₃) δ 1.78 (t, J=6.5 Hz, 2H), 2.38 (s, 2H), 2.44 (m, 2H), 3.74 (s, 3H), 4.0 (s, 4H), 5.73 (d, J=15 Hz, 1H), 6.17 (br s, 1H), 7.36 (d, J=15 Hz, 1H).

Step 3:

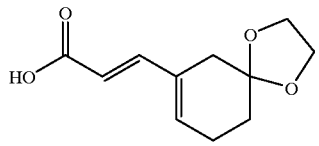

The product of Step 2 (20 g, 0.089 mol) was dissolved in a 1:1 mixture of THF/CH₃OH (520 mL total). 1 M NaOH solution (260 mL) was added slowly. The mixture was stirred for 4 h and water was added. The mixture was washed with ether, the aqueous layer was acidified to pH 1 and extracted with EtOAc (×3), the combined extracts were dried (MgSO₄) and the solution concentrated in vacuo to give 19 g (99%) of the desired compound. ¹H NMR (CDCl₃) δ 1.79 (t, J=6.5 Hz, 2H), 2.40 (s, 2H), 2.46 (m, 2H), 4.01 (m, 4H), 5.73 (d, J=15.7 Hz, 1H), 6.23 (s, 1H), 7.41 (d, J=15.7 Hz, 1H).

Step 4:

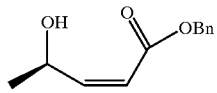

The product of Example 1, Step 2 (23.28 g, 0.114 mol) was dissolved in THF (232 mL) and Lindlar's hydrogenation catalyst was added (3.48 g). The mixture was placed under 1 atm pressure of H₂ (g) and stirred for 2.5 h. The mixture was filtered and concentrated in vacuo to give the desired compound (22 g, 93%). ¹H NMR (CDCl₃) δ 1.32 (d, J=6.5 Hz, 3H), 5.09 (m, 1H), 5.17 (s, 2H), 5.86 (d, J=11.7 Hz, 1H), 6.30 (dd, J=11.7, 7.0 Hz, 1H), 7.38 (s, 5H).

Step 5:

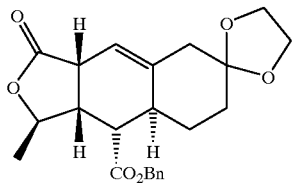

The product of step 3 (18 g, 0.0856 mol) was dissolved in CH₂Cl₂ (350 mL) and cooled to 0° C. 1,3-Dicyclohexylcarbodiimide (23.23 g, 0.112 mol) was added, followed by 4-pyrollidinopyridine (1.39 g, 9.4 mmol). After stirring 5 min, a solution of the product of step 4 (22 g, 0.1067 mol) in CH₂Cl₂ (127 mL) was added over 10 min. The mixture was stirred at 0° C. for 2 h and at room temperature for 1 h. The mixture was then filtered, concentrated in vacuo, and the residue column chromato-graphed (9:1–4:1 hexane/EtOAc as eluent) to obtain 27 g of an oil. This product was dissolved in xylene (300 mL) and heated at 215° C. for 7 h. Column chromatography (9:1–4:1–2:1 hexane/EtOAc) gave 13.2 g of an oil. The oil was dissolved in THF (264 mL) and DBU (4.9 mL, 0.033 mol) was added.

The mixture was stirred for 1 h, diluted with EtOAc (500 mL), washed with NH₄Cl(sat), dried (MgSO₄), concentrated in vacuo, filtered through a pad (1 inch) of SiO₂ (eluting with EtOAc) and concentrated in vacuo to give the desired compound (13 g, 38%). ¹H NMR (CDCl₃) δ 1.10 (d, J=6.0 Hz, 3H), 1.2 (m, 1H), 1.65–1.85 (m, 2H), 1.92 (m,1H), 2.35 (m, 1H), 2.47 (m, 1H), 2.59 (dd, J=10.75, 4.0 Hz,1H), 2.70 (m,1H), (q, J=2.5 Hz,1H), 3.85–4.0 (m, 5H), 4.45 (m, 1H), 5.15 (AB quartet, J=12.0,10.5 Hz, 2H), 5.36 (br s, 1H), 7.35 (s, 5H).

Step 6:

The product of step 5 (4.92 g, 0.0123 mol) was dissolved in EtOAc (250 mL), 10% palladium on carbon (492 mg) was added and the mixture stirred under 1 atm of H₂ (g) for 1 h. The mixture was filtered through a pad of celite, PtO₂ (492 mg) was added to the filtrate and the mixture stirred for 16 h under 1 atm H₂ (g). The mixture was then filtered and concentrated in vacuo to give 3.81 g (99%) of the desired compound. ¹H NMR (CDCl₃) δ 1.25 (m, 2H), 1.35 (d, J=6.5 Hz, 3H), 1.3–1.5 (m, 3H), 1.6 (m, 1H), 1.7–1.95 (m, 3H), 2.5 (m,1H), 2.58 (m, 1H), 2.68 (m, 1H), 3.95 (m, 5H), 4.69 (m, 1H).

Step 7:

The product of step 6 (1 g, 3.2 mmol) was dissolved in toluene (20 mL), SOCl₂ (1.25 mL) was added and the mixture heated at 80° C. for 16. The mixture was concentrated in vacuo, dissolved in fresh toluene (16 mL) and cooled to 0° C. Pd(Ph₃P)₄ (186 mg) was added, followed by tributyltinhydride (1.3 mL, 4.8 mmol). The mixture was stirred for 3 h, then chromatographed (4:1–2.5:1 hexane:EtOAc) to give 450 mg (48%) of the desired compound. ¹H NMR (CDCl₃) δ 1.24 (d, J=δ 6.5 Hz, 3H), 1.0–1.9 (m, 10H), 2.48 (m, 1H), 2.6–2.7 (m, 2H), 3.87 (m, 4H), 4.54 (m, 1H), 9.70 (br s, 1H).

Step 8:

The product of Example 4, Step 3 (1.14 g, 3.0 mmol) was dissolved in THF (10 mL) and cooled to 0° C. n-BuLi (1.9 mL of 2.5 M solution in hexanes, 2.9 mmol) was added and the mixture stirred for 10 min. The solution was then added to a solution of the product of Step 7 (450 mg, 1.53 mmol) in THF (10 mL) at 0° C. The mixture was stirred for 2 h, then NH₄Cl (sat) was added. The mixture was extracted (EtOAc), dried (MgSO₄), concentrated in vacuo and then chromatographed (60:40 hexane:EtOAc) to give 650 mg (83%) of the title compound.

¹H NMR (CDCl₃) δ 1.12–1.55 (m, 6H), 1.43 (d, J=6 Hz, 3H), 1.78 (m, 2H), 1.79 (m, 1H), 1.96 (dd, J=6.5, 3.0 Hz, 1H), 2.9 (m, 2H), 2.70 (quintet, J=6. 5Hz, 1H), 3.95 (m, 4H), 4.76 (m, 1H), 6.55 (d, J=15 5 Hz, 1H), 6.65 (m, 1H), 7.29 (d, J=8.0 Hz, 1H), 7.60 (t, J=7.5 Hz, 1H), 7.66 (d, J=7.5 Hz, 1H), 7.75 (d, J=7.5 Hz, 1H), 7.80 (s, 1H), 7.86 (d, J=8.0 Hz, 1H), 8.79 (s, 1H).

The product of Example 24 is treated as described below to obtain Examples 24A, 24B-1, 24B-2 and 24C:

24A

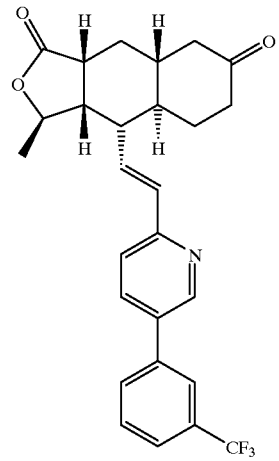

24B-1

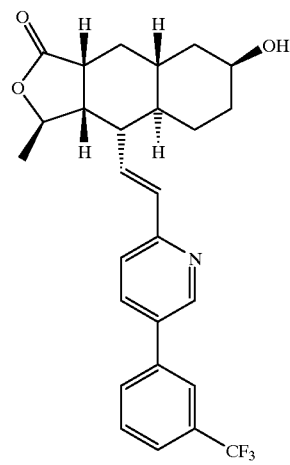

24B-2

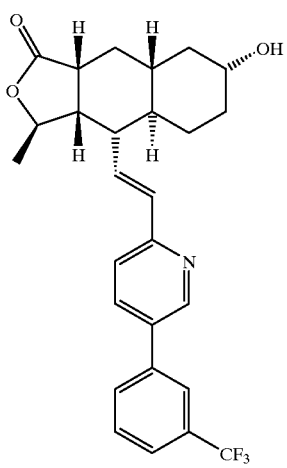

24C

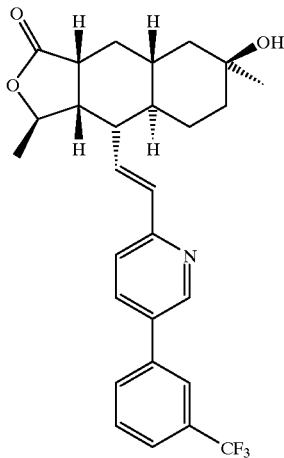

24A: The product of Example 24 (650 mg, 1.26 mmol) was dissolved in acetone (7.5 mL) and HCl (7.5 mL of a 1 M solution) was added. The mixture was heated at 50° C. for 16 h. NaHCO$_3$ (sat'd) was added and the mixture extracted with EtOAc. The combined extracts were dried (MgSO$_4$), concentrated in vacuo and chromatographed (1:1 hexane: EtOAc) to give 590 mg (99%) of compound 24A. $^1$H NMR (CDCl$_3$) δ 1.2–1.5 (m, 2H), 1.47 (d, J=7.0 Hz, 3H), 1.65 (m, 2H), 2.08 (m, 2H), 2.10 (m, 2H), 2.3–2.5 (m, 4 H), 2.74 (quintet, J=6.5 Hz, 1H), 4.80 (m, 1H), 6.59 (d, J=6.5Hz, 1H), 6.72 (m, 1H), 7.28 (d, J=8.0 Hz, 1H), 7.61 (t, J=7.5 Hz, 1H), 7.66 (d, J=7.5 Hz, 1H), 7.76 (d, J=7.5 Hz, 1H), 7.81 (s, 1H), 7.87 (d, J=8.0 Hz, 1H), 8.80 (s, 1H).

24B-1 and 24B-2: The product of Example 24A (100 mg, 0.213 mmol) was dissolved in EtOH (8 mL) and NaBH$_4$ (30 mg) was added. After 5 min, NaHCO$_3$ (sat) was added and the mixture extracted with EtOAc. The extracts were dried (MgSO$_4$) and concentrated in vacuo. Purification by preparative TLC (47.5:47.5:5 hexane:EtOAc:CH$_3$OH) gave the least polar isomer, 24B-1 (15 mg, 15%): $^1$H NMR (CDCl$_3$) δ 1.15–1.4 (m, 4H), 1.43 (d, J=6.0 Hz, 3H), 1.5–1.7 (m, 3H), 1.75–1.95 (m, 3H), 2.35–2.5 (m, 2H), 2.72 (quintet, J=6.6 Hz, 1H), 4.16 (br s, 1H), 4.75 (m, 1H), 5.46, J=15.5 Hz, 1H), 6.65 (m, 1H), 7.29 (d, J=8.0 Hz, 1H), 7.60 (t, J=8 Hz, 1H), 7.66 (d, J=7.5 Hz, 1H), 7.76 (d, J=7.5 Hz, 1H), 7.80 (s, 1H), 7.85 (d, J=8.0 Hz, 1H), 8.79 (s, 1H); and the most polar isomer, 24B-2 (70 mg, 70%): $^1$H NMR (CDCl$_3$) δ 0.93 (m, 1H), 1.06–1.4 (m, 5H), 1.43 (d, J=6.0 Hz, 3H), 1.85–2.05 (m, 4H), 2.40 (m, 2H), 2.70 (quintet, J=6.5 Hz, 1H), 3.64 (m, 1H), 4.75 (m, 1H), 6.55 (d, J=15.5 Hz, 1H), 6.64 (m, 1H), 7.29 (d, J=8.0 Hz, 1H), 7.60 (t, J=7.75 Hz, 1H), 7.65 (d, J=7.5 Hz, 1H), 7.75 (d, J=7.5 Hz, 1H), 7.80 (s, 1H), 7.85 (d, J=8.0 Hz, 1H), 8.79 (s, 1H).

24C: The product of Example 24A (30 mg, 0.0638 mmol) was dissolved in THF (1 mL). CH$_3$MgBr (150 μL of a 1M solution) was added. TLC showed a more polar compound. NH$_4$Cl (sat'd) was added and the mixture extracted with EtOAc. The extracts were dried (MgSO$_4$) and concentrated in vacuo. The residue was purified by preparative TLC (30:70 hexane:EtOAc) to give 6 mg of the desired compound. MS (FAB) m/z 486 (100).

Using similar procedures, compounds of the following structural formulas were prepared, wherein the variables are as defined in the table:

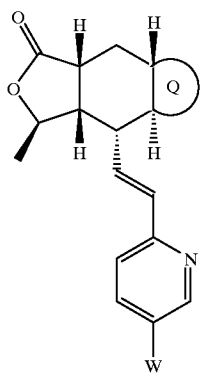
| Ex. | Q | W | Physical Data |
|---|---|---|---|
| 24D | cyclohexyl-OH (3,4-disub, OH down wedge) | 4-CH₃-phenyl | MS (FAB) m/z = 418 |
| 24E | cyclohexyl-OH (3,4-disub, OH dashed) | 4-CH₃-phenyl | MS (FAB) m/z = 418 |
| 24F | cyclohexyl-OH (3,4-disub, OH down wedge) | 2-CH₃-phenyl | MS (FAB) m/z = 418 |
| 24G | cyclohexyl-OH (3,4-disub, OH dashed) | 2-CH₃-phenyl | MS (FAB) m/z = 418 |
| 24H | cyclohexyl-OH (3,4-disub, OH down wedge) | 3-F-phenyl | MS (FAB) m/z = 422 |
| 24I | cyclohexyl-OH (3,4-disub, OH dashed) | 3-F-phenyl | MS (FAB) m/z = 422 |

-continued

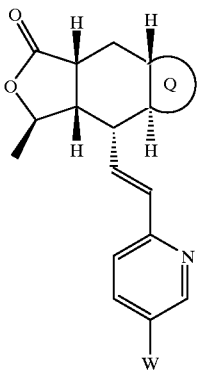

| Ex. | Q | W | Physical Data |
|---|---|---|---|
| 24J | cyclohexane with OH (one stereochem) | 4-fluorophenyl | MS (FAB) m/z = 422 |
| 24K | cyclohexane with OH (other stereochem) | 4-fluorophenyl | MS (FAB) m/z = 422 |
| 24L | cyclohexane with OH | 3-chlorophenyl | $^1$H NMR(CDCl$_3$)0.93(m, 1H), 1.05–1.38(m, 5H), 1.43(d, J=6.0Hz, 3H), 1.88–2.1(m, 4H), 2.36(m, 2H), 2.68(m, 1H), 3.65(m, 1H), 5.75(m, 1H), 6.5–6.65(m, 2H), 7.27(d, J=8.0Hz, 1H), 7.35–7.5(m, 3H), 7.55(s, 1H), 7.81(d, J=8.0Hz), 8.75(s, 1H). |

The following formulations exemplify some of the dosage forms of this invention. In each, the term "active compound" designates a compound of formula I.

EXAMPLE A

Tablets

| No. | Ingredient | mg/tablet | mg/tablet |
|---|---|---|---|
| 1 | Active Compound | 100 | 500 |
| 2 | Lactose USP | 122 | 113 |
| 3 | Corn Starch, Food Grade, as a 10% paste in Purified Water | 30 | 40 |
| 4 | Corn Starch, Food Grade | 45 | 40 |
| 5 | Magnesium Stearate | 3 | 7 |
| | Total | 300 | 700 |

Method of Manufacture

Mix Item Nos. 1 and 2 in suitable mixer for 10–15 minutes. Granulate the mixture with Item No.3. Mill the damp granules through a coarse screen (e.g., ¼", 0.63 cm) if necessary. Dry the damp granules. Screen the dried granules if necessary and mix with Item No. 4 and mix for 0–15 minutes. Add Item No. 5 and mix for 1–3 minutes. Compress the mixture to appropriate size and weight on a suitable tablet machine.

EXAMPLE B

Capsules

| No. | Ingredient | mg/tablet | mg/tablet |
|---|---|---|---|
| 1 | Active Compound | 100 | 500 |
| 2 | Lactose USP | 106 | 123 |
| 3 | Corn Starch, Food Grade | 40 | 70 |
| 4 | Magnesium Stearate NF | 4 | 7 |
| | Total | 250 | 700 |

Method of Manufacture

Mix Item Nos. 1, 2 and 3 in a suitable blender for 10–15 minutes. Add Item No.4 and mix for 1–3 minutes. Fill the mixture into suitable two-piece hard gelatin capsules on a suitable encapsulating machine.

The activity of the compounds of formula I can be determined by the following procedures.

In Vitro Testing Procedure for Thrombin Receptor Antagonists:

Preparation of [$^2$H]haTRAP

A(pF-F)R(ChA)(hR)(I$_2$-Y)—NH$_2$ (1.03 mg) and 10% Pd/C (5.07 mg) were suspended in DMF (250 $\mu$l) and diisopropylethylamine (10 $\mu$l). The vessel was attached to the tritium line, frozen in liquid nitrogen and evacuated. Tritium gas (342 mCi) was then added to the flask, which was stirred at room temperature for 2 hours. At the completion of the reaction, the excess tritium was removed and the reacted peptide solution was diluted with DMF (0.5 ml) and filtered to remove the catalyst. The collected DMF solution of the crude peptide was diluted with water and freeze dried to remove the labile tritium. The solid peptide was redissolved in water and the freeze drying process repeated. The tritiated peptide ([$^3$H]haTRAP) was dissolved in 0.5 ml of 0.1% aqueous TFA and purified by HPLC using the following conditions: column, Vydac C18, 25 cm×9.4 mm I.D.; mobile phase, (A) 0.1% TFA in water, (B) 0.1% TFA in CH$_3$CN; gradient, (A/B) from 100/0 to 40/60 over 30 min; flow rate, 5 ml/min; detection, UV at 215 nm. The radiochemical purity of [$^3$H]haTRAP was 99% as analyzed by HPLC. A batch of 14.9 mCi at a specific activity of 18.4 Ci/mmol was obtained.

Preparation of platelet membranes

Platelet membranes were prepared using a modification of the method of Natarajan et al (Natarajan et al, *Int. J. Peptide Protein Res.* 45:145–151 (1995)) from 20 units of platelet concentrates obtained from the North Jersey Blood Center (East Orange, N.J.) within 48 hours of collection. All steps were carried out at 4° C. under approved biohazard safety conditions. Platelets were centrifuged at 100×g for 20 minutes at 4° C. to remove red cells. The supernatants were decanted and centrifuged at 3000×g for 15 minutes to pellet platelets. Platelets were resuspended in 10 mM Tris-HCl, pH 7.5,150 mM NaCl, 5 mM EDTA, to a total volume of 200 ml and centrifuged at 4400×g for 10 minutes. This step was repeated two additional times. Platelets were resuspended in 5 mM Tris-HCl, pH 7.5, 5 mM EDTA to a final volume of approximately 30 ml and were homogenized with 20 strokes in a Dounce homogenizer. Membranes were pelleted at 41,000×g, resuspended in 40–50 ml 20 mM Tris-HCl, pH 7.5,1 mM EDTA, 0.1 mM dithiothreitol, and 10 ml aliquots were frozen in liquid N$_2$ and stored at −80° C. To complete membrane preparation, aliquots were thawed, pooled, and homogenized with 5 strokes of a Dounce homogenizer. Membranes were pelleted and washed 3 times in 10 mM triethanolamine-HCl, pH 7.4, 5 mM EDTA, and resuspended in 20–25 ml 50 mM Tris-HCl, pH 7.5, 10 mM MgCl$_2$, 1 mM EGTA, and 1% DMSO. Aliquots of membranes were frozen in liquid N$_2$ and stored at −80° C. Membranes were stable for at least 3 months. 20 units of platelet concentrates typically yielded 250 mg of membrane protein. Protein concentration was determined by a Lowry assay (Lowry et al, *J. Biol. Chem.*, 193:265–275 (1951)).

High Throughput Thrombin Receptor Radioligand Binding Assay

Thrombin receptor antagonists were screened using a modification of the thrombin receptor radioligand binding assay of Ahn et al. (Ahn et al, *Mol. Pharmacol.*, 51:350–356 (1997)). The assay was performed in 96 well Nunc plates (Cat. No. 269620) at a final assay volume of 200 $\mu$l. Platelet membranes and [$^3$H]haTRAP were diluted to 0.4 mg/ml and 22.2 nM, respectively, in binding buffer (50 mM Tris-HCl, pH 7.5, 10 mM MgCl$_2$, 1 mM EGTA, 0.1% BSA). Stock solutions (10 mM in 100% DMSO) of test compounds were further diluted in 100% DMSO. Unless otherwise indicated, 10 $\mu$l of diluted compound solutions and 90 $\mu$l of radioligand (a final concentration of 10 nM in 5% DMSO) were added to each well, and the reaction was started by the addition of 100 $\mu$l of membranes (40 $\mu$g protein/well). The binding was not significantly inhibited by 5% DMSO. Compounds were tested at three concentrations (0.1, 1 and 10 $\mu$M). The plates were covered and vortex-mixed gently on a Lab-Line Titer Plate Shaker for 1 hour at room temperature. Packard UniFilter GF/C filter plates were soaked for at least 1 hour in 0.1% polyethyleneimine. The incubated membranes were harvested using a Packard FilterMate Universal Harvester and were rapidly washed four times with 300 $\mu$l ice cold 50 mM Tris-HCl, pH 7.5, 10 mM MgCl$_2$, 1 mM EGTA. MicroScint 20 scintillation cocktail (25 $\mu$l) was added to each well, and the plates were counted in a Packard Top-Count Microplate Scintillation Counter. The specific binding was defined as the total binding minus the nonspecific binding observed in the presence of excess (50 $\mu$M) unlabeled haTRAP. The % inhibition by a compound of [$^3$H] haTRAP binding to thrombin receptors was calculated from the following relationship:

% Inhibition=Total binding-Binding in the presence of a test compound×100 Total binding-Nonspecific binding Materials A(pF-F)R(ChA)(hR)Y—NH$_2$ and A(pF-F)R(ChA)(hR)(I$_2$-Y)—NH$_2$, were custom synthesized by AnaSpec Inc. (San Jose, Calif.). The purity of these peptides was >95%. Tritium gas (97%) was purchased from EG&G Mound, Miamisburg Ohio. The gas was subsequently loaded and stored on an IN/US Systems Inc. Trisorber. MicroScint 20 scintillation cocktail was obtained from Packard Instrument Co.

Protocol For Ex-Vivo Platelet Aggregation In Cynomolgus Whole Blood Drug administration and blood collection:

Conscious chaired cynomolgus monkeys are allowed to equilibrate for 30 min. A needle catheter is inserted into a brachial vein for infusion of test drugs. Another needle catheter is inserted into the other brachial or saphenous vein and used for blood sampling. In those experiments where the compound is administered orally only one catheter is used. A baseline blood sample (1–2 ml) is collected in vacutainer tubes containing a thrombin inhibitor CVS 2139 (100 $\mu$g/0.1 ml saline) as an anticoaculant. The drug is then infused intravenously over a period of 30 min. Blood samples (1 ml) are collected at 5, 10, 20, 30 min during and 30, 60, 90 min after termination of the drug infusion. In PO experiments the animals are dosed with the drug using a gavage cannula. Blood samples are collected at 0, 30, 60, 90, 120, 180, 240, 300, 360 min after dosing. 0.5 ml of the blood is used for whole blood aggregation and the other 0.5 ml is used for determining the plasma concentration of the drug or its metabolites. Aggregation is performed immediately after collection of the blood sample as described below.

Whole Blood Aggregation:

A 0.5 ml blood sample is added to 0.5 ml of saline and warmed to 37° C. in a Chronolog whole blood aggregometer. Simultaneously, the impedance electrode is warmed in saline to 37° C. The blood sample with a stir bar is place in the heating block well, the impedance electrode is placed in the blood sample and the collection software is started. The software is allowed to run until the baseline is stabilized and then a 20 Ω calibration check is performed. 20 Ω is equal to 4 blocks on the graphic produced by the computer software. The agonist (haTRAP) is added by an adjustable volume pipette (5–25 μl) and the aggregation curve is recorded for 10 minutes. Maximum aggregation in 6 minutes following agonist is the value recorded.

In vitro Platelet Aggregation Procedure:

Platelet aggregation studies were performed according to the method of Bednar et al. (Bednar, B., Condra, C., Gould, R. J., and Connolly, T. M., *Throm. Res.*, 77:453–463 (1995)). Blood was obtained from healthy human subjects who were aspirin free for at least 7 days by venipuncture using ACD as anticoagulant. Platelet rich plasma was prepared by centrifugation at 100×g for 15 minutes at 15 deg C. Platelets were pelleted at 3000×g and washed twice in buffered saline containing 1 mM EGTA and 20 μg/ml apyrase to inhibit aggregation. Aggregation was performed at room temperature in buffered saline supplemented with 0.2 mg/ml human fibrinogen. Test compound and platelets were preincubated in 96-well flat-bottom plates for 60 minutes. Aggregation was initiated by adding 0.3 μM haTRAP or 0.1 U/ml thrombin and rapidly vortexing the mixture using a Lab Line Titer Plate Shaker (speed 7). Percent aggregation was monitored as increasing light transmittance at 405 nm in a Spectromax Plate Reader.

In vivo Antitumor Procedure:

Tests in the human breast carcinoma model in nude mouse are conducted according to the procedure reported in S. Even-Ram et. al., *Nature Medicine*, 4, 8 (1988), p. 909–914.

Using the test procedures described above, compounds of the invention were found to have $IC_{50}$ values (i.e., the concentration at which a 50% inhibition of thrombin receptor was observed) in the range of about 4 to 2000 nM, with preferred compounds having $IC_{50}$ values in the range of about 4 to 100 nM. The following data were obtained for preferred or representative compounds of formula I.

| In vitro Thrombin Receptor Antagonist Assay | |
|---|---|
| Example | $IC_{50}$ (nM) |
| 1A | 1600 |
| 1G | 147 |
| 1BN | 6 |
| 1DK | 14 |
| 1ES | 4 |
| 1FD | 21% at 1 μM |
| 2E | 350 |
| 3K | 10 |
| 4 | 11 |
| 6 | 74 |
| 7 | 1142 |
| 8 | 15 |

| Platelet Aggregation Inhibition (PAI) | | |
|---|---|---|
| Example | In vitro PAI $IC_{50}$ (nM) | Ex-vivo C. Monkey Whole Blood PAI |
| 1BN | 100–300 | — |
| 1DO | 300–1000 | — |
| 1DR | 100 | — |

| Platelet Aggregation Inhibition (PAI) | | |
|---|---|---|
| Example | In vitro PAI $IC_{50}$ (nM) | Ex-vivo C. Monkey Whole Blood PAI |
| 4 | 67 | 100% at 3 mpk* |
| 8 | 300 | 100% at 10 mpk** |

*oral in betahydroxypropylcyclodextrin as cosolvent.
**i.v. infusion over 30 min. in 5% dextrose

What is claimed is:
1. A compound represented by the structural formula

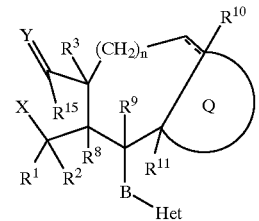

or a pharmaceutically acceptable salt thereof, wherein:
the single dotted line represents an optional double bond;
n is 0;
Q is

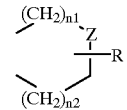

wherein
$n_1$ and $n_2$ are independently 0–2; or when the double bond is not present, Q is also fused R-substituted aryl;
R is 1 to 3 substituents independently selected from the group consisting of H, $C_1$–$C_6$ alkyl, halogen, hydroxy, and ($C_1$–$C_6$)alkoxy;
$R^1$ and $R^2$ are independently selected from the group consisting of H and $C_1$–$C_6$ alkyl;
$R^3$ is H or $C_1$–$C_6$ alkyl;
Het is W-pyridyl or W-quinolyl, wherein Het is attached to B by a carbon atom ring member, and wherein the Het group is substituted by 1 to 4 substituents, W, independently selected from the group consisting of H; $C_1$–$C_6$ alkyl; $C_1$–$C_6$ alkoxy; $R^{21}$-aryl; aryl wherein adjacent carbons form a ring with a methylenedioxy group; heteroaryl; heteroaryl substituted by 1 to 4 substituents selected from the group consisting of halogen, $C_1$–$C_6$ alkoxy, $C_1$–$C_6$ alkyl, ($C_1$–$C_6$)alkylamino, di-(($C_1$–$C_6$)alkyl)amino, —$OCF_3$, —$NO_2$, hydroxy($C_1$–$C_6$)alkyl, —CHO and phenyl; and heteroaryl wherein adjacent carbon atoms form a ring with a $C_3$–$C_5$ alkylene group or a methylenedioxy group;
$R^8$, $R^{10}$ and $R^{11}$ are H, provided that when the optional double bond is present, $R^{10}$ is absent, and when ring Q is aromatic, $R^{10}$ and $R^{11}$ are absent;
$R^9$ is H, OH, or $C_1$–$C_6$ alkoxy;
B is trans —CH═CH—;
X —OH;
Y═O, (H, H), (H, OH) or (H, $C_1$–$C_6$ alkoxy);
$R^{15}$ is H or —$NR^{18}R^{19}$;
$R^{16}$ is independently selected from the group consisting of $C_1$–$C_6$ lower alkyl, phenyl or benzyl;

$R^{17}$ is independently selected from the group consisting of H, $C_1$–$C_6$ alkyl, phenyl and benzyl;

$R^{18}$ and $R^{19}$ are independently selected from the group consisting of H and $C_1$–$C_6$ alkyl;

$R^{21}$ is 1 to 3 substutuents independently selected from the group consisting of —$CF_3$, —$OCF_3$, halogen, —$NO_2$, $C_1$–$C_6$ alkyl, $C_1$–$C_6$ alkoxy, ($C_1$–$C_6$)alkylamino, di-(($C_1$–$C_6$)alkyl)amino, amino($C_1$–$C_6$)alkyl, ($C_1$–$C_6$)-alkylamino($C_1$–$C_6$)alkyl, di-(($C_1$–$C_6$)alkyl)-amino($C_1$–$C_6$)alkyl, hydroxy-($C_1$–$C_6$)alkyl, —$COOR^{17}$, —$COR^{17}$, —$NHCOR^{16}$, —$NHSO_2R^{16}$ and —$NHSO_2CH_2CF_3$; and Z is —$CH_2$—.

2. A compound of claim 1 wherein Q is

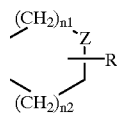

and $R^{10}$ and $R^{11}$ are each hydrogen.

3. A compound of claim 1 wherein $R^1$ is $C_1$–$C_6$ alkyl.

4. A compound of claim 1 wherein Q is R-substituted cyclohexyl or R-substituted phenyl.

5. A compound of claim 1 wherein R is H, fluorine, OH, $C_1$–$C_6$ alkyl, or $C_1$–$C_6$ alkoxy.

6. A compound of claim 1 wherein W is $C_1$–$C_6$ alkyl, aryl, $R^{21}$-aryl or heteroaryl.

7. A pharmaceutical composition comprising an effective amount of a compound of claim 1 and a pharmaceutically acceptable carrier.

8. A method of inhibiting thrombin receptors comprising administering to a mammal in need of such treatment an effective amount of a compound of claim 1.

9. A method of treating thrombosis, atherosclerosis, restenosis, hypertension, angina pectoris, arrhythmia, heart failure, myocardial infarction, glomerulonephritis, thrombotic stroke, thromboembolytic stroke, peripheral vascular diseases, inflammatory disorders, cerebral ischemia and cancer, comprising administering to a mammal in need of such treatment an effective amount of a compound of claim 1.

10. A compound selected from the group consisting of

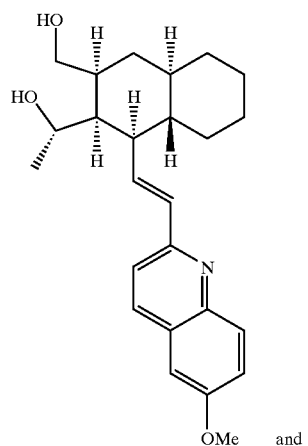

and

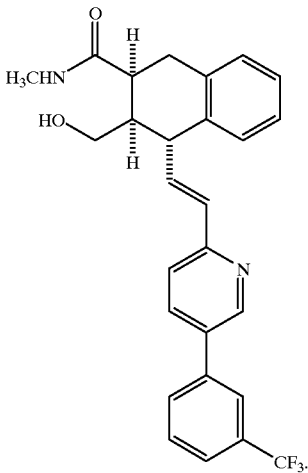

* * * * *